United States Patent
Li et al.

(10) Patent No.: US 11,623,923 B2
(45) Date of Patent: Apr. 11, 2023

(54) URACIL COMPOUND AS C-MET/AXL INHIBITOR

(71) Applicant: MEDSHINE DISCOVERY, INC., Jiangsu (CN)

(72) Inventors: Jinping Li, Shanghai (CN); Xiongbin Xu, Shanghai (CN); Gang Li, Shanghai (CN); Lihong Hu, Shanghai (CN); Charles Z. Ding, Shanghai (CN); Yaling Zhou, Shanghai (CN); Guoping Hu, Shanghai (CN); Jian Li, Shanghai (CN); Shuhui Chen, Shanghai (CN)

(73) Assignee: MEDSHINE DISCOVERY, INC., Jiangsu (CN)

( * ) Notice: Subject to any disclaimer, the term of this patent is extended or adjusted under 35 U.S.C. 154(b) by 63 days.

(21) Appl. No.: 16/766,510

(22) PCT Filed: Nov. 23, 2018

(86) PCT No.: PCT/CN2018/117269
§ 371 (c)(1),
(2) Date: Jun. 25, 2020

(87) PCT Pub. No.: WO2019/101178
PCT Pub. Date: May 31, 2019

(65) Prior Publication Data
US 2021/0371395 A1    Dec. 2, 2021

(30) Foreign Application Priority Data

Nov. 24, 2017 (CN) .......................... 201711190571.6
Sep. 30, 2018 (CN) .......................... 201811159913.2

(51) Int. Cl.
| | | |
|---|---|---|
| C07D 401/12 | (2006.01) |
| C07D 401/14 | (2006.01) |
| A61P 35/00 | (2006.01) |
| C07D 405/14 | (2006.01) |
| C07D 487/04 | (2006.01) |

(52) U.S. Cl.
CPC ............ C07D 401/12 (2013.01); A61P 35/00 (2018.01); C07D 401/14 (2013.01); C07D 405/14 (2013.01); C07D 487/04 (2013.01)

(58) Field of Classification Search
CPC .......................... C07D 401/12; C07D 401/14
See application file for complete search history.

(56) References Cited

FOREIGN PATENT DOCUMENTS

| | | |
|---|---|---|
| CN | 106543145 A | 3/2017 |
| WO | 2013074633 A1 | 5/2013 |
| WO | WO 2019/213340 | * 11/2019 |

OTHER PUBLICATIONS

PCT/CN2018/117269, Feb. 28, 2019, International Search Report and Written Opinion.

* cited by examiner

*Primary Examiner* — Brian E McDowell
(74) *Attorney, Agent, or Firm* — McDermott Will & Emery LLP

(57) ABSTRACT

Provided are a uracil compound represented by Formula (IV) or a pharmaceutically acceptable salt thereof and a pharmaceutical composition of the same. Also provided is a use thereof as a c-MET/AXL inhibitor in preparing a c-MET/AXL-inhibiting drug or a drug for treating a tumor.

(IV)

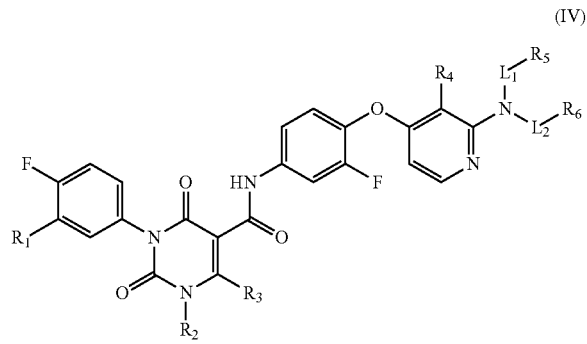

23 Claims, No Drawings

URACIL COMPOUND AS C-MET/AXL INHIBITOR

REFERENCE TO RELATED APPLICATIONS

This application is a national stage filing under 35 U.S.C. § 371 of international application number PCT/CN2018/117269, filed on Nov. 23, 2018, which claims the benefit of priority to Chinese Patent Application No. 201811159913.2, filed on Sep. 30, 2018, and Chinese Patent Application No. 201711190571.6, filed on Nov. 24, 2017. The entire contents of each of the prior applications are herein incorporated by reference.

TECHNICAL FIELD

The present disclosure relates to a class of uracil compounds as c-MET/AXL inhibitor, and specifically disclosed herein is a compound of Formula (IV) or a pharmaceutically acceptable salt thereof.

BACKGROUND

The c-Met encoded by proto-oncogene Met is a highly binding receptor tyrosine kinase that belongs to the RON subfamily and is the only known receptor for scattering factor or hepatocyte growth factor (HGF). The c-Met protein is a heterodimer of α subunit of 50 kD and β subunit of 145 kD connected by a disulfide bond, and is divided into an extracellular domain and an intracellular domain. The extracellular domain contains three domains with different functions: N-terminal ligand binding domain (SEMA region) covering the entire α chain and part of the β chain, cystine-rich region with four conserved disulfide bonds, and immunoglobulin-like domain. The intracellular domain is also consisted of three regulatory regions: juxtamembrane domain with Tyr1003 phosphorylation site, tyrosine kinase catalytic domain with Tyr1234 and Tyr1235 phosphorylation sites, and C-terminal multifunctional binding region with Tyr1349 and Tyr1356 binding tyrosine.

HGF, after binding to the extracellular domain of c-Met, induces phosphorylation of c-Met, recruits a variety of interstitial factors such as GAB1 (growth factor receptor binding protein-1) and GAB2 (growth factor receptor binding protein-2), etc., and further attracts SHP2, PI3K and other molecules to bind here, thereby activating RAS/MAPK, PI3K/AKT, JAK/STAT pathway, etc., and regulating cell growth, migration, proliferation and survival. Abnormal c-Met pathway can induce tumor occurrence and metastasis, and abnormally high levels of c-Met expression are found in various human malignant tumors such as bladder cancer, gastric cancer, lung cancer, and breast cancer. In addition, c-Met is also associated with tumor resistance to multiple kinase inhibitors.

There is crosstalk between c-Met and various membrane receptors, forming a complex network system. The crosstalk between c-Met and adhesion receptor CD44 amplifies the response of signal peptide; the crosstalk between c-Met and brain protein receptor activates the ligand HGF-independent c-Met, enhancing the invasion effect; the crosstalk between c-Met and pro-apoptotic receptor FAS accelerates cell apoptosis; and the crosstalk between c-Met and various receptor tyrosine kinases such as EGFR and VEGFR regulates the activation of each other and affects the angiogenesis process. The crosstalk between c-Met and these membrane receptors promotes tumor development and metastasis, and induces drug resistance.

AXL is a transmembrane protein, in which the extracellular region includes two immunoglobulin-like regions and two fibronectin-like regions, and the ligand binding region is an immunoglobulin-like region. AXL, together with Tyro3 and Mer, belongs to the family of TAM receptor tyrosine kinases, and they all use protein molecules encoded by growth arrest specific gene 6 (Gas6) and human plasma anticoagulant protein S as ligands. When AXL binds to Gas6, the conformation of AXL changes, forming a dimer. Tyrosine residues in the inner segment of the membrane are phosphorylated, thereby activating the activity of tyrosine protein kinase of AXL itself, which in turn phosphorylates downstream proteins to play a signaling role. AXL activation can cause GRB2 activation, which can affect tumor cell proliferation through the RAS-RAF-MEK-ERK signaling pathway, or can also phosphorylate PI3K to activate AKT, thereby enhancing tumor cell survival. In addition, AXL can promote the migration and invasion of tumor cells by directly activating SRC or by interacting with EGFR, VEGFR and MET, which can lead to the aggravation of tumor metastasis. The high expression of AXL protein is associated with the aggravation of breast cancer, lung cancer, and acute myeloid leukemia. Studies have shown that AXL signal activation is one of main mechanisms for tumor cells to undergo epithelial-mesenchymal transition (EMT) and one of main mechanisms for cancer cells to develop resistance to targeted drugs and chemotherapeutic drugs.

At present, there are many anti-tumor drugs on the market, such as alkylating agent drugs, antimetabolite drugs, anti-tumor antibiotics, immunomodulators, etc., but most of them are not tolerated by patients due to high toxicity. With the study of tumor molecular biology progresses, the molecular mechanism of tumor occurrence and development is becoming more and more clear, and molecular targeted therapy for a variety of malignant tumors has received extensive interest and high attention. Molecular targeted drugs have high selectivity and broad-spectrum effectiveness, are superior to cytotoxic chemotherapy drugs in safety, and represent a new direction of development in the field of cancer therapy.

The c-Met inhibitors currently under development can be divided into selective inhibitors and multi-target inhibitors. The selective inhibitor Tepotinib (EMD1214063) (WO2009006959, published on Jan. 15, 2009) has the best antitumor activity, with a strong inhibitory effect on a variety of tumor cells that highly express c-MET (the activity for c-MET enzyme, $IC_{50}=3.67$ nM, for MHCC97H cell, $IC_{50}=6.2$ nM), and has entered the stage of clinical phase II. Multi-target c-Met inhibitors are represented by BMS777607 (US2008114033), MGCD265 (WO2006010264), LY2801653 (US2010022529), and NPS-1034 (US2011183983). A patent application US2009094427 discloses a series of compounds of the following general formula (A).

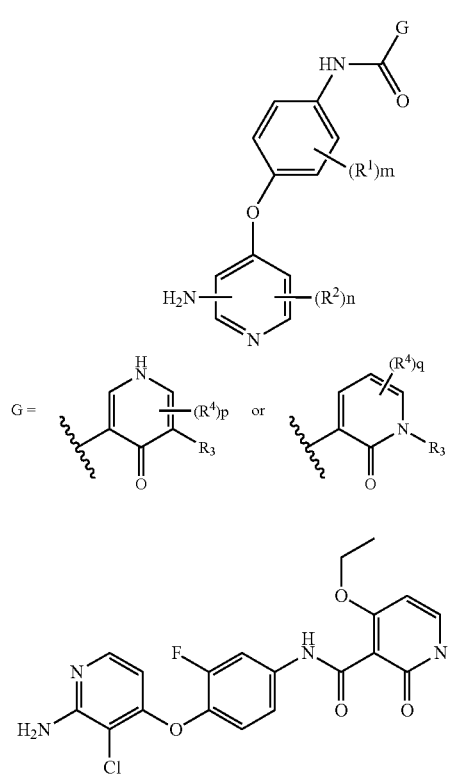

BMS777607

SUMMARY

The present disclosure provides a compound of Formula (I) or a pharmaceutically acceptable salt thereof,

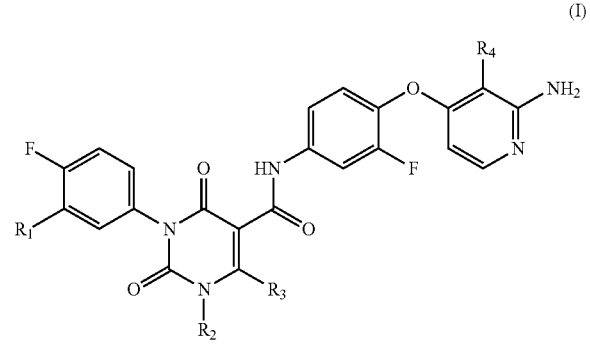

wherein,
$R_1$ is selected from the group consisting of H, halogen and $C_{1-6}$ alkyl;
$R_2$ is selected from the group consisting of H, $NH_2$, $C_{1-6}$ alkyl, $C_{1-6}$ heteroalkyl, $C_{2-6}$ alkenyl, $C_{3-6}$ cycloalkyl and 3- to 6-membered heterocycloalkyl, wherein the $C_{1-6}$ alkyl, $C_{1-6}$ heteroalkyl, $C_{2-6}$ alkenyl and 3- to 6-membered heterocycloalkyl are optionally substituted with 1, 2 or 3 R;
$R_3$ is selected from the group consisting of H, $C_{1-4}$ alkyl and $C_{3-6}$ cycloalkyl;
alternatively, $R_2$ and $R_3$ are connected to form a 5- to 6-membered saturated heterocycle, wherein the 5- to 6-membered saturated heterocycle is optionally substituted with 1, 2 or 3 R;

$R_4$ is selected from the group consisting of H, halogen, $C_{1-4}$ alkyl, $C_{1-4}$ heteroalkyl, $C_{3-6}$ cycloalkyl, 3- to 6-membered heterocycloalkyl and 5- to 6-membered heteroaryl;
R is each independently selected from the group consisting of F, Cl, Br, I, OH, CN, $NH_2$, $C_{1-4}$ alkyl, $C_{1-4}$ heteroalkyl, $C_{3-6}$ cycloalkyl and 3- to 6-membered heterocycloalkyl, wherein the $C_{1-4}$ alkyl, $C_{1-4}$ heteroalkyl, $C_{3-6}$ cycloalkyl and 3- to 6-membered heterocycloalkyl are optionally substituted with 1, 2 or 3 R';
R' is selected from the group consisting of F, Cl, Br, I, OH, CN, $NH_2$, $CH_3$, $CF_3$, $CHF_2$, $CH_3O$, $CH_3CH_2$, $CH_3CH_2O$, COOH, $NH(CH_3)$, $N(CH_3)_2$, the $C_{1-6}$ heteroalkyl, 3- to 6-membered heterocycloalkyl, 5- to 6-membered saturated heterocycle, $C_{1-4}$ heteroalkyl and 5- to 6-membered heteroaryl each independently contains 1, 2 or 3 heteroatoms or heteroatom groups selected from the group consisting of —NH—, —O—, —S—, =O, =S, —C(=O)O—, —C(=O)—, —C(=O)NH—, —C(=S)—, —S(=O)—, —S(=O)$_2$—, —C(=NH)—, —S(=O)$_2$NH—, —S(=O)NH—, and —NHC(=O)NH—.

In some embodiments disclosed herein, the above-mentioned R is selected from the group consisting of F, Cl, Br, I, OH, CN, $NH_2$, $CH_3$, $CF_3$, $CHF_2$, $CH_3O$, $CH_3CH_2$, $CH_3CH_2O$, COOH, $NH(CH_3)$, $N(CH_3)_2$, In some embodiments disclosed herein, the above-mentioned $R_1$ is H.

In some embodiments disclosed herein, the above-mentioned $R_2$ is selected from the group consisting of H, $NH_2$, $C_{1-4}$ alkyl, $C_{1-4}$ heteroalkyl and $C_{2-4}$ alkenyl, wherein the $C_{1-4}$ alkyl, $C_{1-4}$ heteroalkyl and $C_{2-4}$ alkenyl are optionally substituted with 1, 2 or 3 R.

In some embodiments disclosed herein, the above-mentioned $R_2$ is selected from the group consisting of H, $CH_3$, In some embodiments disclosed herein, the above-mentioned $R_3$ is selected from the group consisting of H, $C_{1-3}$ alkyl and $C_{3-4}$ cycloalkyl.

In some embodiments disclosed herein, the above-mentioned $R_3$ is selected from the group consisting of H, $CH_3$, $CH_3CH_2$ and

In some embodiments disclosed herein, the above-mentioned $R_4$ is Cl.

In some embodiments disclosed herein, the above-mentioned moiety

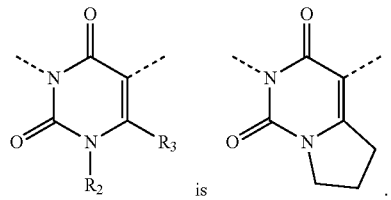

is

In some embodiments disclosed herein, the above-mentioned R is selected from the group consisting of F, Cl, Br, I, OH, CN, $NH_2$, $CH_3$, $CF_3$, $CHF_2$, $CH_3O$, $CH_3CH_2$, $CH_3CH_2O$, COOH, $NH(CH_3)$, $N(CH_3)_2$,

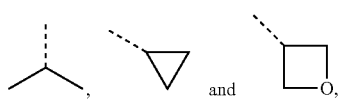

and the other variables are as defined above.

In some embodiments disclosed herein, the above-mentioned $R_1$ is H, and the other variables are as defined above.

In some embodiments disclosed herein, the above-mentioned $R_2$ is selected from the group consisting of H, $NH_2$, $C_{1-4}$ alkyl, $C_{1-4}$ heteroalkyl and $C_{2-4}$ alkenyl, wherein the $C_{1-4}$ alkyl, $C_{1-4}$ heteroalkyl and $C_{2-4}$ alkenyl are optionally substituted with 1, 2 or 3 R, and the other variables are as defined above.

In some embodiments disclosed herein, the above-mentioned $R_2$ is selected from the group consisting of H, $CH_3$,

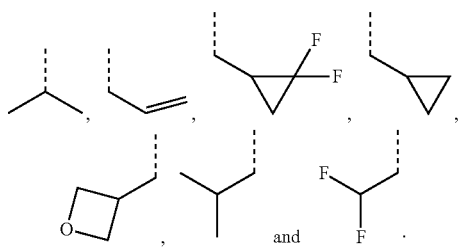

and the other variables are as defined above.

In some embodiments disclosed herein, the above-mentioned $R_3$ is selected from the group consisting of H, $C_{1-3}$ alkyl and $C_{3-4}$ cycloalkyl, and the other variables are as defined above.

In some embodiments disclosed herein, the above-mentioned $R_3$ is selected from the group consisting of H, $CH_3$, $CH_3CH_2$ and

and the other variables are as defined above.

In some embodiments disclosed herein, the above-mentioned $R_4$ is Cl, and the other variables are as defined above.

In some embodiments disclosed herein, the above-mentioned moiety

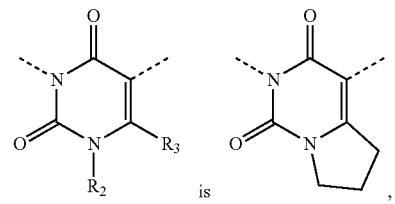

is and the other variables are as defined above.

The present disclosure also includes some embodiments that are obtained by combining any of the above-mentioned variables.

In some embodiments disclosed herein, the above-mentioned compounds are:

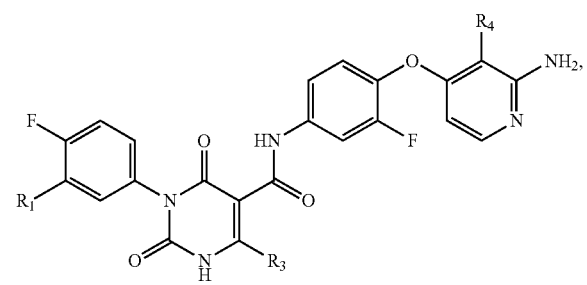

(II)

wherein $R_3$ is selected from the group consisting of $C_{1-4}$ alkyl and $C_{3-6}$ cycloalkyl, and R, $R_1$ and $R_4$ are as defined above.

In some embodiments disclosed herein, the above-mentioned compounds are:

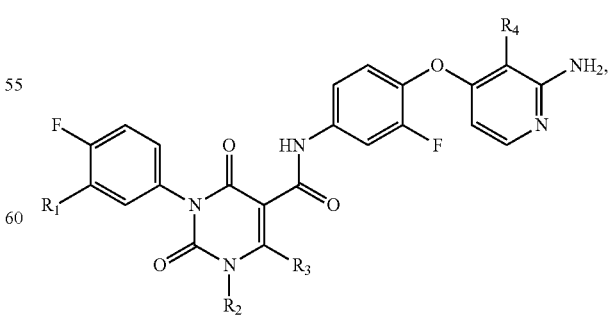

(III)

wherein $R_2$ is selected from the group consisting of $NH_2$, $C_{1-6}$ alkyl, $C_{1-6}$ heteroalkyl and $C_{2-6}$ alkenyl, wherein the $C_{1-6}$ alkyl, $C_{1-6}$ heteroalkyl and $C_{2-6}$ alkenyl are optionally substituted with 1, 2 or 3 R, and R, $R_1$ and $R_4$ are as defined above.

The present disclosure provides a compound of Formula (IV) or a pharmaceutically acceptable salt thereof,

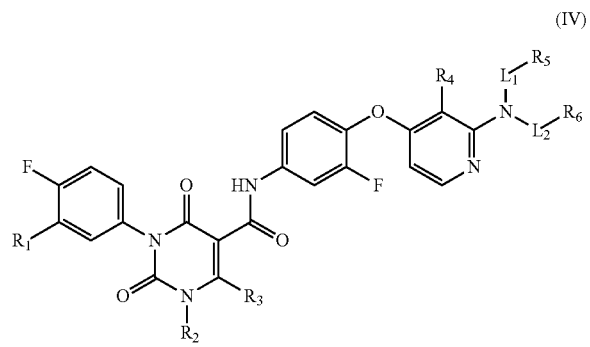

(IV)

wherein,
$R_1$ is selected from the group consisting of H, halogen and $C_{1-6}$ alkyl;
$R_2$ is selected from the group consisting of H, $NH_2$, $C_{1-6}$ alkyl, $C_{1-6}$ heteroalkyl, $C_{2-6}$ alkenyl, $C_{3-6}$ cycloalkyl and 3- to 6-membered heterocycloalkyl, wherein the $C_{1-6}$ alkyl, $C_{1-6}$ heteroalkyl, $C_{2-6}$ alkenyl, and 3- to 6-membered heterocycloalkyl are optionally substituted with 1, 2 or 3 R;
$R_3$ is selected from the group consisting of H, $C_{1-4}$ alkyl and $C_{3-6}$ cycloalkyl, wherein the $C_{1-4}$ alkyl and $C_{3-6}$ cycloalkyl are optionally substituted with 1, 2 or 3 R';
alternatively, $R_2$ and $R_3$ are connected to form a 5- to 6-membered saturated heterocycle, wherein the 5- to 6-membered saturated heterocycle is optionally substituted with 1, 2 or 3 R;
$R_4$ is selected from the group consisting of H, CN, halogen, $C_{1-4}$ alkyl, $C_{1-4}$ heteroalkyl, $C_{3-6}$ cycloalkyl, 3- to 6-membered heterocycloalkyl and 5- to 6-membered heteroaryl;
$R_5$ and $R_6$ are each independently selected from the group consisting of H, $NH_2$, $C_{1-6}$ alkyl, $C_{1-6}$ heteroalkyl, $C_{3-6}$ cycloalkyl, and 3- to 6-membered heterocycloalkyl, wherein the $C_{1-6}$ alkyl, $C_{1-6}$ heteroalkyl, $C_{3-6}$ cycloalkyl, and 3- to 6-membered heterocycloalkyl are optionally substituted with 1, 2 or 3 R;
$L_1$ and $L_2$ are each independently selected from the group consisting of a single bond and —C(=O)—;
R is each independently selected from the group consisting of F, Cl, Br, I, OH, CN, $NH_2$, $C_{1-4}$ alkyl, $C_{1-4}$ heteroalkyl, $C_{3-6}$ cycloalkyl, and 3- to 6-membered heterocycloalkyl, wherein the $C_{1-4}$ alkyl, $C_{1-4}$ heteroalkyl, $C_{3-6}$ cycloalkyl, and 3- to 6-membered heterocycloalkyl are optionally substituted with 1, 2 or 3 R';
R' is selected from the group consisting of F, Cl, Br, I, OH, CN, $NH_2$, $CH_3$, $CF_3$, $CHF_2$, $CH_3O$, $CH_3CH_2$, $CH_3CH_2O$, COOH, $NH(CH_3)$, $N(CH_3)_2$,

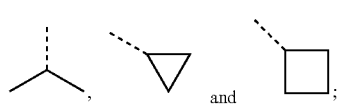

and the $C_{1-6}$ heteroalkyl, 3- to 6-membered heterocycloalkyl, 5- to 6-membered saturated heterocycle, $C_{1-4}$ heteroalkyl and 5- to 6-membered heteroaryl each independently contains 1, 2 or 3 heteroatoms or heteroatom groups selected from the group consisting of N, —NH—, —O—, —S—, =O, =S, —C(=O)O—, —C(=O)—, —C(=O)NH—, —C(=S)—, —S(=O)—, —S(=O)$_2$—, —C(=NH)—, —S(=O)$_2$NH—, —S(=O)NH—, and —NHC(=O)NH—.

In some embodiments disclosed herein, the above-mentioned R is selected from the group consisting of F, Cl, Br, I, OH, CN, $NH_2$, $CH_3$, $CF_3$, $CHF_2$, $CH_3O$, $CH_3CH_2$, $CH_3CH_2O$, COOH, $NH(CH_3)$, $N(CH_3)_2$,

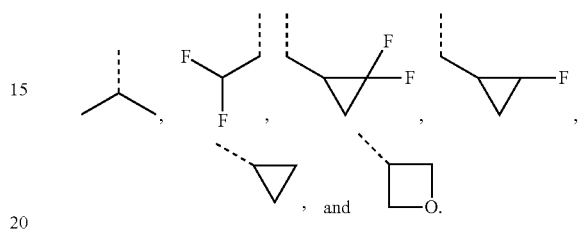

In some embodiments disclosed herein, the above-mentioned $R_1$ is H.

In some embodiments disclosed herein, the above-mentioned $R_2$ is selected from the group consisting of H, $NH_2$, $C_{1-4}$ alkyl, $C_{1-4}$ heteroalkyl and $C_{2-4}$ alkenyl, wherein the $C_{1-4}$ alkyl, $C_{1-4}$ heteroalkyl and $C_{2-4}$ alkenyl are optionally substituted with 1, 2 or 3 R.

In some embodiments disclosed herein, the above-mentioned $R_2$ is selected from the group consisting of H, $NH_2$, $CH_3$, $CH_3CH_2$,

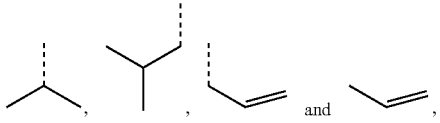

wherein the $CH_3$, $CH_3CH_2$,

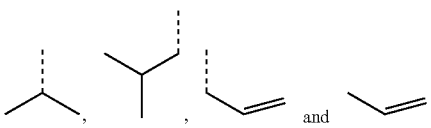

are optionally substituted with 1, 2 or 3 R.

In some embodiments disclosed herein, the above-mentioned $R_2$ is selected from the group consisting of H, $CH_3$,

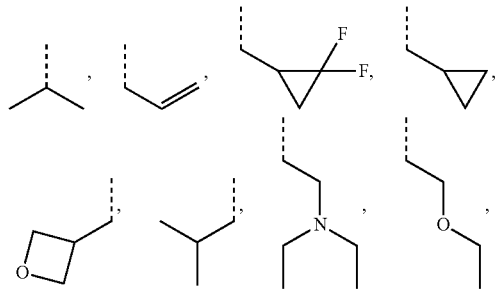

-continued

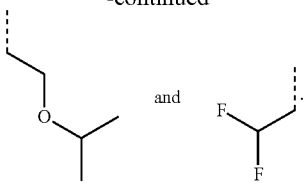

In some embodiments disclosed herein, the above-mentioned $R_3$ is selected from the group consisting of H, $C_{1-3}$ alkyl and $C_{3-4}$ cycloalkyl, wherein the $C_{1-3}$ alkyl and $C_{3-4}$ cycloalkyl are optionally substituted with 1, 2 or 3 R';

In some embodiments disclosed herein, the above-mentioned $R_3$ is selected from the group consisting of H, $CH_3$, $CH_3CH_2$ and

In some embodiments disclosed herein, the above-mentioned $R_4$ is selected from the group consisting of H, Cl and CN.

In some embodiments disclosed herein, the above-mentioned $R_5$ and $R_6$ are each independently selected from the group consisting of H, $NH_2$, $CH_3$, $CH_3CH_2$,

wherein the $CH_3$, $CH_3CH_2$,

-continued

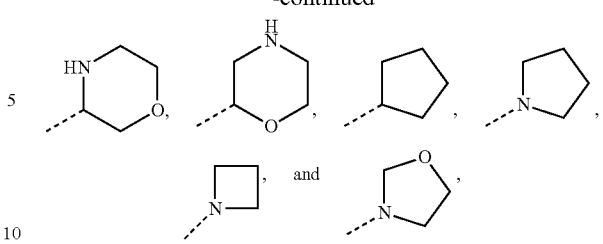

are optionally substituted with 1, 2 or 3 R.

In some embodiments disclosed herein, the above-mentioned $R_5$ and $R_6$ are each independently selected from the group consisting of H, $NH_2$, $CH_3$, $CH_3CH_2$,

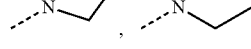

In some embodiments disclosed herein, the above-mentioned moiety

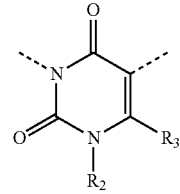

is selected from the group consisting of

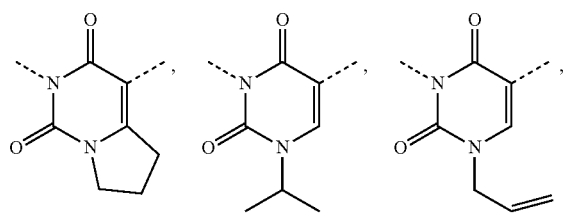

-continued
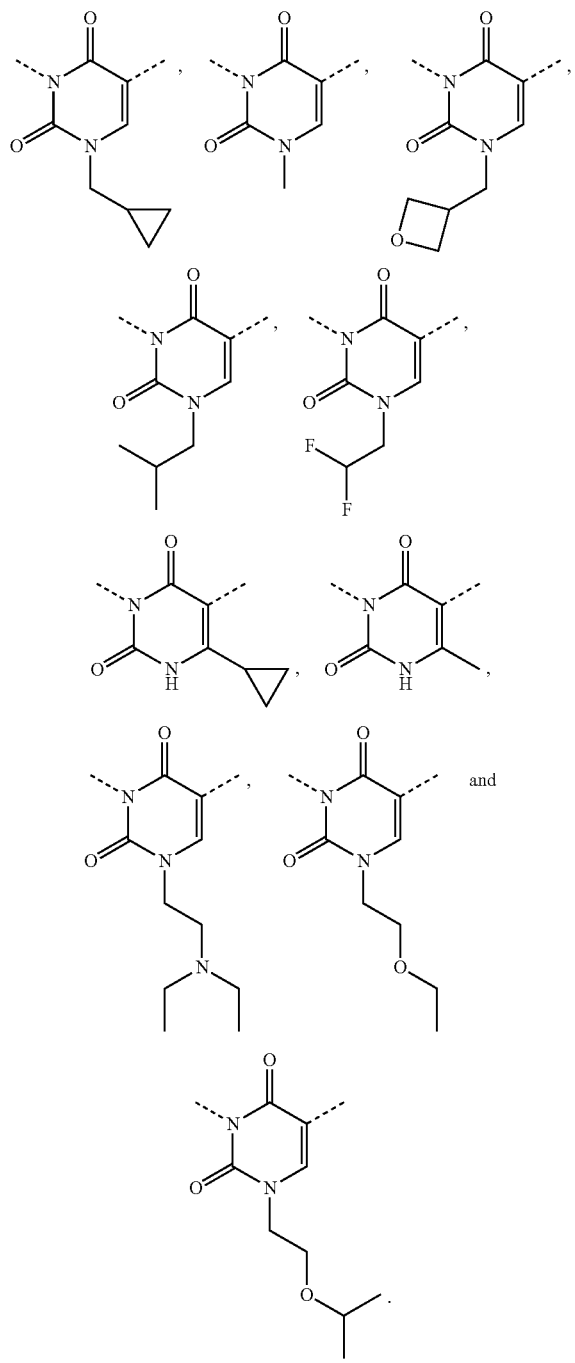
In some embodiments disclosed herein, the above-mentioned moiety
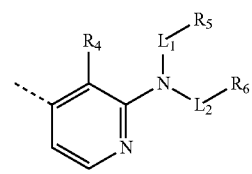
is selected from the group consisting of
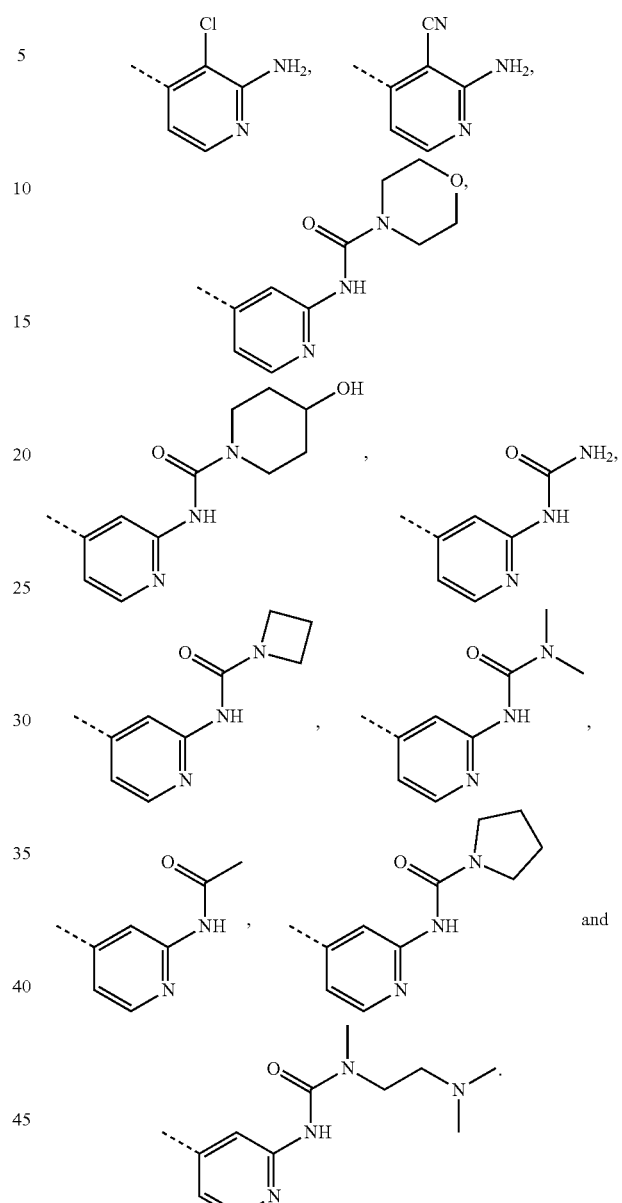
In some embodiments disclosed herein, the above-mentioned R is selected from the group consisting of F, Cl, Br, I, OH, CN, $NH_2$, $CH_3$, $CF_3$, $CHF_2$, $CH_3O$, $CH_3CH_2$, $CH_3CH_2O$, COOH, $NH(CH_3)$, $N(CH_3)_2$,
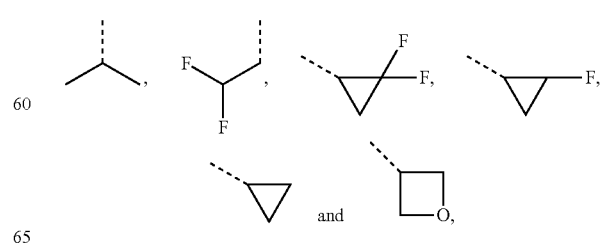
the other variables are as defined herein.

In some embodiments disclosed herein, the above-mentioned $R_1$ is H, and the other variables are as defined herein.

In some embodiments disclosed herein, the above-mentioned $R_2$ is selected from the group consisting of H, $NH_2$, $C_{1-4}$ alkyl, $C_{1-4}$ heteroalkyl and $C_{2-4}$ alkenyl, wherein the $C_{1-4}$ alkyl, $C_{1-4}$ heteroalkyl and $C_{2-4}$ alkenyl are optionally substituted with 1, 2 or 3 R, and the other variables are as defined herein.

In some embodiments disclosed herein, the above-mentioned $R_2$ is selected from the group consisting of H, $NH_2$, $CH_3$, $CH_3CH_2$,

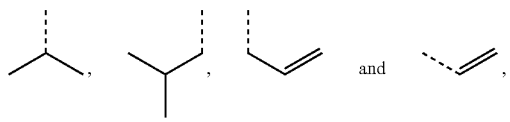

wherein the $CH_3$, $CH_3CH_2$,

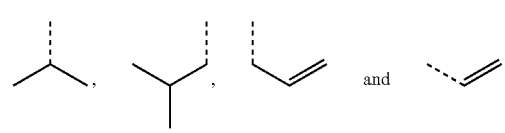

are optionally substituted with 1, 2 or 3 R, and the other variables are as defined herein.

In some embodiments disclosed herein, the above-mentioned $R_2$ is selected from the group consisting of H, $CH_3$,

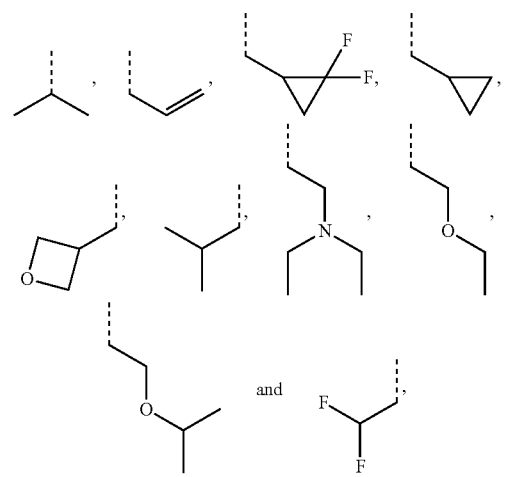

and the other variables are as defined herein.

In some embodiments disclosed herein, the above-mentioned $R_3$ is selected from the group consisting of H, $C_{1-3}$ alkyl and $C_{3-4}$ cycloalkyl, wherein the $C_{1-3}$ alkyl and $C_{3-4}$ cycloalkyl are optionally substituted with 1, 2 or 3 R', and the other variables are as defined herein.

In some embodiments disclosed herein, the above-mentioned $R_3$ is selected from the group consisting of H, $CH_3$, $CH_3CH_2$ and

and the other variables are as defined herein.

In some embodiments disclosed herein, the above-mentioned $R_4$ is selected from the group consisting of H, Cl and CN, and the other variables are as defined herein.

In some embodiments disclosed herein, the above-mentioned $R_5$ and $R_6$ are each independently selected from the group consisting of H, $NH_2$, $CH_3$, $CH_3CH_2$,

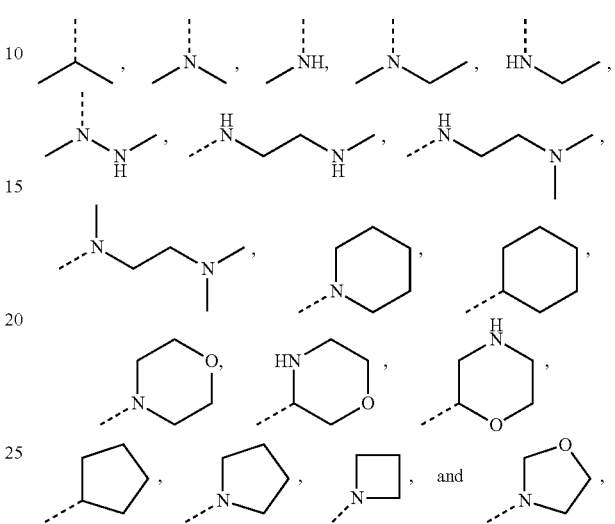

wherein the $CH_3$, $CH_3CH_2$,

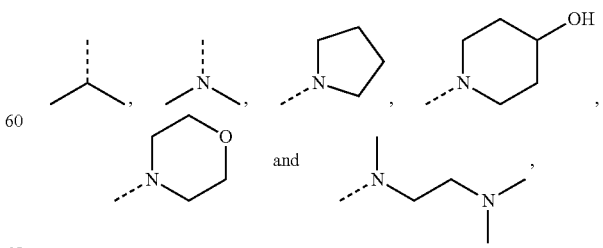

are optionally substituted with 1, 2 or 3 R, and the other variables are as defined herein.

In some embodiments disclosed herein, the above-mentioned $R_5$ and $R_6$ are each independently selected from the group consisting of H, $NH_2$, $CH_3$, $CH_3CH_2$, and the other variables are as defined herein.

In some embodiments disclosed herein, the above-mentioned moiety
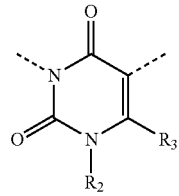
is selected from the group consisting of
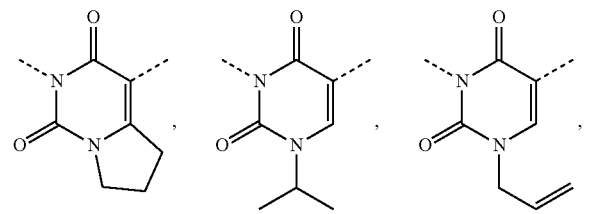
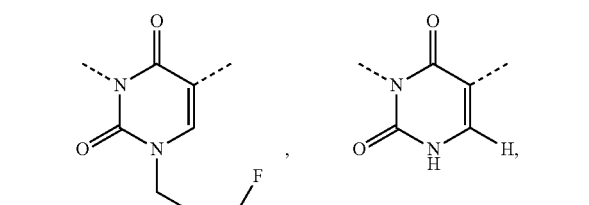
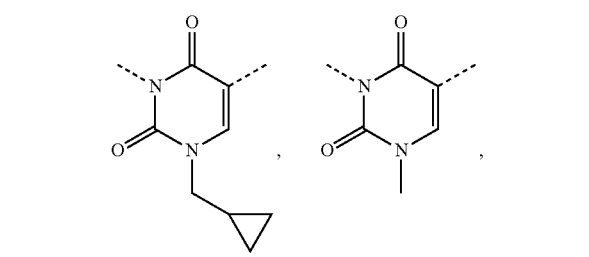
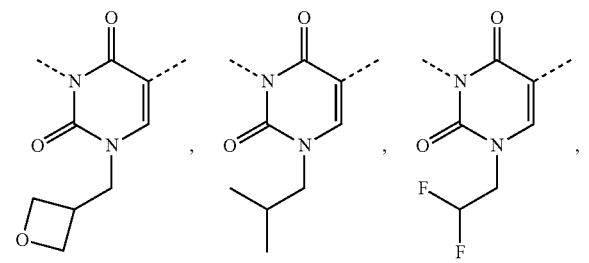
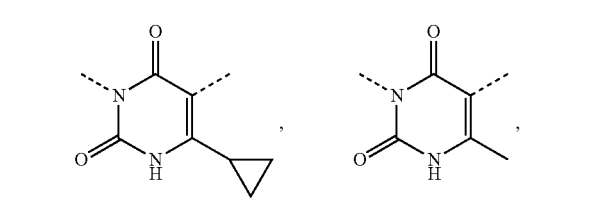
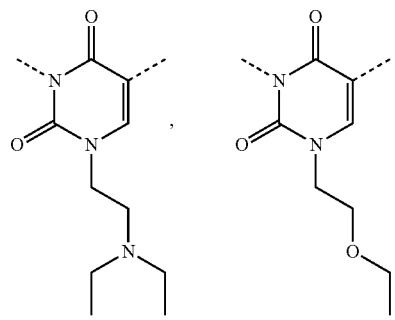
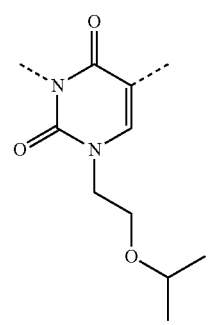
and the other variables are as defined herein.
In some embodiments disclosed herein, the above-mentioned moiety
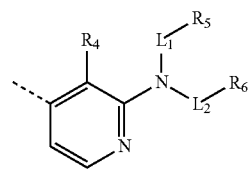
is selected from the group consisting of
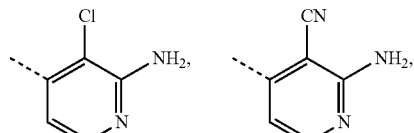
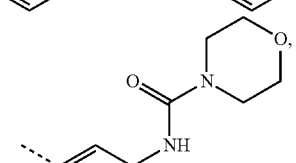
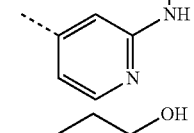
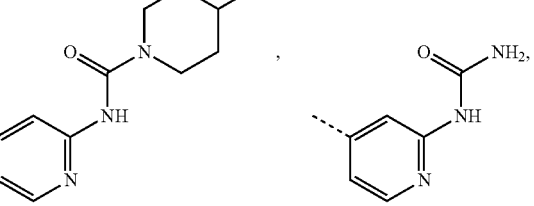

and the other variables are as defined herein.

In some embodiments disclosed herein, the above-mentioned compound or a pharmaceutically acceptable salt thereof are disclosed, wherein the compound is:

(IV-1)

wherein $R_3$ is selected from the group consisting of $C_{1-4}$ alkyl and $C_{3-6}$ cycloalkyl, and $L_1$, $L_2$, $R_1$, $R_4$, $R_5$ and $R_6$ are as defined herein.

In some embodiments disclosed herein, the above-mentioned compound or a pharmaceutically acceptable salt thereof are disclosed, wherein the compound is:

(IV-2)

wherein,
$R_2$ is selected from the group consisting of $NH_2$, $C_{1-6}$ alkyl, $C_{1-6}$ heteroalkyl and $C_{2-6}$ alkenyl, wherein the $C_{1-6}$ alkyl, $C_{1-6}$ heteroalkyl and $C_{2-6}$ alkenyl are optionally substituted with 1, 2 or 3 R; and
$L_1$, $L_2$, $R_1$, $R_4$, $R_5$, $R_6$ and R are as defined herein.

In some embodiments disclosed herein, the above-mentioned compound or a pharmaceutically acceptable salt thereof are disclosed, wherein the compound is:

(IV-3)

wherein $L_1$, $L_2$, $R_1$, $R_4$, $R_5$ and $R_6$ are as defined herein.

In some embodiments disclosed herein, the above-mentioned compound or a pharmaceutically acceptable salt thereof are disclosed, wherein the compound is selected from the group consisting of:

(IV-4)

and (IV-5)

wherein $R_1$, $R_4$ and $R_5$ are as defined herein.

The present disclosure also provides a compound or a pharmaceutically acceptable salt thereof, wherein the compound is selected from the group consisting of:
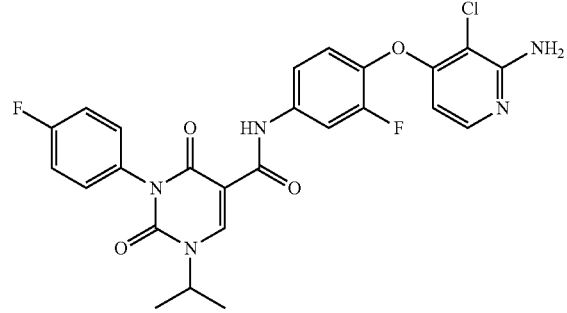
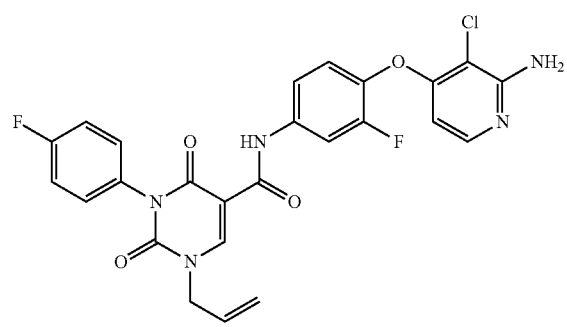
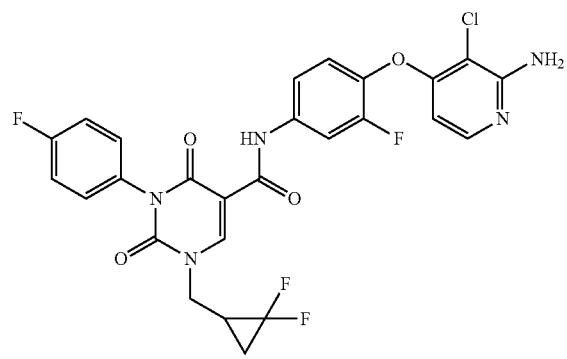
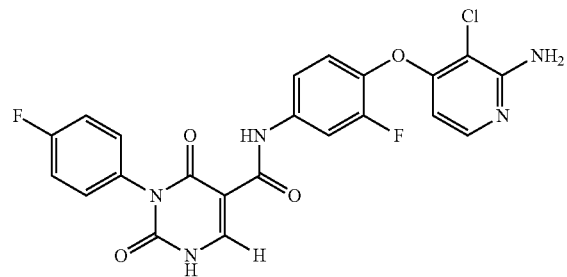
-continued
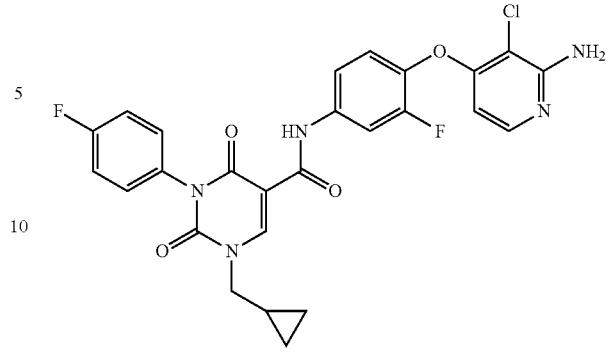
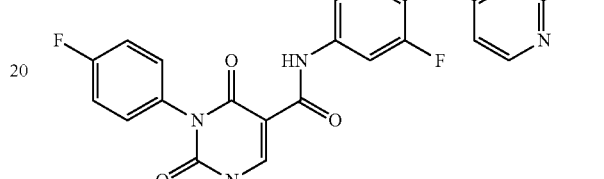
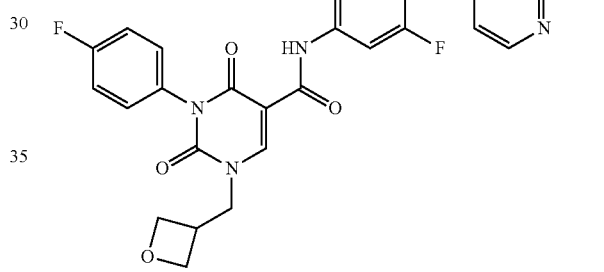
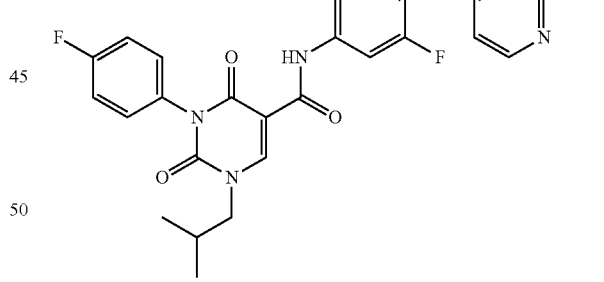
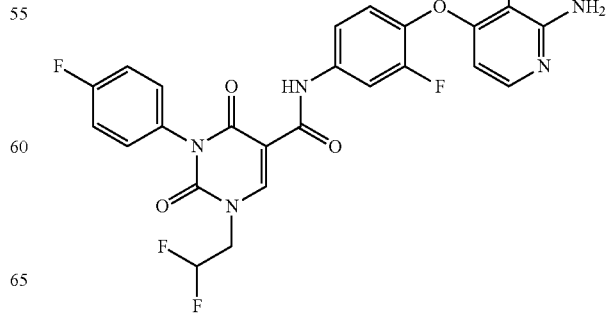

21
-continued
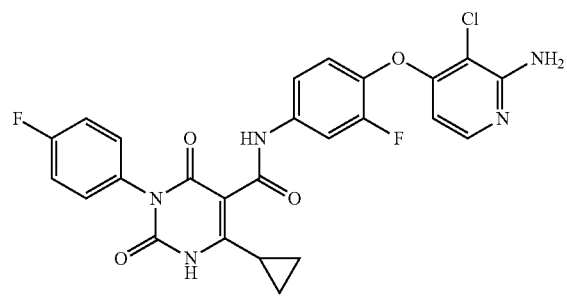
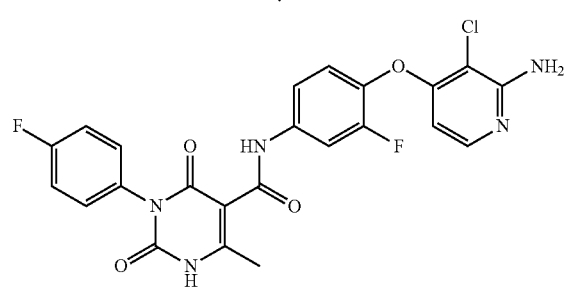
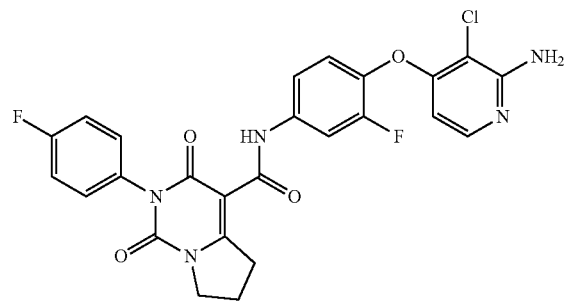
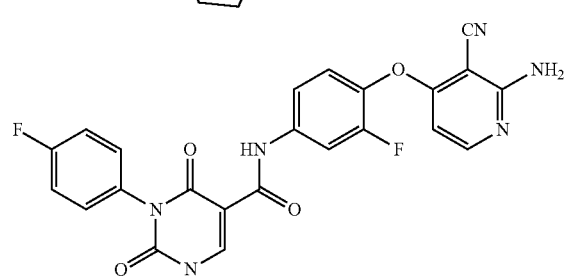
22
-continued
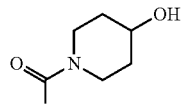
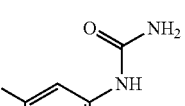
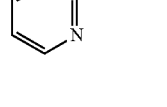
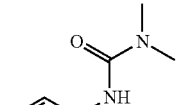
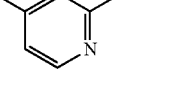

-continued

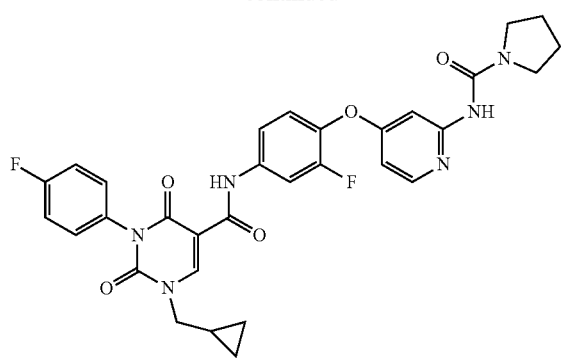

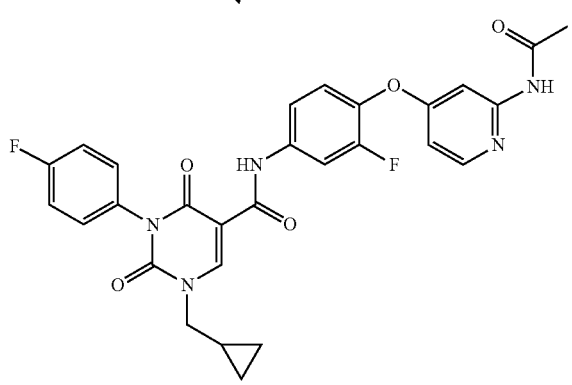

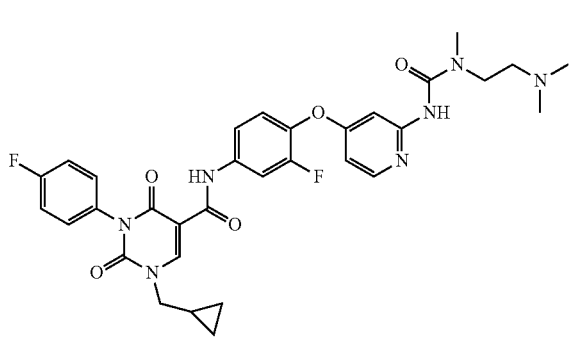

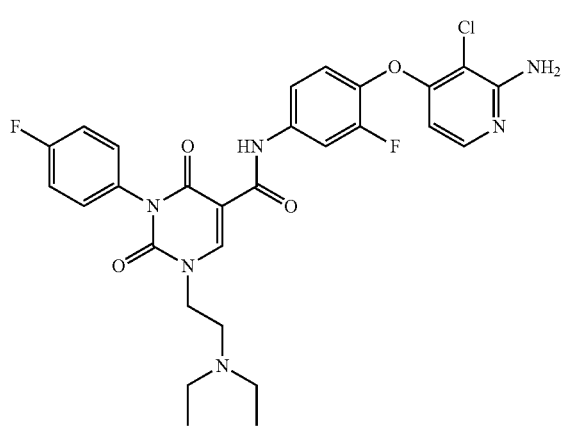

-continued

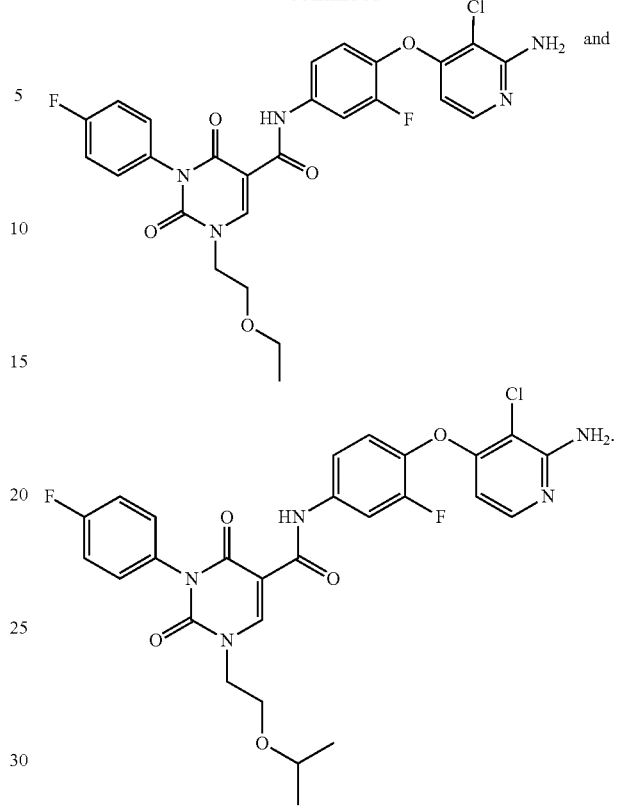

The present disclosure also provides a pharmaceutical composition, comprising a therapeutically effective amount of the above-mentioned compound, or a pharmaceutically acceptable salt thereof, and pharmaceutically acceptable carrier(s).

The present disclosure also provides the use of the above-mentioned compound, or a pharmaceutically acceptable salt thereof, or the above-mentioned composition in the manufacture of a medicament for inhibiting c-MET/AXL.

In some embodiments disclosed herein, the above-mentioned medicament for inhibiting c-MET/AXL is a medicament for treating a tumor.

The present disclosure also includes some embodiments that are obtained by combining any of the above-mentioned variables.

Technical Effect

The compound disclosed herein has prolonged half-life, extended action time against the target, enhanced metabolic stability, and excellent inhibitory activity. The prolongation of half-life will maintain the blood drug concentration for a longer time. From this, it can be predicted that the treatment of tumors using the compound disclosed herein will lead to the reduction in dosage or frequency of administration of patients as compared with similar drugs, and thus significantly improving the patient compliance.

After the binding of HGF and c-MET, MAPK, PI3K/AKT, Cdc42/Rac1 and other cell signaling pathways are activated, leading to the survival and proliferation of cancer cells, thereby accelerating tumor growth. Therefore, uracil compounds as c-MET inhibitors have great prospects as targeted therapeutic drugs for liver cancer, non-small cell lung cancer, gastric cancer and other cancers. Therefore, the compounds disclosed herein act as uracil c-MET inhibitors. Moreover, the excessive activation of AXL is also involved in tumor metastasis, phenotype of tumor stem cells, development of drug resistance of tumor cells, immunosuppression, etc. Uracil compounds as AXL inhibitors have great prospects in the treatment of acute lymphatic myeloma, non-small cell lung cancer, gastric cancer, breast cancer, and other therapeutic fields. In view of significant inhibitory activities and good pharmacokinetic properties in vivo and in vivo, the compounds disclosed herein are expected to become new drugs with better therapeutic effects than similar products.

Definitions and Terms

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound disclosed herein that is prepared by reacting the compound having a specific substituent disclosed herein with a relatively non-toxic acid or base. When the compound disclosed herein contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound disclosed herein contains a relatively basic functional group, an acid addition salt can be obtained by bringing the neutral form of the compound into contact with a sufficient amount of acid in a pure solution or a suitable inert solvent.

Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

In addition to the salt form, the compound provided herein also exists in prodrug form. The prodrug of the compound described herein is the compound that readily undergoes chemical change under physiological condition to be converted into the compound disclosed herein. Additionally, the prodrug can be converted to the compound disclosed herein by a chemical or biochemical method in vivo environment.

Certain compounds disclosed herein can exist in an unsolvated form or a solvated form, including a hydrated form. Generally, the solvated form is equivalent to the unsolvated form, and both are encompassed within the scope disclosed herein.

The compound disclosed herein may be present in a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope disclosed herein. The substituent such as alkyl may have an additional asymmetric carbon atom. All these isomers and mixtures thereof are encompassed within the scope disclosed herein.

Unless otherwise specified, the term "enantiomer" or "optical isomer" refers to stereoisomers that are in a mirrored relationship with each other.

Unless otherwise specified, the term "cis-trans isomer" or "geometric isomer" is produced by the inability of a double bond or a single bond between ring-forming carbon atoms to rotate freely.

Unless otherwise specified, the term "diastereomer" refers to a stereoisomer in which two or more chiral centers of are contained in a molecule and is in a non-mirrored relationship between molecules.

Unless otherwise specified, "(+)" means dextroisomer, "(−)" means levoisomer, and "(±)" means racemate.

Unless otherwise specified, a wedged solid bond (  ) and a wedged dashed bond (  ) indicate the absolute configuration of a stereocenter; a straight solid bond (  ) and a straight dashed bond (  ) indicate the relative configuration of a stereocenter; a wavy line (  ) indicates a wedged solid bond (  ) or a wedged dashed bond (  ); or a wavy line (  ) indicates a straight solid bond (  ) and a straight dashed bond (  ).

The compounds disclosed herein may be present in a particular form. Unless otherwise specified, the terms "tautomer" or "tautomeric form" means that different functional groups are in dynamic equilibrium at room temperature and can be rapidly converted into each other. If tautomers are possible (as in solution), a chemical equilibrium of tautomers can be achieved. For example, proton tautomers (also known as prototropic tautomers) include interconversions by proton transfer, such as keto-enol isomerization and imine-enamine isomerization. Valence tautomers include interconversions by recombination of some bonding electrons. A specific example of keto-enol tautomerization is interconversion between two tautomers pentane-2,4-dione and 4-hydroxypent-3-en-2-one.

Unless otherwise specified, the term "enriched in one isomer", "isomer enriched", "enriched in one enantiomer" or "enantiomeric enriched" means that the content of one isomer or enantiomer is less than 100%, and the content of the isomer or enantiomer is 60% or more, or 70% or more, or 80% or more, or 90% or more, or 95% or more, or 96% or more, or 97% or more, 98% or more, 99% or more, 99.5% or more, 99.6% or more, 99.7% or more, 99.8% or more, or 99.9% or more.

Unless otherwise specified, the term "isomer excess" or "enantiomeric excess" refers to the difference between the relative percentages of two isomers or two enantiomers. For example, if one isomer or enantiomer is present in an amount of 90% and the other isomer or enantiomer is present in an amount of 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compounds disclosed herein may contain an unnatural proportion of atomic isotopes at one or more of the atoms that make up the compounds. For example, a compound may be labeled with a radioisotope such as tritium ($^3$H), iodine-125 ($^{125}$I) or C-14 ($^{14}$C). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

The term "pharmaceutically acceptable carrier" refers to any formulation or carrier medium that is capable of delivering an effective amount of an active substance disclosed herein, which does not interfere with the biological activity of an active substance, and has no toxic side effects to the host or patient. Representative carriers include water, oil, vegetables, minerals, cream bases, lotion bases, ointment bases and the like. These bases include suspending agents, tackifiers, transdermal enhancers, etc. Their formulations are well known to those skilled in cosmetic or topical pharmaceutical arts.

The term "excipient" generally refers to the carrier, diluent and/or vehicle required to formulate an effective pharmaceutical composition.

The term "effective amount" or "therapeutically effective amount" with respect to a pharmaceutically or pharmacologically active agent refers to a sufficient amount of a drug or agent that is non-toxic but that can achieve the desired effect. For oral dosage forms in the present disclosure, an "effective amount" of an active substance in a composition refers to the amount required to achieve the desired effect when it is used in combination with another active substance in the composition. The determination of the effective amount will vary from person to person, depending on the age and general condition of the recipient, and also on the particular active substance. A suitable effective amount in a case can be determined by one skilled in the art based on routine experimentation.

The term "active ingredient", "therapeutic agent", "active substance" or "active agent" refers to a chemical entity that is effective in treating a target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is oxo (i.e. =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a substituent can be linked to more than one atoms on a ring, such substituent can be bonded to any atom on the ring. For example, a moiety

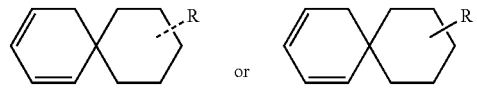

indicates that the substituent R can be positioned at any position on the cyclohexyl group or cyclohexadiene.

When an enumerative substituent does not indicate through which atom it is linked to the substituted group, such substituent can be bonded through any of its atoms. For example, a pyridyl group as a substituent may be linked to the substituted group through any one of carbon atoms on the pyridine ring. When an enumerative linking group does not indicate its linking direction, its linking direction is arbitrary. For example, when the linking group L in

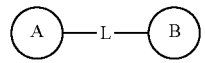

is -M-W—, the -M-W— can be linked to the ring A and the ring B in the same direction as the reading order from left to right to constitute

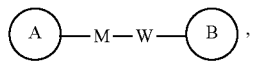

or can be linked to the ring A and the ring B in the reverse direction as the reading order from left to right to constitute

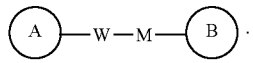

A combination of the linking groups, substituents and/or variants thereof is allowed only when such combination can result in a stable compound.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$ N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidyl; on the other hand, the term "5-7 membered heterocycloalkyl ring" includes pyridyl and piperidyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from the group consisting of N, O and S, wherein any of the above heterocycle can be fused to a benzene ring to form a bicyclic ring. Nitrogen and sulfur heteroatoms can optionally be oxidized (i.e., NO and S(O)$_p$, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from the group consisting of N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)$_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuryl, benzomercaptofuryl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuryl, furyl, furazanyl, imidazolidinyl, imidazolinyl, imidazolyl, 1H-indazolyl, indolenyl, indolinyl, indolizinyl, indolyl, 3H-indolyl, isobenzofuryl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1H-1,2,3-triazolyl, 2H-1,2,3-triazolyl, 1H-1,2,4-triazolyl, 4H-1,2,4-triazolyl and xanthenyl. Fused-ring compounds and spiro compounds are also included.

Unless otherwise specified, the term "hydrocarbyl" or the specific term thereof (e.g. alkyl, alkenyl, alkynyl, and aryl, etc.), by itself or as part of another substituent, refers to a linear, branched chain or cyclic hydrocarbon radical or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from the group consisting of $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from the group consisting of $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1, 4-pentadienyl), ethynyl, 1- and 3-propynyl, 3-butynyl, and more higher homologs and isomers.

Unless otherwise specified, the term "heterohydrocarbyl" or the specific term thereof (such as heteroalkyl, heteroalkenyl, heteroalkynyl, and heteroaryl, etc.), by itself or as part of another term, refers to a stable linear, branched or cyclic hydrocarbon group or the combination thereof, which has a specified number of carbon atoms and at least one heteroatom. In some embodiments, the term "heteroalkyl" by itself or in combination with another term refers to a stable linear, or branched hydrocarbon group or the combination thereof, which has a specified number of carbon atoms and at least one heteroatom. In a specific embodiment, a heteroatom is selected from the group consisting of B, O, N and S, wherein nitrogen and sulfur atoms are optionally oxidized and the nitrogen atom is optionally quaternized. The heteroatom or heteroatom group can be located at any interior position of a heterohydrocarbyl group, including the position where the hydrocarbyl group is attached to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, the term "cyclohydrocarbyl", "heterocyclohydrocarbyl" or the specific term thereof (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cyclohydrocarbyl include, but are not limited to, cyclopentyl, cyclohexyl, 1-cyclohexenyl, 3-cyclohexenyl, cycloheptyl and the like. Non-limiting examples of heterocyclohydrocarbyl include 1-(1,2,5,6-tetrahydropyridyl), 1-piperidyl, 2-piperidyl, 3-piperidyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl and 2-piperazinyl.

Unless otherwise specified, the term "heterocycloalkyl" by itself or in combination with other term means cyclized "heteroalkyl". In addition, as far as the "heterocycloalkyl" is concerned, the heteroatom may occupy the connection position of the heterocycloalkyl to the rest of the molecule. In some embodiments, the heterocycloalkyl is a 4- to 6-membered heterocycloalkyl; in other embodiments, the heterocycloalkyl is a 5- to 6-membered heterocycloalkyl. Examples of heterocycloalkyl include, but are not limited to, azetidinyl, oxetanyl, thietanyl, pyrrolidinyl, pyrazolidinyl, imidazolidinyl, tetrahydrothienyl, tetrahydrofuranyl, tetrahydropyranyl, piperidinyl, piperazinyl, morpholinyl, dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

Unless otherwise specified, the term "alkyl" refers to a linear or branched saturated hydrocarbon group, can be mono-substituted (e.g. —CH$_2$F) or poly-substituted (e.g. —CF$_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom thereof is saturated. Cycloalkyl can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon double bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo(C$_1$-C$_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and s-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from the group consisting of B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyloxazolyl, isoxazolyl, thiazolyl, furyl, thienyl, pyridyl, pyrimidinyl, benzothiazolyl, purinyl, benzimidazolyl, indolyl, isoquinolinyl, quinoxalinyl, quinolinyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl and 6-quinolinyl. The substituent of any of the above aryl and heteroaryl ring system is selected from the group consisting of the acceptable substituents described below.

Unless otherwise specified, when combined with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxymethyl, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound disclosed herein can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment disclosed herein.

All of the solvents used in the present disclosure are commercially available. The present disclosure employs the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equivalence; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butoxycarbonyl, which is an amino protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyldicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; NFSI represents N-fluoro-N-(phenylsulfonyl)benzenesulfonamide; NCS represents 1-chloropyrrolidine-2,5-dione; $n-Bu_4NF$ represents tetrabutylammonium fluoride; iPrOH represents 2-propanol; mp represents melting point; LDA represents lithium diisopropylamide; FA represents formic acid; and ACN represents acetonitrile.

Compounds are named manually or by ChemDraw® software, and the commercially available compounds use their vendor directory names.

DETAILED DESCRIPTION

The present disclosure is described in detail below by means of examples. However, it is not intended that these examples have any disadvantageous limitations to the present disclosure. The present disclosure has been described in detail herein, and the embodiments are also disclosed herein. It will be apparent to those skilled in the art that various changes and modifications may be made to the embodiments disclosed herein without departing from the spirit and scope disclosed herein.

Example 1

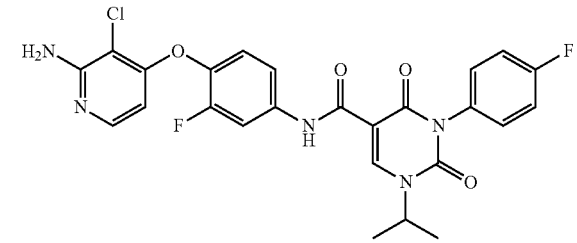 [SMILES: CC(C)n1cc(C(=O)Nc2ccc(Oc3ccnc(N)c3Cl)c(F)c2)c(=O)n(-c2ccc(F)cc2)c1=O]

1a

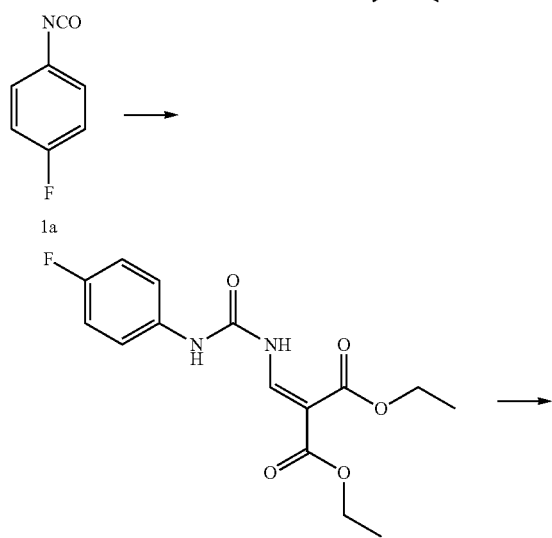

1b

1c

1d

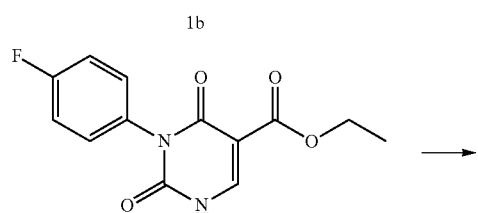

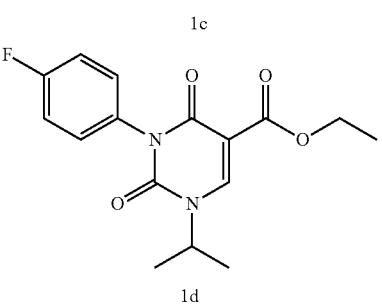

1e

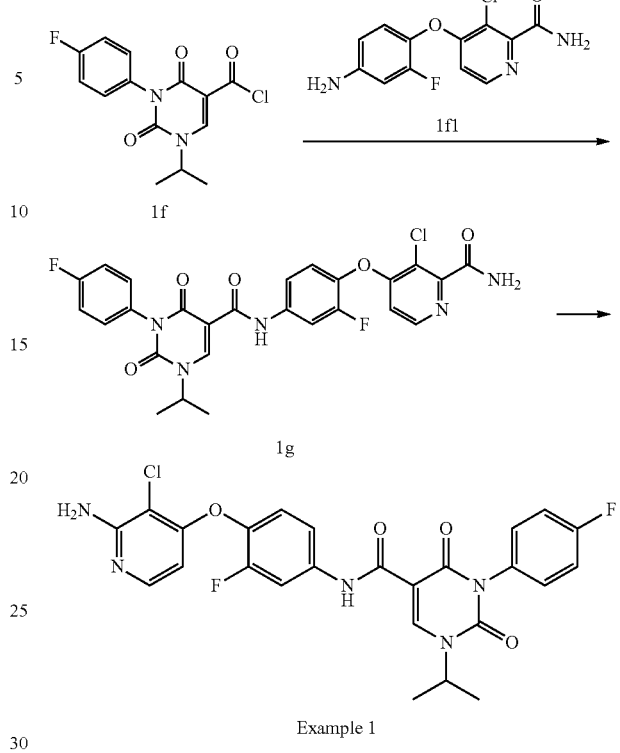

Example 1

Step 1

2.3 g of 1a (16.77 mmol, 1.89 mL, 1.05 eq) was dissolved in 20 mL of 1,2-dichloroethane at room temperature, to which 3 g of diethyl aminomethylenemalonate (16.03 mmol, 1.00 eq) and 2.49 g of diisopropylethylamine (19.23 mmol, 3.35 mL, 1.2 eq) were then added. The reaction solution was stirred at 100° C. for 12 hours. After the reaction was completed, the mixture was filtered, and the resulting filter cake was the reaction product 1b, which can be directly used in the next step without purification. $^1$H NMR (400 MHz, DMSO-$d_6$) δ ppm 1.26 (dt, J=12.05, 7.09 Hz, 6H) 4.16 (q, J=7.15 Hz, 2H) 4.25 (q, J=7.03 Hz, 2H) 7.15-7.24 (m, 2H) 7.47-7.56 (m, 2H) 8.47 (d, J=12.55 Hz, 1H) 10.42 (s, 1H) 10.58 (d, J=12.55 Hz, 1H).

Step 2

3.4 g of 1b (10.26 mmol, 1 eq) was dissolved in 15 mL of ethanol at room temperature, to which 0.8 g of sodium ethoxide was then added with stirring. The reaction solution was stirred at room temperature for 0.5 hour. After the reaction was completed, the mixture was filtered, and the resulting filter cake was the product 1c. $^1$H NMR (400 MHz, DMSO-$d_6$) δ ppm 1.21 (t, J=7.09 Hz, 4H) 4.08 (q, J=7.05 Hz, 2H) 7.05-7.10 (m, 2H) 7.16-7.22 (m, 2H) 8.46 (s, 1H).

Step 3

0.5 g of 1c (1.80 mmol, 1 eq), 0.5 g of potassium carbonate (3.62 mmol, 2.01 eq) and 0.45 g of 2-bromopropane (3.66 mmol, 343.51 μL, 2.04 eq) were added to 5 mL of DMF at room temperature. After nitrogen protection, the reaction solution was stirred at 70° C. for 12 hours. After the reaction was completed, the reaction solution was diluted with 30 mL of water, and then extracted with 30 mL of ethyl acetate. The obtained organic phase was washed with 10 mL of saturated brine, dried over anhydrous sodium sulfate, and rotary evaporated to remove the solvent. The residue was purified by column chromatography (petroleum ether/ethyl acetate=3/1) to afford 1d. $^1$H NMR (400 MHz, DMSO-d$_6$) δ ppm 1.25 (t, J=7.09 Hz, 3H) 1.37 (d, J=6.72 Hz, 6H) 4.22 (q, J=7.09 Hz, 2H) 4.64-4.75 (m, 1H) 7.26-7.37 (m, 4H) 8.45 (s, 1H).

Step 4

0.46 g 1d (1.44 mmol, 1 eq) was dissolved in 9 mL MeOH, which was then added to a solution of 0.075 g lithium hydroxide monohydrate (1.79 mmol, 1.24 eq) in 3 mL water. The reaction solution was stirred at 25° C. for 0.5 hour. After the reaction was completed, the reaction solution was concentrated to remove most of the methanol. The reaction solution was then diluted with 20 mL of water and extracted with ethyl acetate (30 mL×1). The organic phase was discarded. The aqueous phase was adjusted to pH of 3 and then extracted with ethyl acetate (30 mL×2). The combined organic phase was washed with 10 mL of saturated brine, and dried over anhydrous sodium sulfate. The solvent of the dried organic phase was removed by rotary evaporation to afford 1e. $^1$H NMR (400 MHz, DMSO-d$_6$) δ ppm 1.39 (d, J=6.78 Hz, 6H) 4.73 (quin, J=6.74 Hz, 1H) 7.03-7.51 (m, 5H) 8.39-8.77 (m, 1H) 12.64 (br s, 1H).

Step 5

80 mg of 1e (259.93 μmol, 1 eq) was dissolved in 5 mL of tetrahydrofuran. To the mixture was added dropwise 2 μL of DMF followed by 23 μL of oxalyl chloride with stirring. The reaction solution was stirred at 20° C. for 0.5 hour. After the reaction was completed, the reaction solution was concentrated to remove the solvent to afford a crude oily product 1f, which was used directly in the next step without purification.

Step 6

50 mg of 1f1 (177.51 μmol, 1 eq) was dissolved in 5 mL of tetrahydrofuran, to which 60 μL of diisopropylethylamine (2.0 eq) was then added dropwise. To the above solution was added 90 mg of 1f product dissolved in 5 mL of tetrahydrofuran. The reaction solution was stirred at 20° C. for 0.5 h. After the reaction was completed, the reaction solution was concentrated to remove the solvent, diluted with 20 mL of water, and extracted with ethyl acetate (30 mL×1). The organic phase was washed with saturated ammonium chloride solution (40 mL×1), saturated sodium carbonate solution (40 mL×1) and saturated brine. The washed organic phase was dried over anhydrous sodium sulfate, and rotary evaporated to remove the solvent to afford 1g, which was used directly in the next step without purification. LCMS M+1: 566.0.

Step 7

150 mg of 1g (269.82 μmol, 1 eq) was dissolved in a mixed solvent of 4 mL of acetonitrile and 4 mL of ethyl acetate, to which 2 mL of water was then added. To the mixture was added 104.29 mg of iodobenzene diacetate (323.79 μmol, 1.2 eq) with stirring. The reaction solution was stirred at 20° C. for 1 hour. After the reaction was completed, the mixture was isolated by preparative chromatography (Column type: Luna C18 150*25 mm*5 μm; mobile phase: [A: water (0.225% FA), B: ACN]; B %: 33%-57%, 10 min) to afford the product of example 1. $^1$H NMR (400 MHz, DMSO-d$_6$) δ ppm 1.43 (d, J=6.78 Hz, 6H) 4.73-4.81 (m, 1H) 5.94 (d, J=5.40 Hz, 1H) 6.43 (s, 2H) 7.29-7.39 (m, 3H) 7.39-7.39 (m, 1H) 7.40-7.46 (m, 2H) 7.48 (br d, J=8.28 Hz, 1H) 7.76 (d, J=5.65 Hz, 1H) 7.96 (dd, J=12.92, 2.38 Hz, 1H) 8.67 (s, 1H) 11.01 (s, 1H).

Example 2

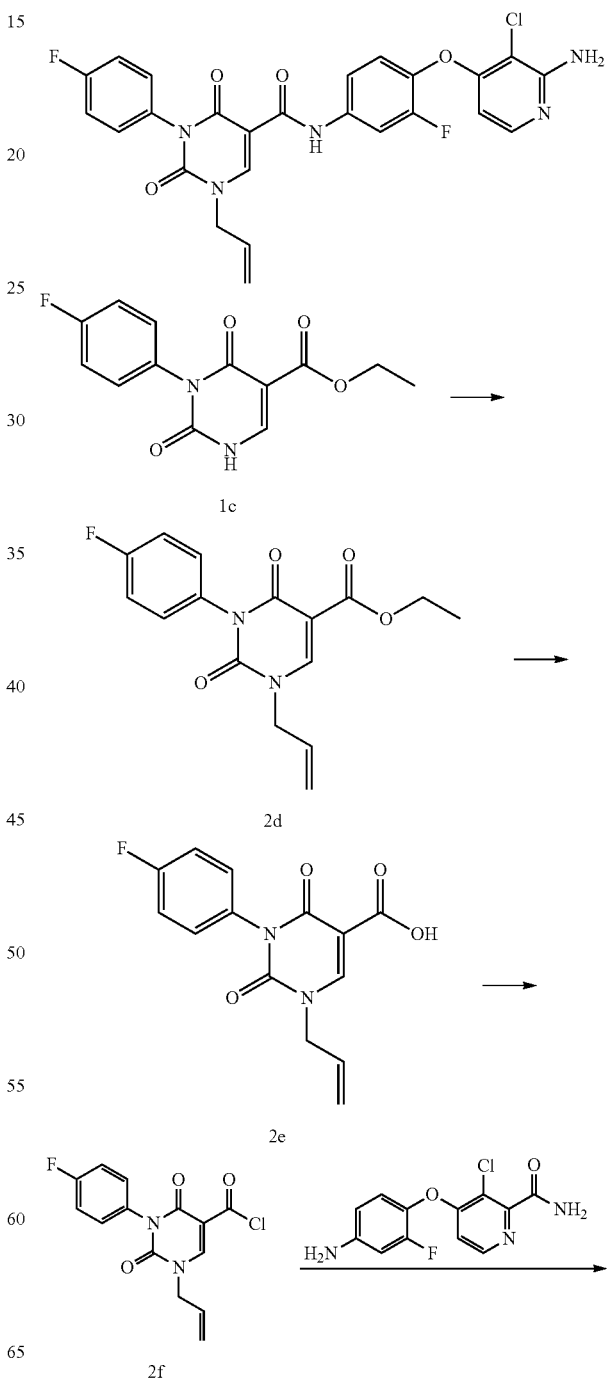

-continued

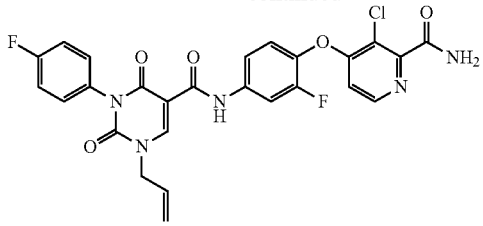

2g

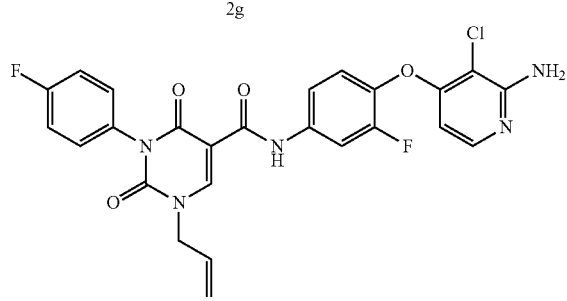

Example 2

Step 1

0.3 g of 1c (1.08 mmol, 1 eq), 0.3 g of potassium carbonate (2.17 mmol, 2.01 eq) and 0.26 g of 3-bromopropene (2.15 mmol, 1.99 eq) were added to 5 mL of DMF at room temperature. After nitrogen protection, the reaction solution was stirred at 70° C. for 2 hours. After the reaction was completed, the reaction solution was diluted with 50 mL of water, and then extracted with 60 mL of ethyl acetate. The obtained organic phase was washed with 50 mL of saturated brine, and then dried over anhydrous sodium sulfate. The solvent of the dried organic phase was removed by rotary evaporation to afford 2d. $^1$H NMR (400 MHz, DMSO-$d_6$) δ ppm 1.25 (t, J=7.09 Hz, 3H) 4.21 (q, J=7.15 Hz, 2H) 4.52 (br d, J=5.40 Hz, 2H) 5.21-5.36 (m, 2H) 5.88-6.01 (m, 1H) 7.29-7.34 (m, 4H) 8.59 (s, 1H).

Step 2

0.27 g 2d (848.26 μmol, 1 eq) was dissolved in 6 mL of ethanol, which was then added to a solution of 0.096 g of potassium hydroxide (1.79 mmol, 1.24 eq) in 2 mL of water. The reaction solution was stirred at 20° C. for 1 hour. After the reaction was completed, the reaction solution was concentrated to remove most of the ethanol. The reaction solution was then diluted with 20 mL of water and extracted with ethyl acetate (30 mL×1). The organic phase was discarded. The aqueous phase was adjusted to pH of 3, and then extracted with ethyl acetate (30 mL×2). The organic phases were combined, washed with 40 mL of saturated brine, and then dried over anhydrous sodium sulfate. The solvent of the dried organic phase was removed by rotary evaporation to afford 2e. $^1$H NMR (400 MHz, DMSO-$d_6$) δ ppm 4.57 (d, J=5.77 Hz, 1H) 4.91 (d, J=13.05 Hz, 1H) 5.10-5.43 (m, 2H) 5.82-6.06 (m, 1H) 6.96-7.12 (m, 1H) 7.25-7.41 (m, 2H) 7.53-7.62 (m, 1H) 8.63 (s, 1H).

Step 3

110 mg 2e (378.99 μmol, 1 eq) was dissolved in 5 mL of tetrahydrofuran. To the mixture was added dropwise 3 μL of DMF followed by 40 μL of (COCl)$_2$ with stirring. The reaction solution was stirred at 20° C. for 0.5 hour. After the reaction was completed, the reaction solution was concentrated to remove the solvent to afford an oily crude product 2f, which was used in the next step without purification.

Step 4

100 mg of 1f1 (355.03 μmol, 0.9 eq) was dissolved in 5 mL of tetrahydrofuran, to which 135 μL of diisopropylethylamine (2.0 eq) was then added dropwise. 120 mg of 2f (388.74 μmol, 1 eq) was dissolved in 10 mL of tetrahydrofuran, which was then added dropwise to the above solution. The reaction solution was stirred at 20° C. for 0.5 hour. After the reaction was completed, the reaction solution was concentrated to remove the solvent. The reaction solution was then diluted with 20 mL of water and extracted with ethyl acetate (30 mL×1). The organic phase was washed with saturated ammonium chloride solution (40 mL×1), saturated sodium carbonate solution (40 mL×1) and saturated brine, dried over anhydrous sodium sulfate, and concentrated. The residue was purified by preparative TLC to afford 2g.

Step 5

30 mg of 2g (44.44 μmol, 1 eq) was dissolved in a mixed solvent of 3 mL of acetonitrile and 3 mL of ethyl acetate, to which 1 mL of water was then added. To the mixture was added 30 mg of iodobenzene diacetate (93.14 μmol, 2.10 eq) with stirring. The reaction solution was stirred at 20° C. for 1 hour. After the reaction was completed, the reaction solution was isolated by preparative chromatography (Column type: Luna C18 150*25 mm*5 μm; mobile phase: [A: water (0.225% FA), B: ACN]; B %: 35%-56%, 10 min) to afford the product of Example 2. $^1$H NMR (400 MHz, DMSO-$d_6$) δ ppm 4.62 (br s, 2H) 5.25-5.43 (m, 2H) 5.90-6.04 (m, 2H) 6.42 (br d, J=1.51 Hz, 2H) 7.28-7.50 (m, 6H) 7.73-7.79 (m, 1H) 7.90-7.98 (m, 1H) 8.37 (br s, 1H) 8.80 (d, J=4.27 Hz, 1H) 10.99 (br d, J=3.01 Hz, 1H).

Example 3

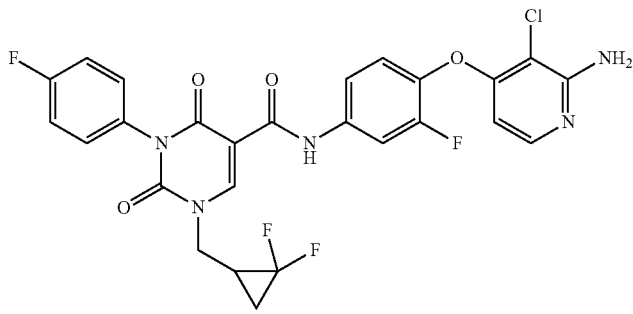

-continued

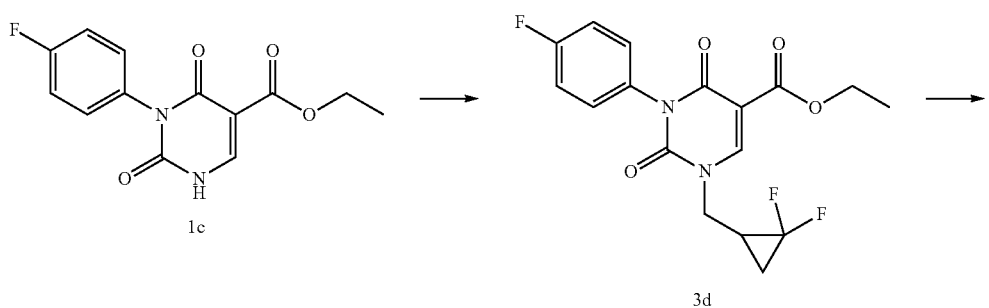

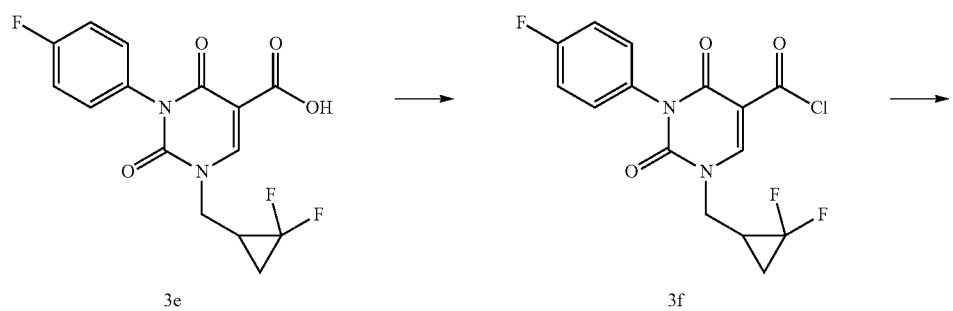

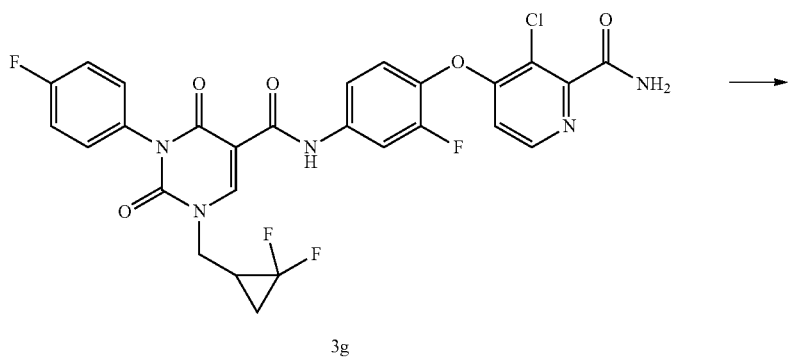

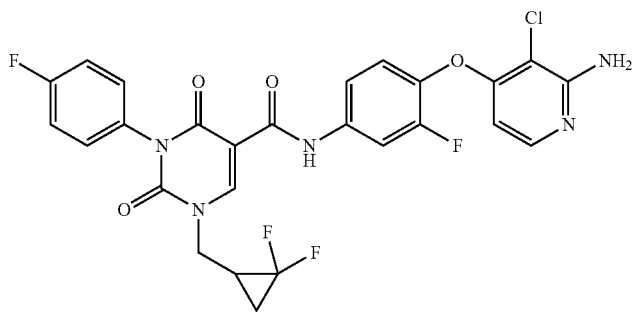

Example 3

Step 1: 3d was obtained by the method as described for intermediate 1d. LCMS (ESI) m/z: 367.1 (M+1).
Step 2: 3e was obtained by the method as described for intermediate 1e.
Step 3: 3f was obtained by the method as described for intermediate 1f.
Step 4: 3g was obtained by the method as described for intermediate 1g. LCMS (ESI) m/z: 604.0 (M+1).

Step 5: The product of Example 3 was obtained by the method as described for the product of Example 1. $^1$H NMR (400 MHz, DMSO-$d_6$) δ ppm 1.502-1.816 (m, 2H) 2.079 (s, 1H) 2.241 (br dd, J=11.42, 5.90 Hz, 1H) 4.141 (br d, J=7.03 Hz, 2H) 5.941 (d, J=5.65 Hz, 1H) 6.411 (s, 2H) 7.266-7.534 (m, 5H) 7.284-7.518 (m, 1H) 7.760 (d, J=5.65 Hz, 1H) 7.956 (dd, J=12.86, 2.20 Hz, 1H) 8.861 (s, 1H) 10.969 (s, 1H).

Example 4

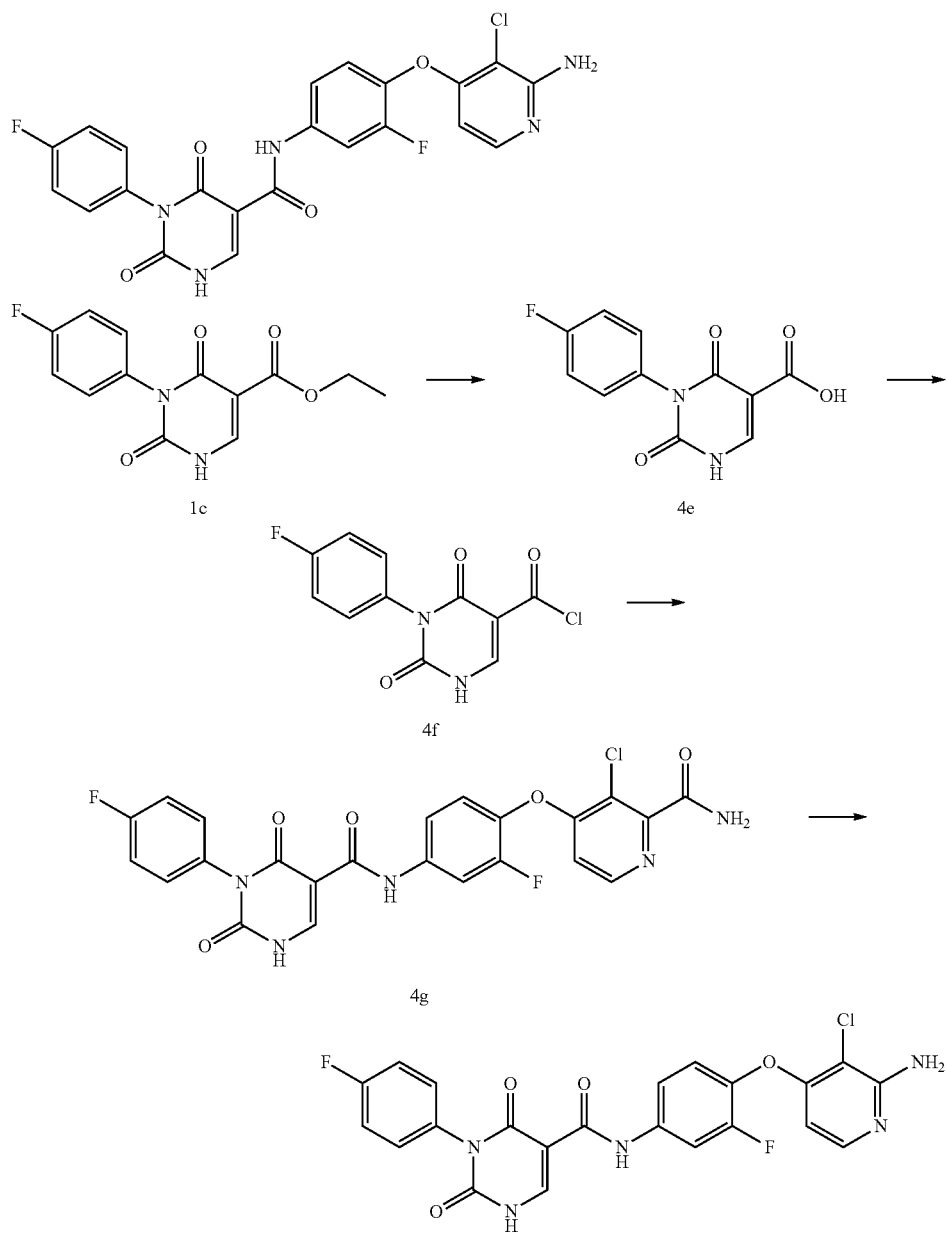

Example 4

Step 1

0.2 g of 1c (848.26 μmol, 1 eq) was dissolved in 6 mL of ethanol, which was then added to a solution of 80 mg of potassium hydroxide (1.79 mmol, 1.24 eq) in 2 mL of water. The reaction solution was stirred at 25° C. for 12 hours. After the reaction was completed, the reaction solution was concentrated to remove most of the ethanol. The reaction solution was then diluted with 20 mL of water and extracted with ethyl acetate (30 mL×1). The organic phase was discarded. The aqueous phase was adjusted to pH of 3, and then extracted with ethyl acetate (40 mL×1). The organic phases were combined, washed with 40 mL of saturated brine, and then dried over anhydrous sodium sulfate. The solvent of the dried organic phase was removed by rotary evaporation to afford 4e, which was used directly in the next step.

Step 2

130 mg of 4e (516.33 μmol, 1 eq) was dissolved in 5 mL of tetrahydrofuran. To the mixture was added dropwise 3 μL of DMF followed by 50 μL of oxalyl chloride with stirring. The reaction solution was stirred at 20° C. for 0.5 hour. After the reaction was completed, the reaction solution was concentrated to remove the solvent to afford the crude product 4f, which was used in the next step without purification.

Step 3

140 mg of 1f1 (497.04 μmol, 1.03 eq) was dissolved in 5 mL of tetrahydrofuran, to which 170 μL of diisopropylethylamine (2.0 eq) was then added dropwise. 130 mg of 4f (388.74 μmol, 1 eq) was dissolved in 10 mL of tetrahydrofuran, which was then added dropwise to the above solution. The reaction solution was stirred at 20° C. for 0.5 hour. After the reaction was completed, the reaction solution was concentrated to remove the solvent. The reaction solution was then diluted with 20 mL of water and extracted with ethyl acetate (30 mL×1). The organic phases were combined, washed with saturated ammonium chloride solution (40 mL×1), saturated sodium carbonate solution (40 mL×1) and saturated brine, and dried over anhydrous sodium sulfate. The dried organic phase was concentrated and then purified by preparative TLC to afford 4g. $^1$H NMR (400 MHz, CD$_3$OD) δ ppm 6.80-7.09 (m, 1H) 7.19-7.49 (m, 9H) 7.79-8.07 (m, 1H) 8.32 (d, J=5.52 Hz, 1H) 8.42 (s, 1H) 8.49-8.80 (m, 1H).

Step 4

50 mg of 4g (97.31 μmol, 1 eq) was dissolved in a mixed solvent of 3 mL of acetonitrile and 3 mL of ethyl acetate, to which 1 mL of water was then added. To the mixture was added 63 mg of iodobenzene diacetate (195.59 μmol, 2.01 eq) with stirring. The reaction solution was stirred at 20° C. for 1 hour. After the reaction was completed, the reaction solution was isolated by preparative chromatography (Column type: PhenomenexSynergi C18 150*25 mm*10 μm; mobile phase: [A: water (0.225% FA), B: ACN]; B %: 17%-47%, 10 min) to afford the product of Example 4. $^1$H NMR (400 MHz, DMSO-d$_6$) δ ppm 5.93 (d, J=5.65 Hz, 1H) 6.41 (s, 2H) 7.26-7.46 (m, 7H) 7.75 (d, J=5.77 Hz, 1H) 7.95 (dd, J=12.99, 2.45 Hz, 1H) 8.47 (s, 1H) 11.07 (s, 1H).

Example 5

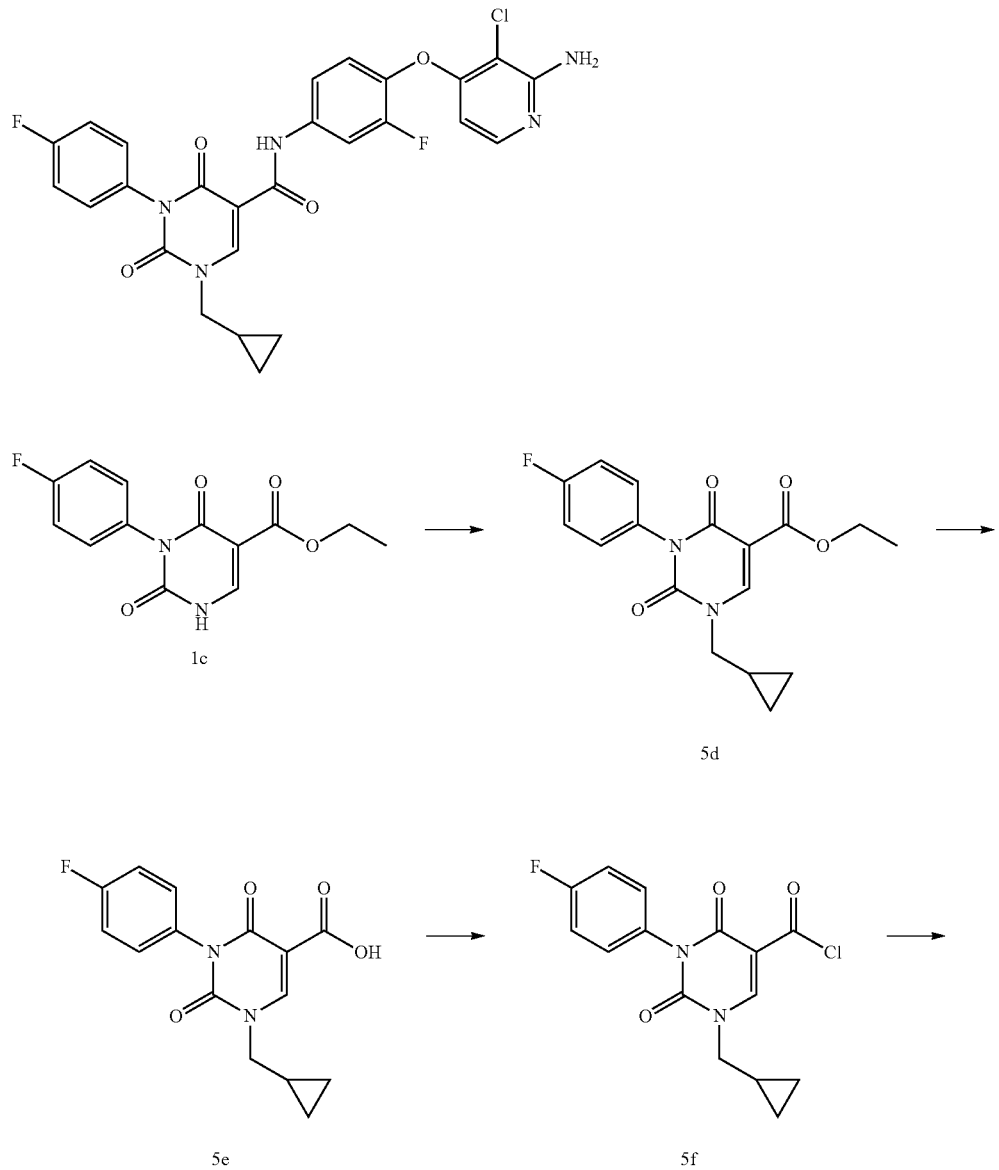

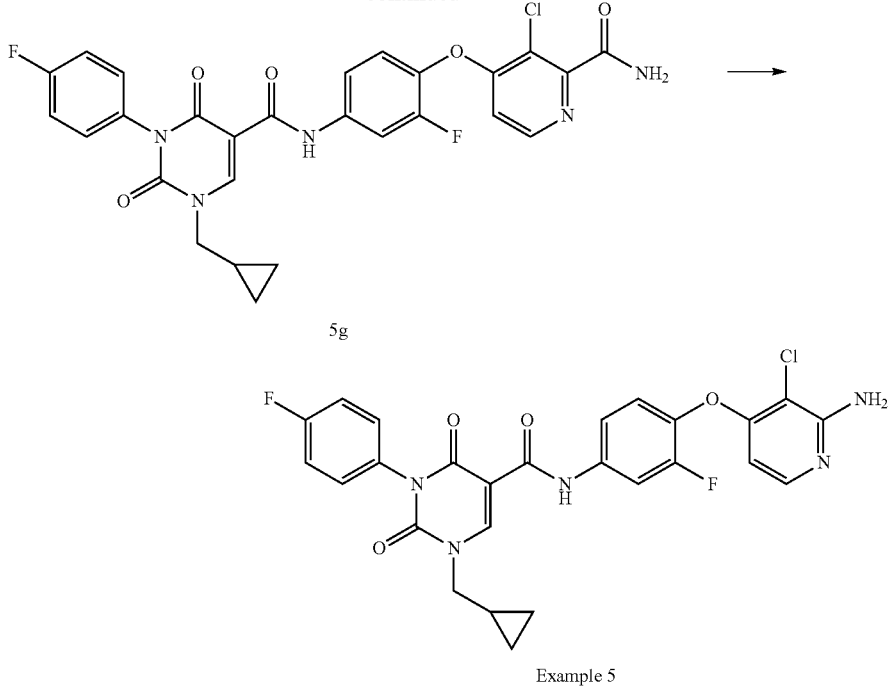

Example 5

Step 1

0.5 g of 1c (1.8 mmol, 1 eq), 0.5 g of potassium carbonate (3.62 mmol, 2.01 eq) and 0.49 g of cyclopropyl methyl bromide (3.59 mmol, 1.99 eq) were added to 10 mL of DMF at room temperature. After nitrogen protection, the reaction solution was stirred at 70° C. for 12 hours. After the reaction was completed, the reaction solution was diluted with 40 mL of water, and then extracted with 60 mL of ethyl acetate. The obtained organic phase was washed with 50 mL of saturated brine and dried over anhydrous sodium sulfate. The dried organic phase was rotary evaporated to remove the solvent to afford 5d. $^1$H NMR (400 MHz, DMSO-$d_6$) δ ppm 0.23-0.31 (m, 2H) 0.37-0.46 (m, 2H) 1.03-1.10 (m, 1H) 1.13 (t, J=7.09 Hz, 3H) 2.77 (s, 9H) 3.64 (d, J=7.09 Hz, 2H) 4.09 (q, J=7.13 Hz, 2H) 7.15-7.21 (m, 4H) 8.56 (s, 1H).

Step 2

0.85 g of 5d (2.56 mmol, 1 eq) was dissolved in 6 mL of ethanol, which was then added to a solution of 0.22 g of lithium hydroxide (1.79 mmol, 1.24 eq) in 2 mL of water. The reaction solution was stirred at 20° C. for 1 hour. After the reaction was completed, the reaction solution was concentrated to remove most of the ethanol. The reaction solution was then diluted with 30 mL of water, and extracted with ethyl acetate (30 mL×1). The aqueous phase was adjusted to pH of 3, and extracted with ethyl acetate (30 mL×2). The organic phases were combined, washed with 40 mL of saturated brine, and dried over anhydrous sodium sulfate. The dried organic phase was rotary evaporated to remove the solvent to afford 5e. $^1$H NMR (400 MHz, DMSO-$d_6$) δ ppm 0.37-0.45 (m, 2H) 0.51-0.56 (m, 2H) 1.15-1.29 (m, 1H) 3.80 (d, J=7.15 Hz, 2H) 7.30-7.42 (m, 4H) 8.72-8.96 (m, 1H) 12.63 (br d, J=1.51 Hz, 1H).

Step 3

300 mg of 5e (884.9 μmol, 1 eq) was dissolved in 10 mL of tetrahydrofuran. To the mixture was added dropwise 3 μL of DMF followed by 100 μL of oxalyl chloride with stirring. The reaction solution was stirred at 20° C. for 0.5 hour. After the reaction was completed, the reaction solution was concentrated to remove the solvent to afford the crude product 5f, which was used in the next step without purification.

Step 4

280 mg of 1f1 (994.07 μmol, 1.13 eq) was dissolved in 10 mL of tetrahydrofuran, to which 310 μL of diisopropylethylamine (2.0 eq) was then added dropwise. 285 mg of 5f (883.1 μmol, 1 eq) was dissolved in 10 mL of THF, which was then added dropwise to the above solution. The reaction solution was stirred at 20° C. for 0.5 hour. After the reaction was completed, the reaction solution was concentrated to remove the solvent. The reaction solution was then diluted with 50 mL of water, and extracted with ethyl acetate (80 mL×1). The organic phase was washed with saturated ammonium chloride solution (40 mL×1), saturated sodium carbonate solution (40 mL×1) and saturated brine, and then dried over anhydrous sodium sulfate to afford 5g. $^1$H NMR (400 MHz, DMSO-$d_6$) δ ppm 0.20 (q, J=4.65 Hz, 2H) 0.30-0.35 (m, 2H) 1.01 (br s, 1H) 3.62 (d, J=7.21 Hz, 2H) 6.61 (d, J=5.62 Hz, 1H) 7.10-7.23 (m, 5H) 7.30 (dd, J=8.93, 1.22 Hz, 1H) 7.52 (s, 1H) 7.75-7.84 (m, 2H) 8.10 (d, J=5.62 Hz, 1H) 8.67 (s, 1H) 10.80 (s, 1H).

Step 5

500 mg of 5g (880.4 μmol, 1 eq) was dissolved in 9 mL of DMF, to which 3 mL of water was then added. To the mixture was added 340 mg of iodobenzene diacetate (1.06 mmol, 1.2 eq) with stirring. The reaction solution was stirred at 20° C. for 3 hours. After the reaction was completed, the reaction solution was isolated by preparative chromatography (Column type: Phenomenex luna C18 250*50 mm*10 μm; mobile phase: [A: water (0.05% of HCl), B: ACN]; B %: 30%-60%, 32 min) to afford the product of Example 5. $^1$H NMR (400 MHz, DMSO-d$_6$) δ ppm 0.40-0.48 (m, 2H) 0.52-0.61 (m, 2H) 1.20-1.31 (m, 1H) 3.86 (d, J=7.15 Hz, 2H) 5.94 (d, J=5.40 Hz, 1H) 6.42 (s, 2H) 7.27-7.51 (m, 6H) 7.76 (d, J=5.65 Hz, 1H) 7.96 (dd, J=12.92, 2.38 Hz, 1H) 8.91 (s, 1H) 11.00 (s, 1H).

Example 6

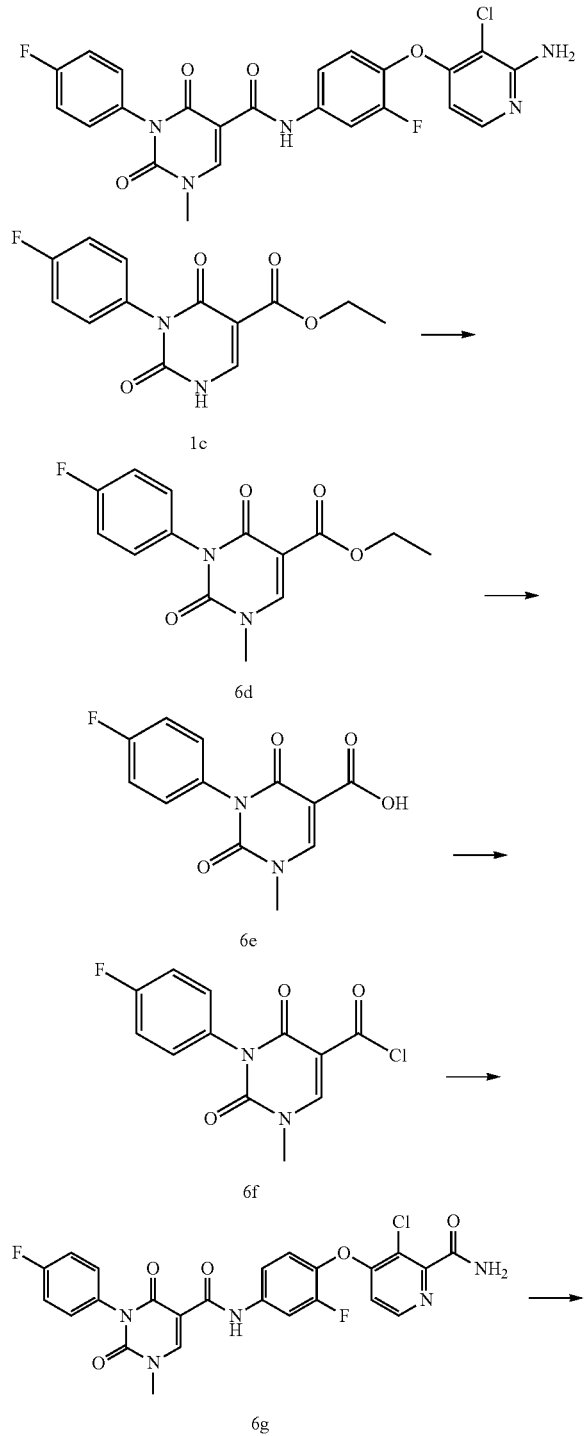

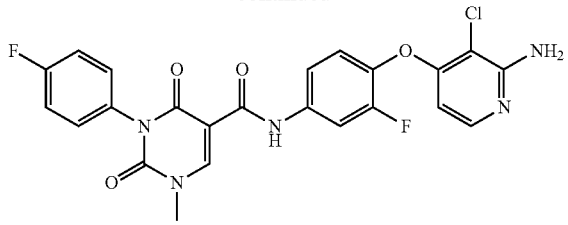 [SMILES: Cn1cc(C(=O)Nc2ccc(Oc3ccnc(N)c3Cl)c(F)c2)c(=O)n(-c2ccc(F)cc2)c1=O]

Example 6

Step 1

0.496 g of 1c (1.54 mmol, 1 eq), 0.43 g of potassium carbonate (3.09 mmol, 2.0 eq) and 0.68 g of iodomethane (4.82 mmol, 3.12 eq) were added to 10 mL of DMF at room temperature. After nitrogen protection, the reaction solution was stirred at 70° C. for 12 hours. After the reaction was completed, the reaction solution was diluted with 30 mL of water, and then extracted with 50 mL of ethyl acetate. The resulting organic phase was washed with 30 mL of saturated brine, dried over anhydrous sodium sulfate, and rotary evaporated to remove the solvent. The obtained residue was subjected to column chromatography to afford 6d. $^1$H NMR (400 MHz, DMSO-d$_6$) δ ppm 1.25 (t, J=7.09 Hz, 3H) 3.44 (s, 3H) 4.21 (q, J=7.15 Hz, 2H) 7.23-7.39 (m, 4H) 8.66 (s, 1H).

Step 2

0.42 g of 6d (1.44 mmol, 1 eq) was dissolved in 6 mL of methanol and 6 mL of tetrahydrofuran, which was then added to a solution of 0.22 g lithium hydroxide (1.79 mmol, 1.24 eq) in 3 mL of water. The reaction solution was stirred at 20° C. for 1 hour. After the reaction was completed, the reaction solution was concentrated to remove most of the ethanol. The reaction solution was then diluted with 20 mL of water, and extracted with ethyl acetate (30 mL×1). The organic phase was discarded. The aqueous phase was adjusted to pH of 3, and then extracted with ethyl acetate (30 mL×2). The organic phases were combined, washed with 40 mL of saturated brine, and dried over anhydrous sodium sulfate. The dried organic phase was rotary evaporated to remove the solvent to afford 6e. $^1$H NMR (400 MHz, DMSO-d$_6$) δ ppm 3.48 (s, 3H) 7.31-7.37 (m, 4H) 8.82 (s, 1H).

Step 3

152 mg of 6e (569.9 μmol, 1 eq) was dissolved in 8 mL of tetrahydrofuran. To the mixture was added dropwise 3 μL of DMF followed by 60 μL of oxalyl chloride with stirring. The reaction solution was stirred at 10° C. for 0.5 hour. After the reaction was completed, the reaction solution was concentrated to remove the solvent to afford the crude product 6f, which was used in the next step without purification.

Step 4

160 mg of 1f1 (569.92 μmol, 1.0 eq) was dissolved in 8 mL of tetrahydrofuran, to which 198 μL of diisopropylethylamine (2.0 eq) was then added dropwise. 6f was dissolved in 10 mL of tetrahydrofuran, which was then added dropwise to the above solution. The reaction solution was stirred at 20° C. for 0.5 hour. After the reaction was completed, the reaction solution was concentrated to remove the solvent. The reaction solution was then diluted with 50 mL of water and extracted with ethyl acetate (80 mL×1). The organic phase was washed with 1N hydrochloric acid (50 mL×1), saturated sodium carbonate solution (30 mL×1) and saturated brine. The washed organic phase was dried over anhydrous sodium sulfate, and concentrated to afford 6g.

Step 5

250 mg of 6g (473.61 µmol, 1 eq) was dissolved in 9 mL of DMF, to which 3 mL of water was then added. To the mixture was added 183 mg of iodobenzene diacetate (568.3 µmol, 1.2 eq) with stirring. The reaction solution was stirred at 15° C. for 1 hour. After the reaction was completed, the reaction solution was isolated by preparative chromatography (Column type: Boston Green ODS 150*30 mm*5 µm; mobile phase: [A: water (0.225% FA), B: ACN]; B %: 27%-54%, 10 min) to afford the product of Example 6. $^1$H NMR (400 MHz, DMSO-$d_6$) δ ppm 3.54 (s, 3H) 5.93 (d, J=5.65 Hz, 1H) 6.42 (s, 2H) 7.27-7.44 (m, 5H) 7.48 (dd, J=8.85, 1.07 Hz, 1H) 7.76 (d, J=5.65 Hz, 1H) 7.95 (dd, J=12.92, 2.38 Hz, 1H) 8.88 (s, 1H) 11.00 (s, 1H).

Example 7

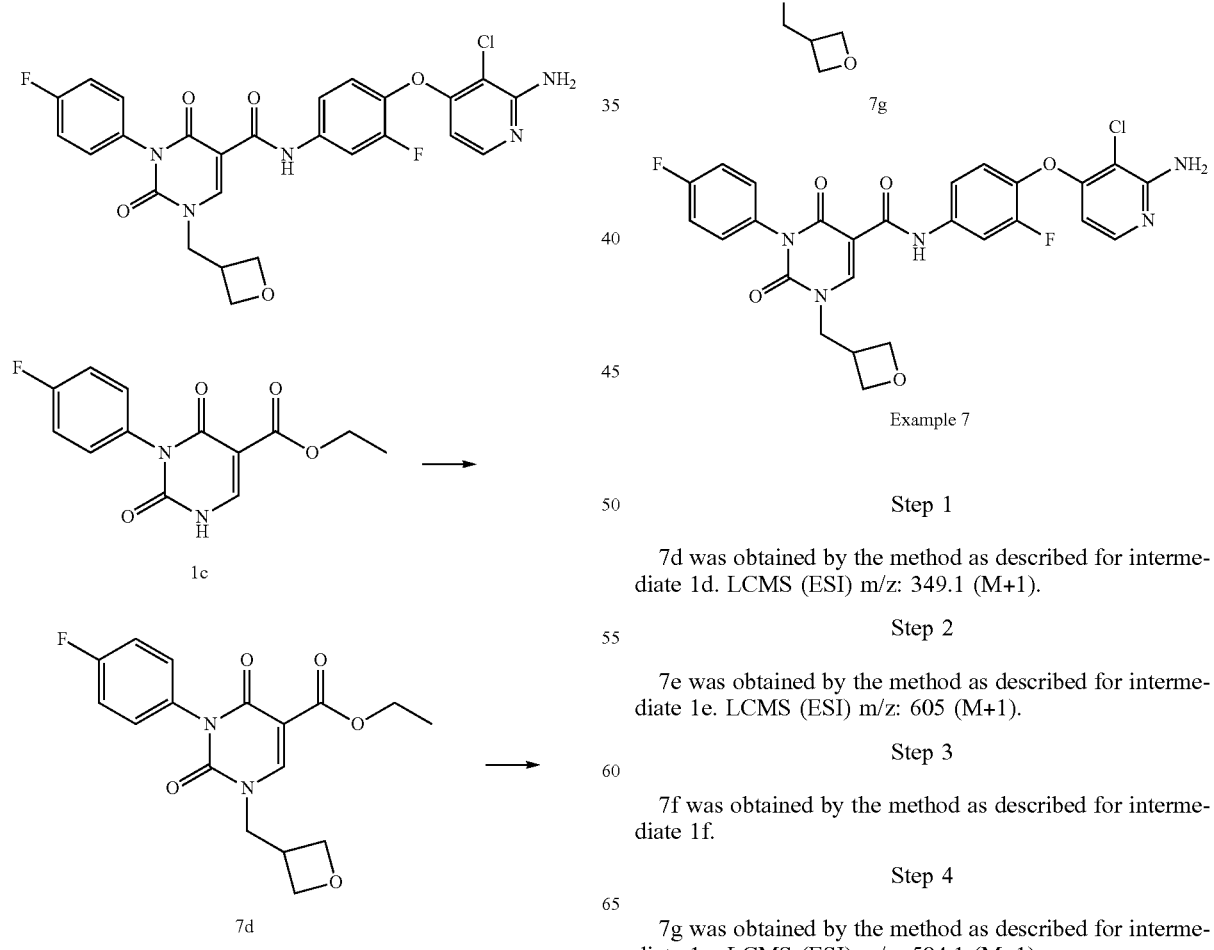

Example 7

Step 1

7d was obtained by the method as described for intermediate 1d. LCMS (ESI) m/z: 349.1 (M+1).

Step 2

7e was obtained by the method as described for intermediate 1e. LCMS (ESI) m/z: 605 (M+1).

Step 3

7f was obtained by the method as described for intermediate 1f.

Step 4

7g was obtained by the method as described for intermediate 1g. LCMS (ESI) m/z: 584.1 (M+1).

Step 5

The product of Example 7 was obtained by the method as described for the product of Example 1. $^1$H NMR (400 MHz, DMSO-$d_6$) δ ppm 2.529 (d, J=1.88 Hz, 1H) 4.292-4.310 (d, J=6.90 Hz, 2H) 4.405-4.437 (t, J=6.27 Hz, 2H) 4.616-4.651 (dd, J=7.91, 6.15 Hz, 2H) 5.928-5.941 (d, J=5.52 Hz, 1H) 6.420 (s, 2H) 7.310-7.400 (m, 5H) 7.407-7.417 (br d, J=10.16 Hz, 1H) 7.749 (d, J=5.65 Hz, 1H) 7.763-7.931 (m, 1H) 8.897 (s, 1H) 10.985 (s, 1H).

Example 8

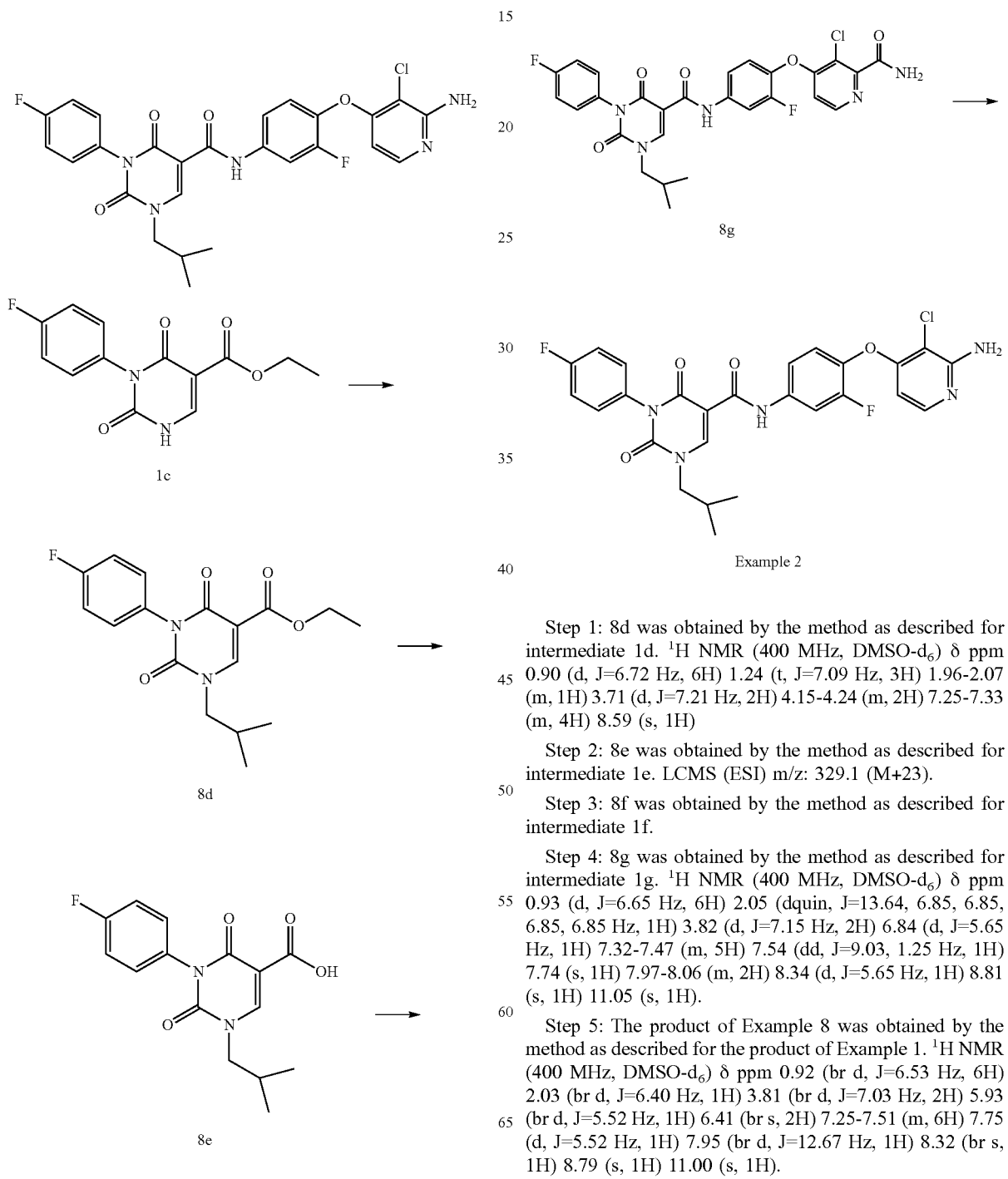

Step 1: 8d was obtained by the method as described for intermediate 1d. $^1$H NMR (400 MHz, DMSO-$d_6$) δ ppm 0.90 (d, J=6.72 Hz, 6H) 1.24 (t, J=7.09 Hz, 3H) 1.96-2.07 (m, 1H) 3.71 (d, J=7.21 Hz, 2H) 4.15-4.24 (m, 2H) 7.25-7.33 (m, 4H) 8.59 (s, 1H)

Step 2: 8e was obtained by the method as described for intermediate 1e. LCMS (ESI) m/z: 329.1 (M+23).

Step 3: 8f was obtained by the method as described for intermediate 1f.

Step 4: 8g was obtained by the method as described for intermediate 1g. $^1$H NMR (400 MHz, DMSO-$d_6$) δ ppm 0.93 (d, J=6.65 Hz, 6H) 2.05 (dquin, J=13.64, 6.85, 6.85, 6.85, 6.85 Hz, 1H) 3.82 (d, J=7.15 Hz, 2H) 6.84 (d, J=5.65 Hz, 1H) 7.32-7.47 (m, 5H) 7.54 (dd, J=9.03, 1.25 Hz, 1H) 7.74 (s, 1H) 7.97-8.06 (m, 2H) 8.34 (d, J=5.65 Hz, 1H) 8.81 (s, 1H) 11.05 (s, 1H).

Step 5: The product of Example 8 was obtained by the method as described for the product of Example 1. $^1$H NMR (400 MHz, DMSO-$d_6$) δ ppm 0.92 (br d, J=6.53 Hz, 6H) 2.03 (br d, J=6.40 Hz, 1H) 3.81 (br d, J=7.03 Hz, 2H) 5.93 (br d, J=5.52 Hz, 1H) 6.41 (br s, 2H) 7.25-7.51 (m, 6H) 7.75 (d, J=5.52 Hz, 1H) 7.95 (br d, J=12.67 Hz, 1H) 8.32 (br s, 1H) 8.79 (s, 1H) 11.00 (s, 1H).

Example 9

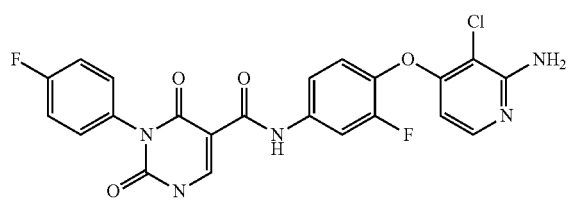
1c

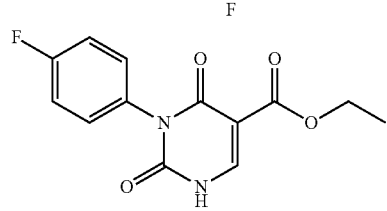
9d

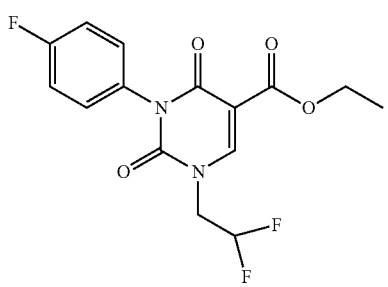
9e

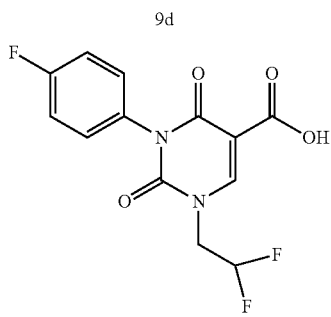
9f

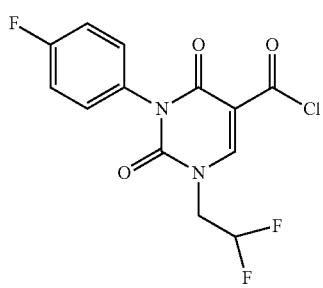

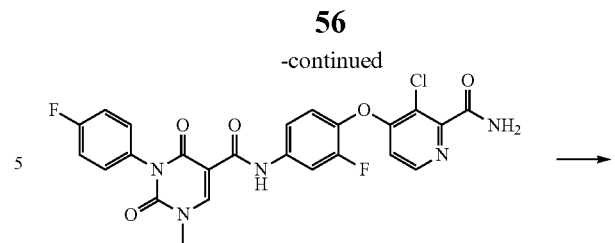
9g

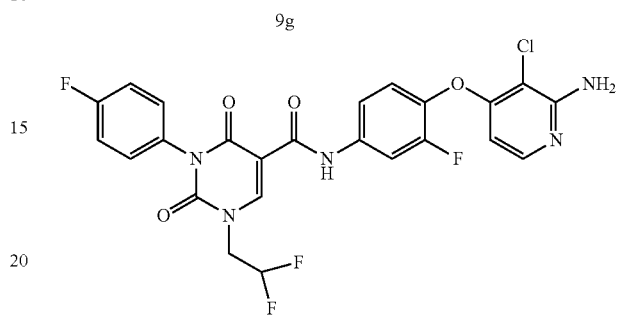
Example 9

Step 1

0.2 g of 1c (0.78 mmol, 1 eq), 0.2 g of potassium carbonate (1.45 mmol, 2.01 eq) and 0.42 g of 1,1-difluoro-2-iodoethane (2.16 mmol, 3.0 eq) were added into 5 mL of DMF at room temperature. After nitrogen protection, the reaction solution was stirred at 70° C. for 12 hours. After the reaction was completed, the reaction solution was diluted with 30 mL of water, and then extracted with 40 mL of ethyl acetate. The obtained organic phase was washed with 50 mL of saturated brine, and then dried over anhydrous sodium sulfate. The dried organic phase was rotary evaporated to remove the solvent to afford 9d.

Step 2

0.2 g of 9d (0.58 mmol, 1 eq) was dissolved in 6 mL of ethanol, which was added to a solution of 0.03 g of lithium hydroxide (0.71 mmol, 1.2 eq) in 2 mL of water. The reaction solution was stirred at 25° C. for 1 hour. After the reaction was completed, the reaction solution was concentrated to remove most of the ethanol. The reaction solution was then diluted with 20 mL of water, and extracted with ethyl acetate (30 mL×1). The organic phase was discarded. The aqueous phase was adjusted to pH of 3, and then extracted with ethyl acetate (30 mL×2). The organic phases were combined, washed with 40 mL of saturated brine, and dried over anhydrous sodium sulfate. The dried organic phase was rotary evaporated to remove the solvent to afford 9e. $^1$H NMR (400 MHz, DMSO-$d_6$) δ ppm 4.36-4.52 (m, 1H) 4.44 (td, J=14.73, 3.18 Hz, 2H) 6.14-6.47 (m, 1H) 7.31-7.40 (m, 4H) 8.75 (s, 1H).

Step 3

100 mg of 9e (31.3 μmol, 1 eq) was dissolved in 10 mL of tetrahydrofuran. To the mixture was added dropwise 1 μL of DMF followed by 30 μL of oxalyl chloride. The reaction solution was stirred at 20° C. for 0.5 hour. After the reaction was completed, the reaction solution was concentrated to remove the solvent to afford the crude product 9f, which was used in the next step without purification.

Step 4

85 mg of 1f1 (994.07 μmol, 1.13 eq) was dissolved in 20 mL of tetrahydrofuran, to which 600 μL of diisopropylethylamine (2.0 eq) was then added dropwise. 100 mg of 9f (300 μmol, 1 eq) was dissolved in 10 mL of THF, which was then added dropwise to the above solution. The reaction solution was stirred at 20° C. for 0.5 hour. After the reaction was completed, the reaction solution was concentrated to remove the solvent. The reaction solution was then diluted with 40 mL of water, and extracted with ethyl acetate (80 mL×1). The organic phase was washed with saturated ammonium chloride solution (40 mL×1), saturated sodium carbonate solution (40 mL×1) and saturated brine, and then dried over anhydrous sodium sulfate to afford a solid 9g.

Step 5

170 mg of 9g (294 μmol, 1 eq) was dissolved in 3 mL of DMF, to which 1 mL of water was then added. To the mixture was added 190 mg of iodobenzene diacetate (590 μmol, 2.0 eq) with stirring. The reaction solution was stirred at 25° C. for 1 hour. After the reaction was completed, the reaction solution was isolated by preparative chromatography (Column type: Phenomenex Synergi C18 150*25 mm*10 μm; mobile phase: [A: water (0.225% FA), B: ACN]; B %: 30%-60%, 10 min) to afford the product of Example 9. $^1$H NMR (400 MHz, DMSO-d$_6$) δ ppm 4.53 (td, J=14.81, 3.26 Hz, 2H) 5.94 (d, J=5.77 Hz, 1H) 6.42 (s, 2H) 7.28-7.52 (m, 7H) 7.76 (d, J=5.65 Hz, 1H) 7.95 (dd, J=12.92, 2.38 Hz, 1H) 8.86 (s, 1H) 10.92 (s, 1H).

Example 10

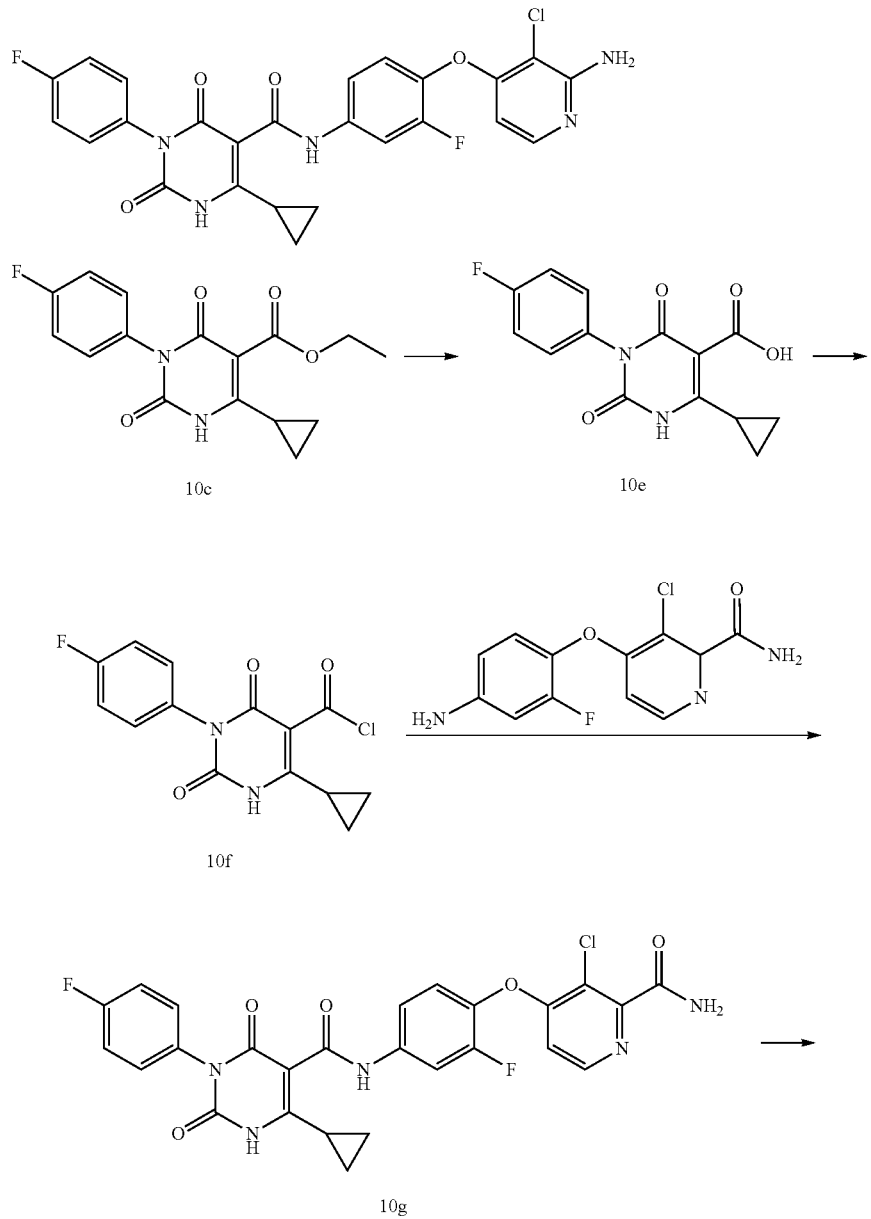

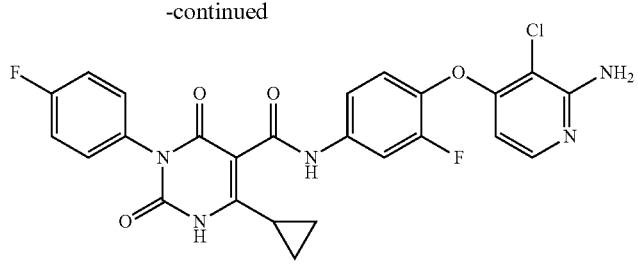

Example 10

Step 1

0.095 g of 10c (298 μmol, 1 eq) was dissolved in 3 mL of ethanol, which was then added to a solution of 0.050 g potassium hydroxide (895 μmol, 3 eq) in 1 mL of water. The reaction solution was stirred at 70° C. for 24 hours. After the reaction was completed, the reaction solution was concentrated to remove most of the ethanol. The reaction solution was then diluted with 15 mL of water, and extracted with ethyl acetate (20 mL×1). The organic phase was discarded. The aqueous phase was adjusted to pH of 3, and then extracted with ethyl acetate (20 mL×2). The organic phases were combined, washed with 30 mL of saturated brine, and dried over anhydrous sodium sulfate. The dried organic phase was rotary evaporated to remove the solvent to afford 10e.

Step 2

85 mg of 10e (268 μmol, 1 eq) was dissolved in 5 mL of tetrahydrofuran. To the mixture was added dropwise 1 μL of DMF followed by 29 μL of oxalyl chloride. The reaction solution was stirred at 20° C. for 0.5 hour. After the reaction was completed, the reaction solution was concentrated to remove the solvent to afford the crude product 10f, which was used in the next step without purification.

Step 3

85 mg of 10f (300 μmol, 1 eq) was dissolved in 5 mL of tetrahydrofuran, to which 100 μL of diisopropylethylamine (2.0 eq) was then added dropwise. 90 mg of 1f product was dissolved in 5 mL of tetrahydrofuran, which was then added dropwise to the above solution. The reaction solution was stirred at 20° C. for 0.5 hour. After the reaction was completed, the reaction solution was concentrated to remove the solvent. The reaction solution was then diluted with 20 mL of water, and extracted with ethyl acetate (30 mL×1). The organic phase was washed with saturated ammonium chloride solution (30 mL×1), saturated sodium carbonate solution (30 mL×1) and saturated brine, and then dried over anhydrous sodium sulfate. The dried organic phase was rotary evaporated to remove the solvent, and then isolated with preparative plate to afford 10g. $^1$H NMR (400 MHz, DMSO-$d_6$) δ ppm 1.06-1.16 (m, 4H) 1.97 (t, J=3.51 Hz, 1H) 7.42-7.54 (m, 4H) 7.56-7.64 (m, 1H) 7.64-7.73 (m, 1H) 7.97-8.05 (m, 2H) 8.11 (s, 2H) 8.38 (d, J=5.52 Hz, 2H) 11.05 (br s, 1H).

Step 4

75 mg of 10g (124 μmol, 1 eq) was dissolved in a mixed solvent of 3 mL of acetonitrile and 3 mL of ethyl acetate, to which 1 mL of water was then added. To the mixture was added 80 mg of iodobenzene diacetate (248 μmol, 2.0 eq) with stirring. The reaction solution was stirred at 20° C. for 2 hours. After the reaction was completed, the reaction solution was isolated by preparative chromatography (Column type: PhenomenexSynergi C18 150*25 mm*10 μm; mobile phase: [A: water (0.225% FA), B: ACN]; B %: 18%-38%, 10 min) to afford the product of Example 10. $^1$H NMR (400 MHz, DMSO-$d_6$) δ ppm 0.72-0.85 (m, 2H) 1.04 (br s, 2H) 5.91 (d, J=5.65 Hz, 1H) 6.40 (s, 2H) 7.09-7.28 (m, 6H) 7.74 (d, J=5.65 Hz, 1H) 7.90-7.99 (m, 1H) 8.34 (s, 2H) 12.27 (s, 1H).

Example 11

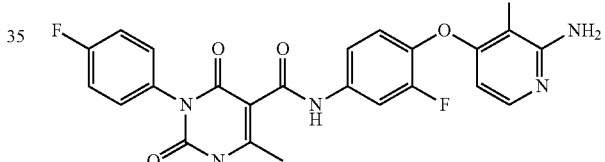

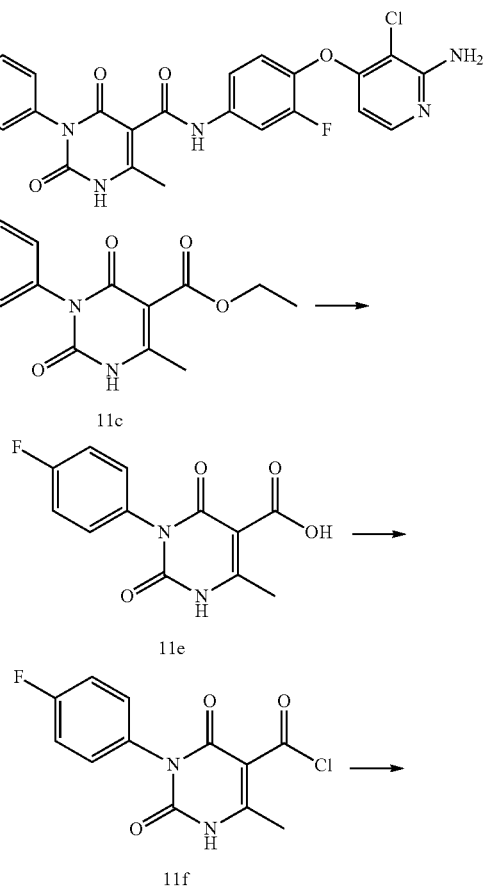

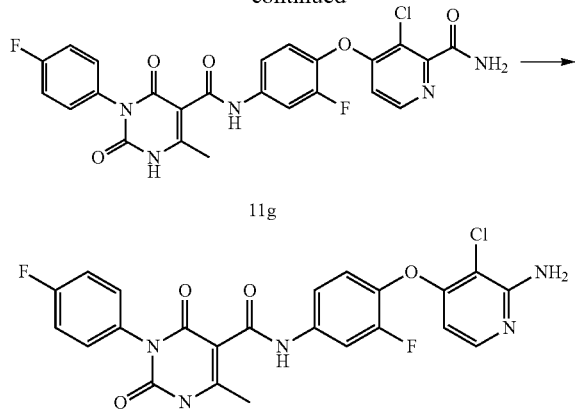

11g

Example 11

Step 1

0.14 g of 11c (479 μmol, 1 eq) was dissolved in 6 mL of ethanol, which was then added to a solution of 0.081 g of potassium hydroxide (1.44 mmol, 1 eq) in 2 mL of water. The reaction solution was stirred at 80° C. for 16 hours. After the reaction was completed, the reaction solution was concentrated to remove most of the ethanol. The reaction solution was then diluted with 20 mL of water, and extracted with ethyl acetate (30 mL×1). The organic phase was discarded. The aqueous phase was adjusted to pH of 3, and then extracted with ethyl acetate (30 mL×2). The organic phases were combined, washed with 30 mL of saturated brine, and dried over anhydrous sodium sulfate. The dried organic phase was rotary evaporated to remove the solvent to afford 11e. $^1$H NMR (400 MHz, DMSO-$d_6$) δ ppm 2.56 (s, 3H) 7.29-7.45 (m, 4H) 12.30 (br s, 1H) 13.34-13.53 (m, 1H).

Step 2

120 mg of 11e (446 μmol, 1 eq) was dissolved in 5 mL of tetrahydrofuran. To the mixture was added dropwise 1 μL of DMF followed by 47 μL of oxalyl chloride with stirring. The reaction solution was stirred at 20° C. for 0.5 hour. After the reaction was completed, the reaction solution was concentrated to remove the solvent to afford an oily crude product 11f, which was used in the next step without purification.

Step 3

150 mg of 1f1 (532 μmol, 1 eq) was dissolved in 20 mL of tetrahydrofuran, to which 880 μL of diisopropylethylamine (2.0 eq) was then added dropwise. 125 mg of 10f product was dissolved in 5 mL of tetrahydrofuran, which was then added dropwise to the above solution. The reaction solution was stirred at 20° C. for 0.5 hour. After the reaction was completed, the reaction solution was concentrated to remove the solvent. The reaction solution was then diluted with 30 mL of water, and extracted with ethyl acetate (50 mL×1). The aqueous phase was discarded. The organic phase was washed with saturated ammonium chloride solution (30 mL×1), saturated sodium carbonate solution (30 mL×1) and saturated brine, and dried over anhydrous sodium sulfate. The dried organic phase was rotary evaporated to remove the solvent to afford 11g.

Step 4

180 mg of 11g (341 μmol, 1 eq) was dissolved in 6 mL of DMF, to which 2 mL of water was then added. To the mixture was added 220 mg of iodobenzene diacetate (683 μmol, 2.0 eq) with stirring. The reaction solution was stirred at 20° C. for 0.5 hour. After the reaction was completed, the reaction solution was isolated by preparative chromatography (Column type: Phenomenex Synergi C18 150*25 mm*10 μm; mobile phase: [A: water (0.225% FA), B: ACN]; B %: 16%-46%, 10 min) to afford the product of Example 11. $^1$H NMR (400 MHz, DMSO-$d_6$) δ ppm 2.47 (s, 3H) 2.65-2.70 (m, 1H) 5.92 (d, J=5.62 Hz, 1H) 6.41 (s, 2H) 7.24-7.43 (m, 6H) 7.75 (d, J=5.62 Hz, 1H) 7.90 (dd, J=13.14, 2.38 Hz, 1H) 8.17 (s, 1H) 11.03 (s, 1H).

Example 12

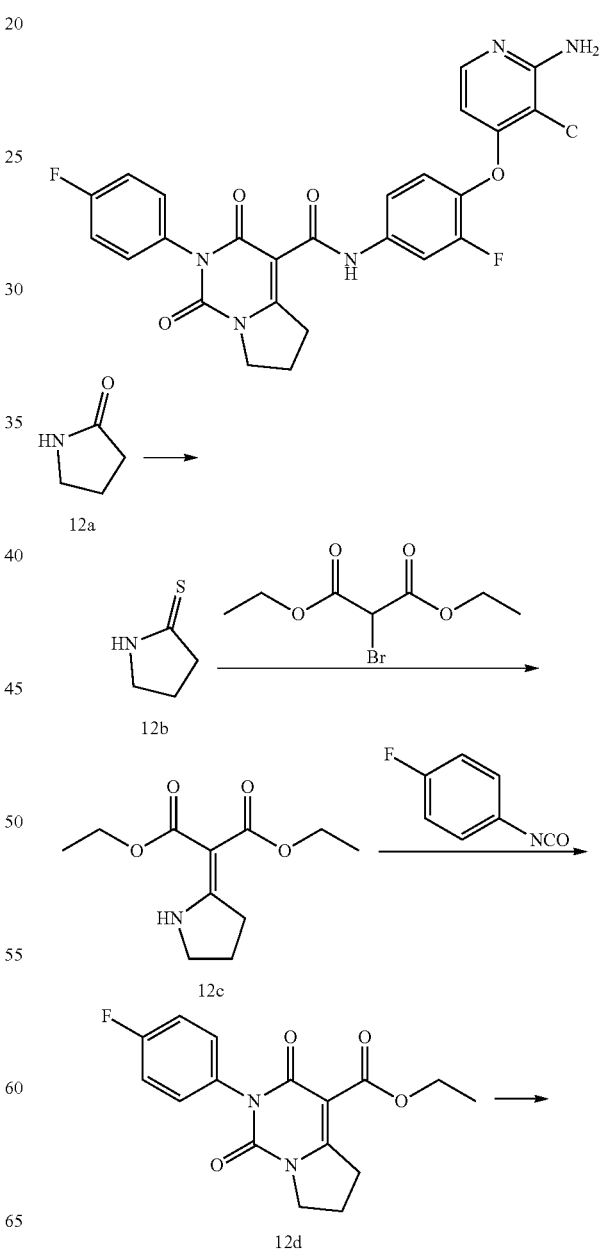

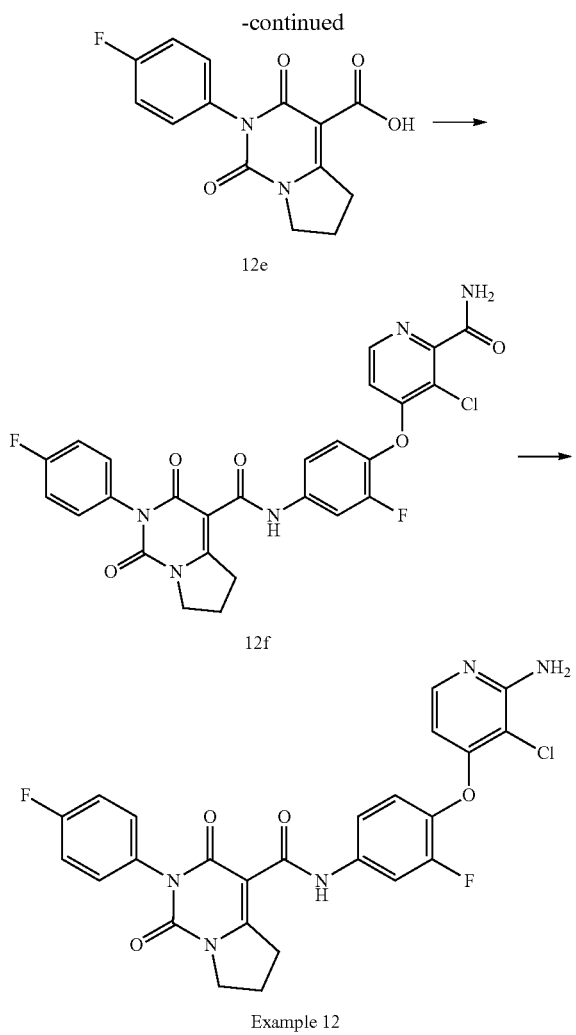

12e

12f

Example 12

Step 1

5g of 12a (58.8 mmol, 1 eq) was dissolved in 200 mL of THF, to which 14.3 g of Lawson's reagent (35.3 mmol, 0.6 eq) was then added. The reaction solution was stirred at 80° C. for 12 hours. After the reaction was completed, the reaction solution was concentrated to remove the solvent. The residue was purified by column chromatography (PE:EA=3:1) to afford a product 12b. $^1$H NMR (400 MHz, CDCl$_3$) δ=8.47 (br s, 1H), 3.68 (t, J=7.2 Hz, 2H), 2.93 (t, J=8.0 Hz, 2H), 2.24 (quin, J=7.6 Hz, 2H).

Step 2

3 g of 12b (29.65 mmol, 1 eq) was dissolved in a mixed solvent of 10 mL of tetrahydrofuran and 10 mL of water, to which 5 g of sodium bicarbonate (2.0 eq) and 7.8 g of diethyl bromomalonate (32.62 mmol, 1.1 eq) were then added. The reaction solution was stirred at 60° C. for 3 hours. After the reaction was completed, the reaction solution was diluted with 30 mL of water, and extracted with ethyl acetate (50 mL×2). The organic phase was washed with saturated ammonium chloride solution (30 mL×1), saturated sodium carbonate solution (30 mL×1) and saturated brine, and dried over anhydrous sodium sulfate. The dried organic phase was rotary evaporated to remove the solvent, and the residue was purified by column chromatography (PE:EA=3:1) to afford a product 12c. $^1$H NMR (400 MHz, CD$_3$OD) δ=4.16 (q, J=7.0 Hz, 4H), 3.63 (t, J=7.3 Hz, 2H), 3.09 (t, J=7.8 Hz, 2H), 2.05 (quin, J=7.6 Hz, 2H), 1.29 (t, J=7.1 Hz, 6H).

Step 3

1 g of 12c (4.40 mmol, 1 eq) was dissolved in 10 mL of tetrahydrofuran, to which 1.44 g of triphosgene (4.84 mmol, 1.1 eq) was then added. The reaction solution was stirred at 25° C. for 12 hours. 1.47 g of p-fluoroaniline was then added, and stirred for 0.5 hour. The reaction solution was diluted with water and extracted with ethyl acetate (50 mL×2). The organic phase was washed with saturated ammonium chloride solution (30 mL×1), saturated sodium carbonate solution (30 mL×1) and saturated brine, dried over anhydrous sodium sulfate, and rotary evaporated to remove the solvent. The residue was purified by column chromatography (PE:EA=3:1) to afford a product 12d. $^1$H NMR (400 MHz, CD$_3$OD) δ=7.33-7.18 (m, 4H), 4.60 (s, 1H), 4.37-4.25 (m, 2H), 4.08 (t, J=7.5 Hz, 2H), 3.50 (t, J=7.8 Hz, 2H), 2.25 (quin, J=7.7 Hz, 2H), 1.40-1.31 (m, 3H).

Step 4

0.17 g of 12d (282 μmol, 1 eq) was dissolved in 2 mL of ethanol, which was then added to a solution of 0.03 g of sodium hydroxide (0.75 mmol, 2.6 eq) in 2 mL of water. The reaction solution was stirred at 80° C. for 16 hours. After the reaction was completed, the reaction solution was concentrated to remove most of the ethanol. The reaction solution was then diluted with 2 mL of water, and extracted with ethyl acetate (2 mL×1). The organic phase was discarded. The aqueous phase was adjusted to pH of 3, and then extracted with ethyl acetate (10 mL×2). The organic phases were combined, washed with 2 mL of saturated brine, and dried over anhydrous sodium sulfate. The dried organic phase was rotary evaporated to remove the solvent to afford 12e. $^1$H NMR (400 MHz, CD$_3$OD δ=7.42-7.20 (m, 4H), 4.20-4.07 (m, 2H), 3.68 (t, J=7.9 Hz, 2H), 2.37-2.22 (m, 2H).

Step 5

80 mg of 12e (265 μmol, 1 eq) was dissolved in 5 mL of tetrahydrofuran. To the mixture was added dropwise 1 μL of DMF followed by 46 μL of oxalyl chloride. The reaction solution was stirred at 20° C. for 0.5 hour. After the reaction was completed, the reaction solution was concentrated to remove the solvent to afford the crude product 11f. The product was not purified and was dissolved in 5 mL of tetrahydrofuran. To the solution were then added 75 mg of 1f1 (265 μmol, 1 eq) and 150 μL of triethylamine (1.06 mmol, 4 eq). The reaction solution was stirred at 25° C. for 1 hour. After the reaction was completed, the reaction solution was concentrated to remove the solvent. The reaction solution was then diluted with 10 mL of water, and extracted with ethyl acetate (20 mL×1). The aqueous phase was discarded. The organic phase was washed with saturated ammonium chloride solution (30 mL×1), saturated sodium carbonate solution (30 mL×1) and saturated brine, and dried over anhydrous sodium sulfate. The dried organic phase was rotary evaporated to remove the solvent, and the residue was slurried with 2 mL of methanol to afford 12f. $^1$H NMR (400 MHz, DMSO-d6) δ=11.40 (s, 1H), 8.34 (d, J=5.6 Hz, 1H), 8.14-7.96 (m, 2H), 7.76 (s, 1H), 7.49 (br d, J=7.4 Hz, 1H), 7.42-7.35 (m, 5H), 6.92-6.73 (m, 1H), 4.00 (t, J=7.4 Hz, 2H), 3.64 (t, J=8.0 Hz, 2H), 2.27-2.09 (m, 2H).

Step 6

50 mg of 12f (87 μmol, 1 eq) was dissolved in 0.5 mL of DMF, to which 0.5 mL of water was then added. To the mixture was added 56 mg of iodobenzene diacetate (173.68 μmol, 2 eq) with stirring. The reaction solution was stirred at 25° C. for 1 hour. The reaction solution was then diluted with 10 mL of water, and extracted with ethyl acetate (20 mL×1). The aqueous phase was discarded. The organic phase was washed with saturated ammonium chloride solution (30 mL×1), saturated sodium carbonate solution (30 mL×1) and saturated brine, and dried over anhydrous sodium sulfate. The dried organic phase was rotary evaporated to remove the solvent, and the residue was purified by preparative chromatography (Column type: Phenomenex luna C18 250*50 mm*10 μm; mobile phase: [A: water (0.225% FA), B: ACN]; B %: 10%-40%, 33 min) to afford the product of Example 12. $^1$H NMR (400 MHz, DMSO-d6) δ=11.35 (s, 1H), 7.93 (dd, J=2.4, 13.2 Hz, 1H), 7.75 (d, J=5.8 Hz, 1H), 7.47-7.35 (m, 5H), 7.31-7.26 (m, 1H), 6.42 (s, 2H), 5.92 (d, J=5.8 Hz, 1H), 3.99 (t, J=7.4 Hz, 2H), 3.64 (t, J=7.7 Hz, 2H), 2.17 (quin, J=7.7 Hz, 2H).

Example 13

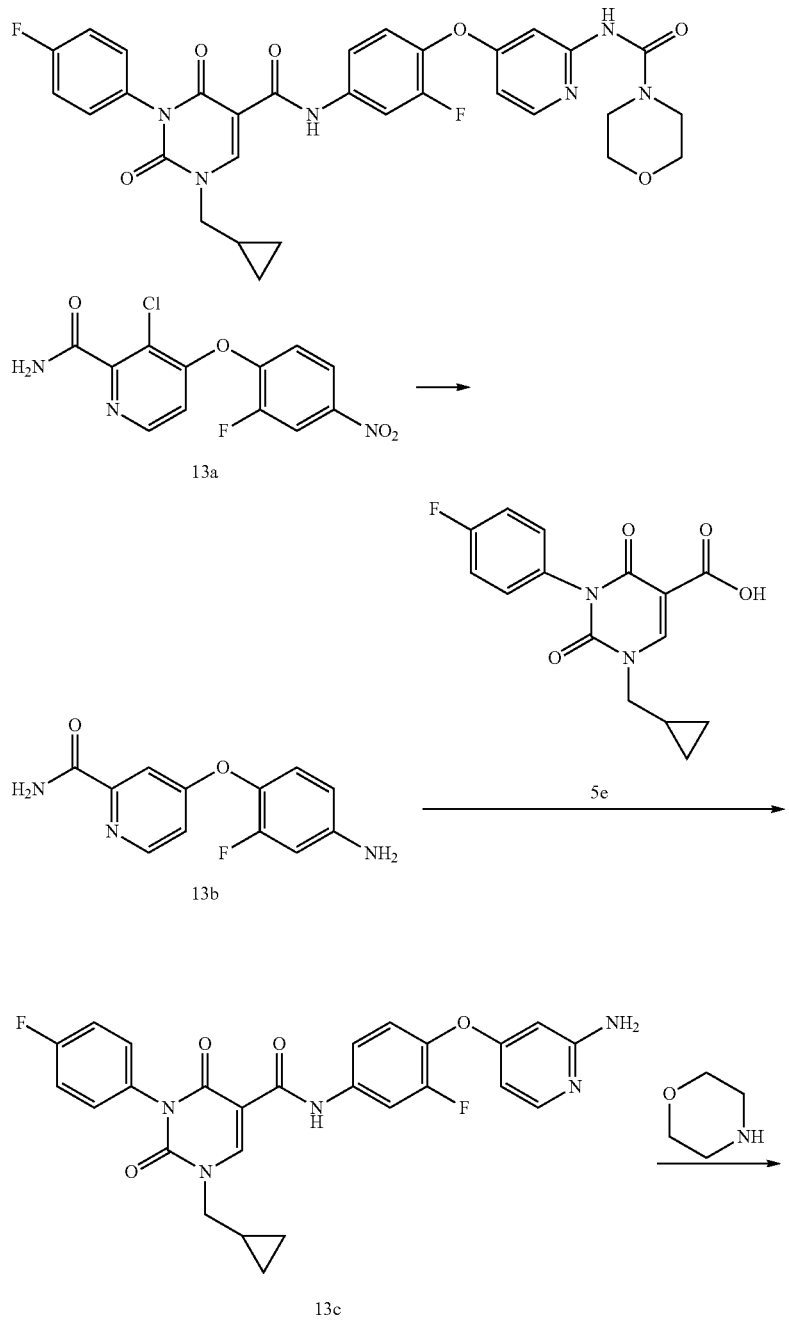

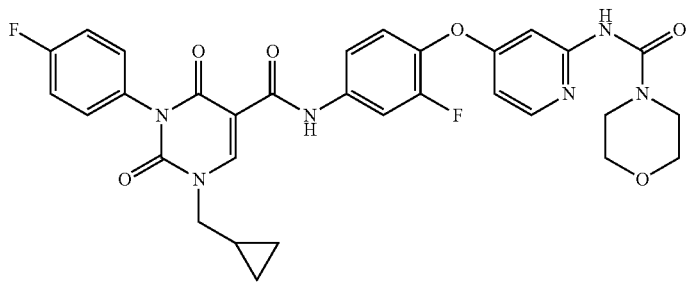

Example 13

Step 1

1 g of 13a (3.55 mmol, 1 eq) and 0.01 g of Pd/C (10% purity) were added to 10 mL of methanol. The reaction solution was stirred in hydrogen (1 atm) atmosphere at 25° C. for 12 hours. After the reaction was completed, the reaction solution was filtered. The filtrate was concentrated to afford a crude compound 13b, which was used directly in the next step.

Step 2

712.21 mg of 5e (2.34 mmol, 1 eq) was dissolved in 5 mL of DMF. To the reaction system were sequentially added 1.33 g of HATU (3.51 mmol, 1.5 eq), 710.56 mg of triethylamine (7.02 mmol, 977.39 μL, 3 eq) and 640 mg of 13b (2.34 mmol, 1 eq). The reaction solution was stirred at 35° C. for 3 hours. After the reaction was completed, the reaction solution was added with 10 mL of water and then filtered. The filter cake was collected and dried to afford crude compound 13c, which was used directly in the next step.

Step 3

200 mg of 13c (374.90 μmol, 1 eq) was dissolved in 5 mL of DMF. To the reaction system were added 144.90 mg of iodobenzene diacetate (449.87 μmol, 1.2 eq) and 97.98 mg of morpholine (1.12 mmol, 98.97 μL, 3 eq) in sequence. The reaction solution was stirred at 35° C. for 24 hours. After the reaction was completed, the reaction solution was filtered. The filtrate was concentrated under reduced pressure, and the residue was isolated by preparative chromatography (Column type: Phenomenex luna C18 250*50 mm*10 μm; mobile phase: [A: water (0.225% FA), B: ACN]; B %: 25%-55%, 30 min) to afford the product of Example 13. $^1$H NMR (400 MHz, DMSO-d6) δ ppm 0.44 (br d, J=4.89 Hz, 2H), 0.57 (br d, J=8.19 Hz, 2H), 1.24 (br s, 1H), 3.54 (br d, J=5.26 Hz, 4H), 3.60 (br s, 2H), 3.86 (br d, J=7.09 Hz, 4H), 6.63 (br d, J=3.42 Hz, 1H), 7.28-7.33 (m, 1H), 7.43 (br d, J=5.01 Hz, 2H), 7.50 (br d, J=8.56 Hz, 1H), 7.98 (br d, J=12.84 Hz, 1H), 8.13 (d, J=5.99 Hz, 1H), 8.12-8.14 (m, 1H), 8.44 (br s, 2H), 8.92 (s, 1H), 9.30 (s, 1H), 11.02 (s, 1H).

Example 14

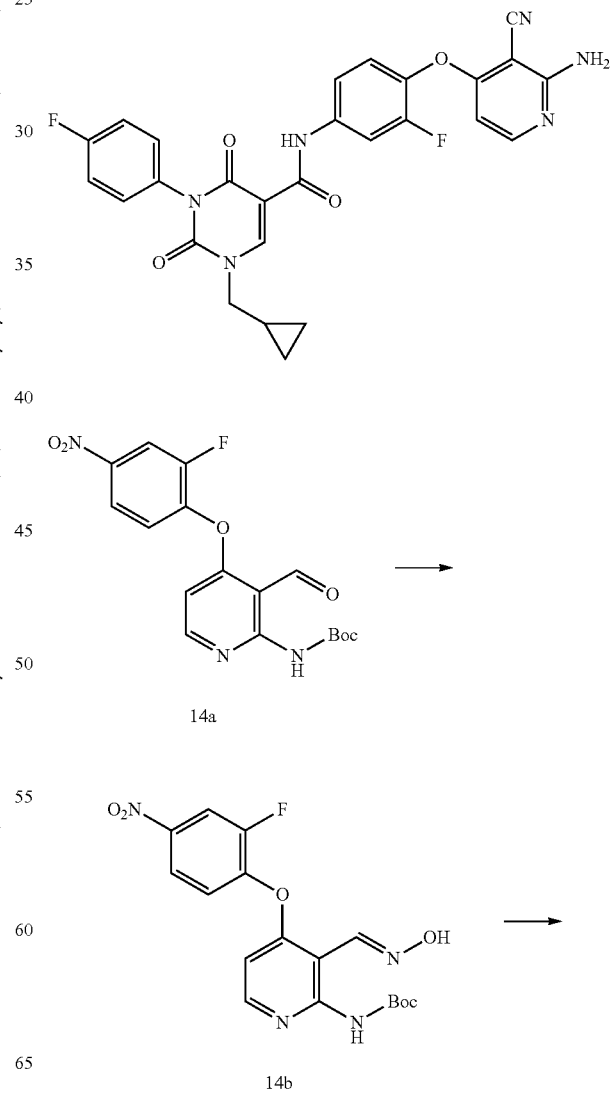

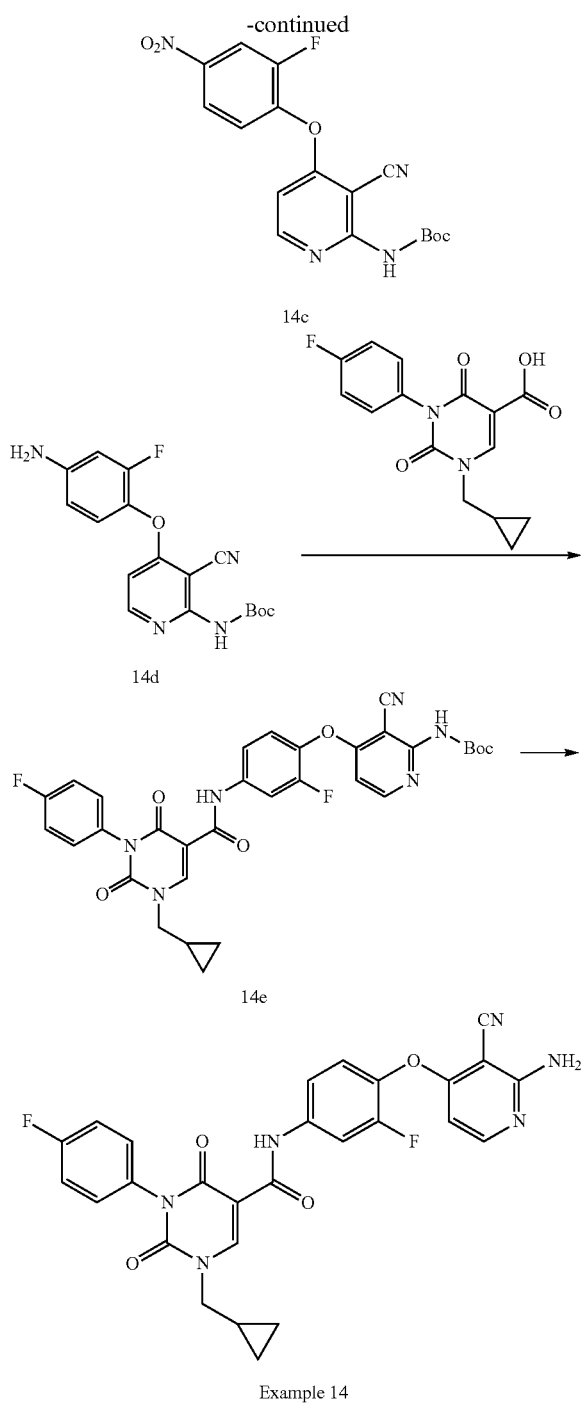

Example 14

Step 1

200 mg of 14a (200 mg, 530.05 μmol, 1 eq) and 44.20 mg of NH$_2$OH.HCl (636.06 μmol, 1.2 eq) were dissolved in 4 mL of ethanol and 2 mL of water, to which 52.18 mg of sodium acetate (636.06 μmol, 1.2 eq) was then added. The reaction solution was stirred at 15° C. for 0.5 hour, and then heated to 70° C. and stirred for 0.5 hour. After the reaction was completed, the reaction solution was concentrated under reduced pressure to remove the ethanol. The reaction solution was then diluted with 10 mL of water and extracted with ethyl acetate (15 mL×3). The organic phases were combined, washed with saturated brine (10 mL), and dried over anhydrous sodium sulfate. The dried organic phase was filtered, and the filtrate was concentrated under reduced pressure to afford a crude 14b, which was used directly in the next reaction.

Step 2

200 mg of 14b (509.76 μmol, 1 eq) was dissolved in 5 mL of dichloromethane. To the reaction system at 0° C. were added 128.96 mg of triethylamine (1.27 mmol, 2.5 eq) and 267.66 mg of trifluoroacetic anhydride (1.27 mmol, 2.5 eq) with stirring. The reaction solution was stirred at 0° C. for 1.5 hours. After the reaction was completed, the reaction solution was quenched with 6 mL of saturated sodium bicarbonate solution, and concentrated under reduced pressure to remove the solvent. The residue was diluted with 10 mL of water, and extracted with ethyl acetate (15 mL×3). The organic phases were combined, washed with saturated brine (10 mL) and dried over anhydrous sodium sulfate. The dried organic phase was filtered and concentrated under reduced pressure to afford the residue, namely crude 14c, which was used directly in the next reaction.

Step 3

160 mg of 14c (316.30 μmol, 1 eq) was dissolved in 5 mL of methanol. 67.32 mg of Pd/C (10% purity, 63.26 μmol, 0.2 eq) was added to the reaction system. The reaction solution was stirred under hydrogen atmosphere (1 atm) at 15° C. for 1 hour. After the reaction was completed, the reaction solution was filtered to remove the catalyst. The filtrate was concentrated under reduced pressure, and the residue was purified by column chromatography to afford a compound 14d.

Step 4

40 mg of 14d (102.22 μmol, 1 eq), 30 mg of 5e (102.22 μmol, 1 eq) were dissolved in 5 mL of DMF at 15° C. To the reaction system were added 31.03 mg of triethylamine (306.67 μmol, 3 eq) and 58.30 mg of HATU (153.34 μmol, 1.5 eq) in sequence. The reaction solution was stirred at 15° C. for 0.5 hour, and then heated to 40° C. and stirred for 1 hour. After the reaction was completed, the reaction solution was added with 10 mL of water, and filtered. The obtained solid was washed with water, dried, and purified by preparative thin layer chromatography to afford 14e.

Step 5

40 mg of 14e (52.65 μmol, 1 eq) was dissolved in 2 mL of dichloromethane. To the reaction solution was added 0.67 mL of trifluoroacetic acid at 0° C. The reaction system was stirred at 15° C. for 2 hours. After the reaction was completed, the reaction solution was quenched with 2 mL of ammonia, diluted with 5 mL of water, and extracted with dichloromethane (8 mL×3). The extract was washed with saturated brine (10 mL), dried over anhydrous sodium sulfate, and filtered. The filtrate was concentrated under reduced pressure and isolated by preparative chromatography (Column type: Phenomenex Synergi C18 150*30 mm*4 μm; mobile phase: [A: water (0.225% FA)-ACN]; B %: 40%-70%, 10 min) to afford the product of Example 14. $^1$H NMR (400 MHz, DMSO-d$_6$) δ ppm 0.44 (br d, J=4.77 Hz, 2H) 0.56 (br d, J=7.58 Hz, 2H) 1.24 (br d, J=6.24 Hz, 1H) 3.86 (br d, J=7.09 Hz, 2H) 5.89 (d, J=6.11 Hz, 1H) 7.06 (s, 2H) 7.33-7.51 (m, 6H) 7.96-8.05 (m, 2H) 8.91 (s, 1H) 11.02 (s, 1H).

Example 15
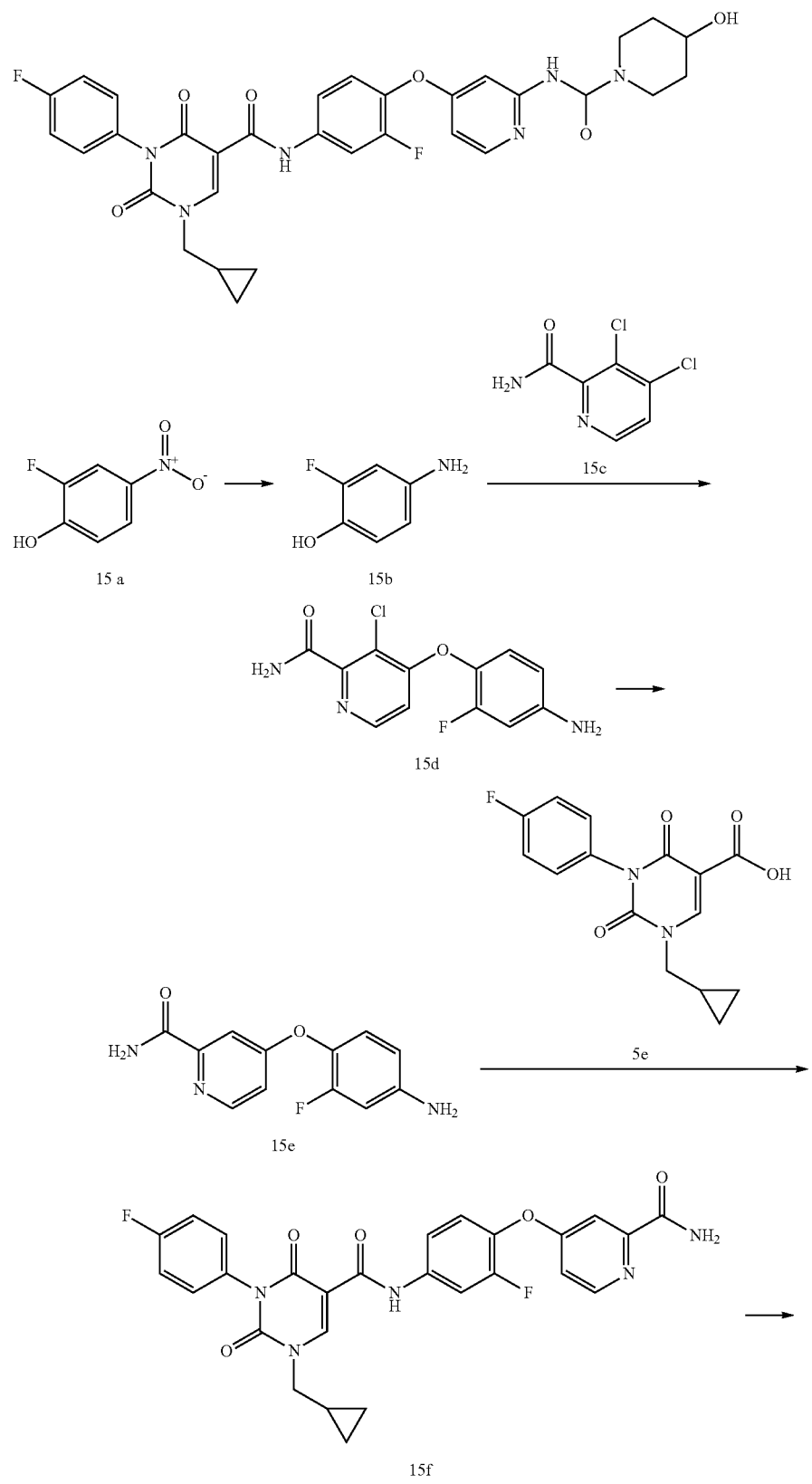

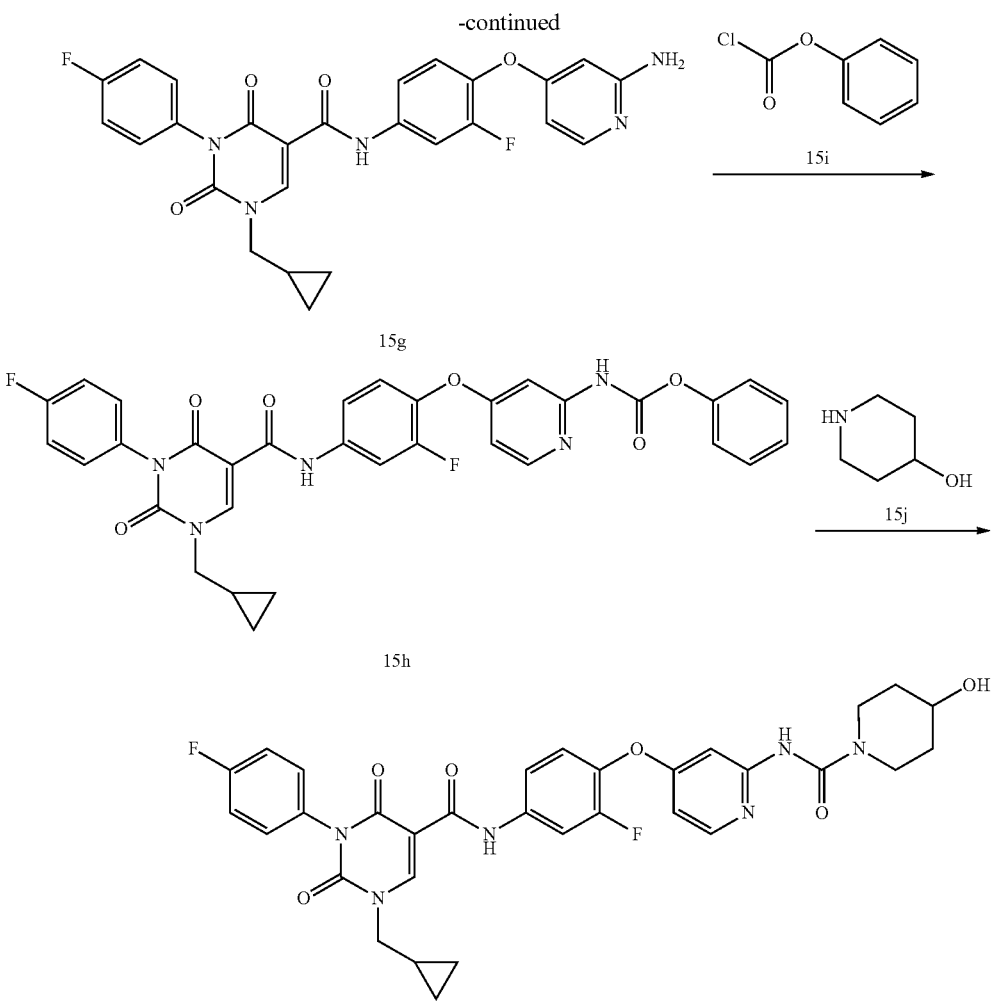

Example 15

Step 1

10 g of 15a (63.65 mmol, 1 eq) was dissolved in 100 mL of methanol. To the reaction system was added 1 g of Pd/C (10% purity). The reaction solution was stirred in a hydrogen atmosphere (50 psi) at 25° C. for 12 hours. After the reaction was completed, the reaction solution was filtered. The filtrate was distilled under reduced pressure to remove the solvent to afford a crude 15b, which was used directly in the next step.

Step 2

4.94 g of 15c (25.86 mmol, 1 eq) was dissolved in 50 mL of DMF. To the reaction system were added 4.35 g of potassium tert-butoxide (38.79 mmol, 1.5 eq) and 4.1 g of 15b (29.74 mmol, 1.15 eq) in sequence. The reaction solution was stirred at 55° C. for 3 hours. After the reaction was completed, 150 mL of water was added to the reaction system, which was then extracted with ethyl acetate (100 mL*2). The organic phases are combined, dried with anhydrous sodium sulfate, and then filtered. The filtrate was distilled under reduced pressure to remove the solvent to afford a crude 15d, which was used directly in the next step.

Step 3

7 g of 15d (23.71 mmol, 1 eq) was dissolved in 100 mL of methanol. 0.2 g of Pd/C (10% purity) was added to the reaction system. The reaction solution was stirred in a hydrogen atmosphere (15 psi) at 35° C. for 12 hours. After the reaction was completed, the reaction solution was filtered. The filtrate was distilled under reduced pressure to remove the solvent to afford crude 15e, which was used directly in the next step.

Step 4

3.4 g of 15e (13.75 mmol, 1 eq) and 5.05 g of 5e (16.50 mmol, 1.2 eq) were dissolved in 50 mL of DMF. To the reaction system were added 7.84 g of HATU (20.63 mmol, 1.5 eq) and 4.17 g of triethylamine (41.26 mmol, 3 eq) in sequence. The reaction solution was stirred at 25° C. for 3 hours. After the reaction was completed, 40 mL of water was added to the reaction solution, which was then filtered. The filter cake was dried and slurried with methanol (10 mL). The resulting solid was dried to afford 15f.

Step 5

6.1 g of 15f (11.43 mmol, 1 eq) was dissolved in 60 mL of DMF. To the reaction system were added 3.68 g of iodobenzene diacetate (11.43 mmol, 1 eq) and 10 mL of water in sequence. The reaction solution was stirred at 30° C. for 3 hours. After the reaction was completed, 50 mL of water was added to the reaction solution, which was then extracted with ethyl acetate (150 mL×2). The organic phases were combined, washed with saturated brine (100 mL*2), and dried over anhydrous sodium sulfate. The dried organic phase was filtered, and the filtrate was concentrated under reduced pressure. The residue was slurried with ethanol (20 mL), and the resulting solid was dried to afford 15g.

Step 6

1 g of 15g (1.98 mmol, 1 eq) was dissolved in 10 mL of dichloromethane. To the reaction system were added 600.57 mg of triethylamine (5.94 mmol, 3 eq) and 371.69 mg of 15i (2.37 mmol, 1.2 eq) in sequence. The reaction solution was stirred at 20° C. for 1 hour. The reaction solution was concentrated under reduced pressure to remove the solvent to afford a crude 15h, which was used directly in the next step.

Step 7

1.3 g of 15h (2.08 mmol, 1 eq) was dissolved in 15 mL of dichloromethane. To the reaction system was added 1.05 g of 15j (10.39 mmol, 5 eq). The reaction solution was stirred at 20° C. for 1 hour. After the reaction was completed, the reaction solution was concentrated under reduced pressure. The residue was isolated by preparative chromatography (Column type: Phenomenex Synergi C18 150*25*10 μm; mobile phase: [A: water (0.225% FA), B: ACN]; B %: 27%-57%, 10 min) to afford the product of Example 15. $^1$H NMR (400 MHz, DMSO-d6) δ ppm 0.44 (q, J=4.77 Hz, 2H), 0.52-0.63 (m, 2H), 1.18-1.37 (m, 3H), 1.62-1.77 (m, 2H), 2.97-3.08 (m, 2H), 3.64 (br s, 1H), 3.74-3.82 (m, 2H), 3.86 (d, J=7.09 Hz, 2H), 4.72 (br s, 1H), 6.59 (dd, J=5.75, 2.32 Hz, 1H), 7.30-7.34 (m, 1H), 7.34-7.39 (m, 3H), 7.40-7.46 (m, 2H), 7.46-7.51 (m, 1H), 7.96 (dd, J=12.84, 2.32 Hz, 1H), 8.09-8.16 (m, 1H), 8.90 (s, 1H), 9.16 (s, 1H), 11.00 (s, 1H).

Example 16

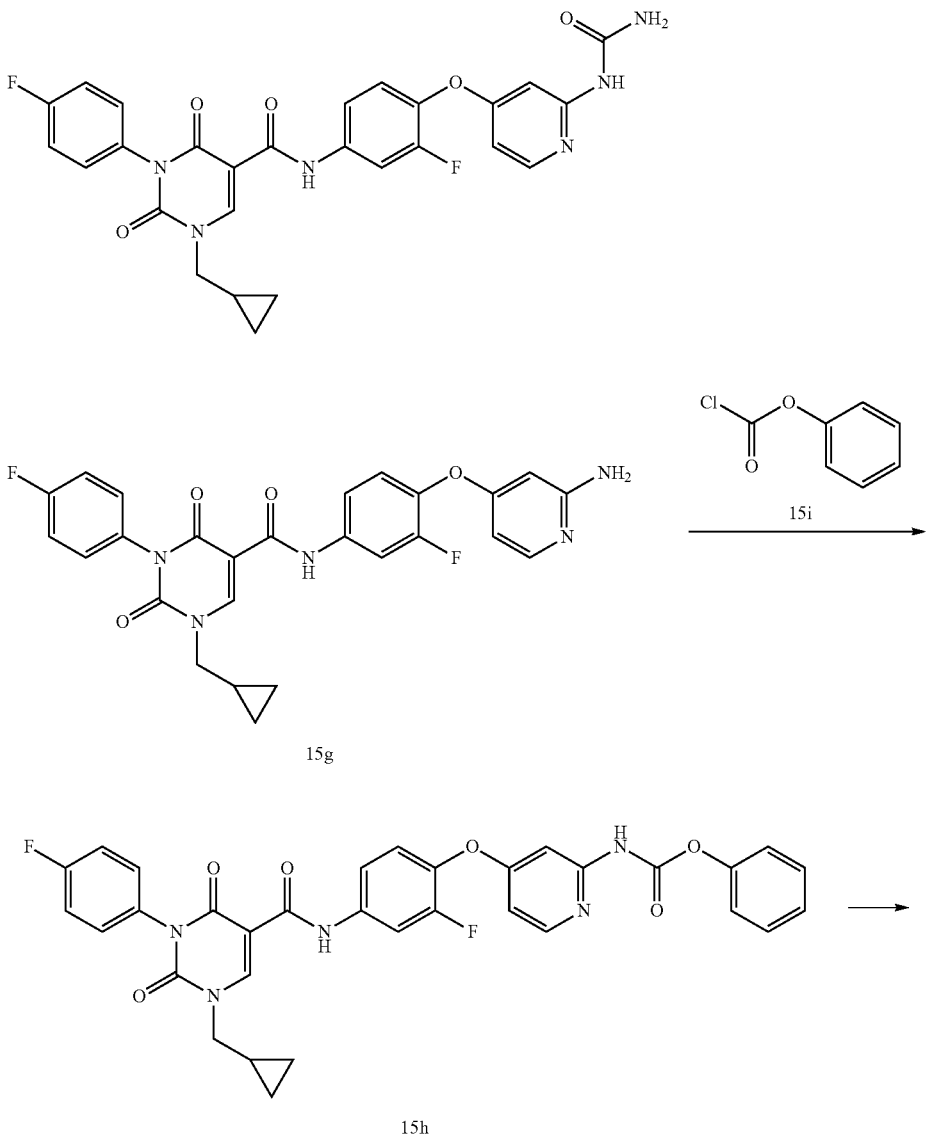

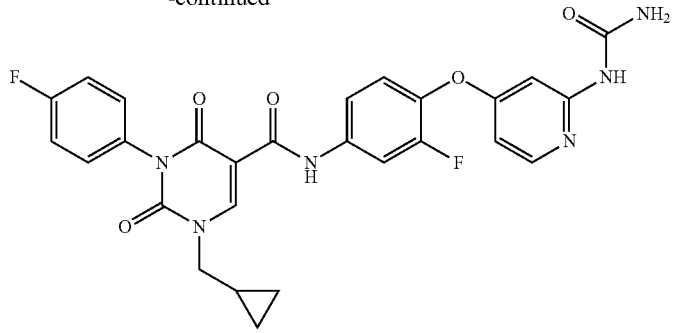

Example 16

Step 1

100 mg of 15g (197.83 μmol, 1 eq) was dissolved in 1 mL of dichloromethane. To the reaction system were added 30.03 mg of triethylamine (296.75 μmol, 1.5 eq) and 30.97 mg of 15i (197.83 μmol, 1 eq) in sequence. The reaction solution was stirred at 20° C. for 1 hour to afford a solution of product 15h in dichloromethane, which was used directly in the next step.

Step 2

To the reaction solution obtained in step 1 was added 60 μL of ammonia. The reaction solution was reacted with stirring at 20° C. for 24 hours. After the reaction was completed, 10 mL of water and 10 mL of dichloromethane were added to the reaction solution, and stirred for 5 minutes. The layers were separated. The organic phase was washed with saturated brine (10 mL*2), dried over anhydrous sodium sulfate, and filtered. The filtrate was concentrated under reduced pressure to remove the solvent. The residue was isolated by preparative chromatography (Column type: Phenomenex Synergi C18 150*25 mm*10 μm; mobile phase: [A: water (0.225% FA), B: ACN]; B %: 25%-55%, 10 min) to afford the product of Example 16. $^1$H NMR (400 MHz, DMSO-d6) δ ppm 0.44 (br s, 2H) 0.56 (br d, J=6.60 Hz, 1H) 1.25 (br s, 1H) 3.86 (br d, J=5.99 Hz, 2H) 6.54 (br s, 1H) 6.98 (br s, 1H) 7.36 (br t, J=8.62 Hz, 3H) 7.41-7.53 (m, 3H) 7.97 (br d, J=11.74 Hz, 1H) 8.07 (br d, J=4.77 Hz, 1H) 8.91 (s, 1H) 9.09 (br s, 1H) 11.01 (br s, 1H).

Example 17

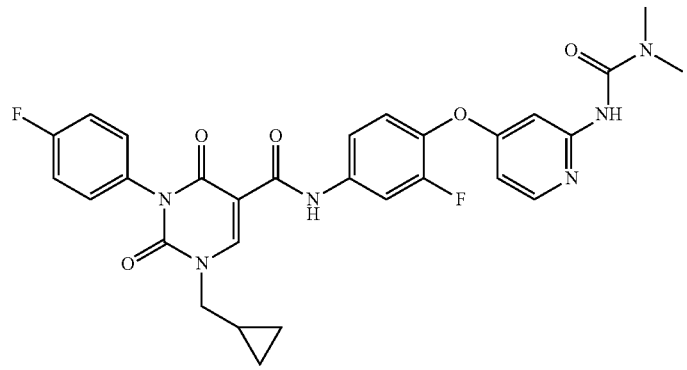

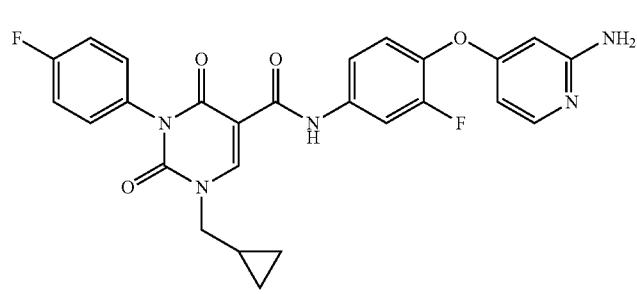 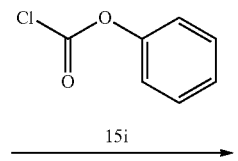

15g

15i

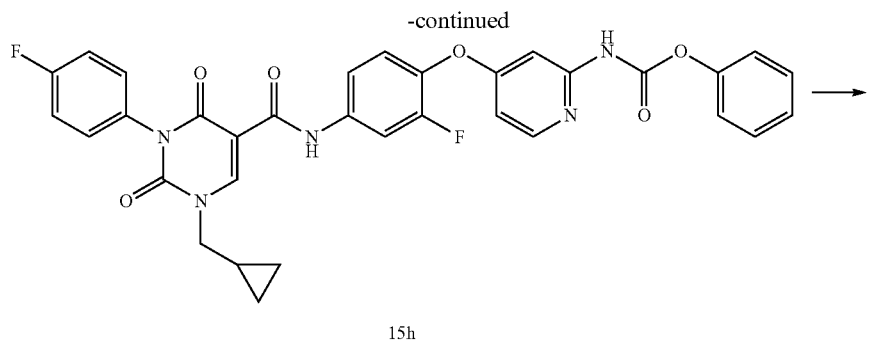

15h

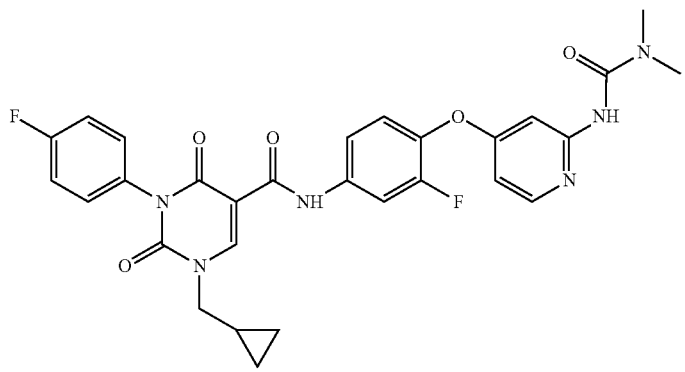

Example 17

Example 17

Step 1

200 mg of 15g (395.67 μmol, 1 eq) was dissolved in 2 mL of dichloromethane. To the reaction system were added 120 mg of triethylamine (1.19 mmol, 3 eq) and 74.34 mg of 15i (474.80 μmol, 1.2 eq) in sequence. The reaction solution was stirred at 10° C. for 2 hours. The reaction solution was then concentrated under reduced pressure to remove the solvent to afford 15h, which was used directly in the next step without purification.

Step 2

240 mg of 15h (383.65 μmol, 1 eq) was dissolved in 3 mL of dichloromethane. To the reaction system was added 959 μL of dimethylamine (2M tetrahydrofuran solution, 5 eq). The reaction solution was stirred at 20° C. for 1 hour. After the reaction was completed, the reaction solution was concentrated under reduced pressure to remove the solvent. The residue was isolated by preparative chromatography (Column type: Phenomenex luna C18 250*50 mm*10 μm; mobile phase: [A: water (0.225% FA), B: ACN]; B %: 35%-65%, 20 min) to afford the product of Example 17. $^1$H NMR (400 MHz, DMSO-d6) δ ppm 0.39-0.50 (m, 2H), 0.52-0.61 (m, 2H), 1.22-1.30 (m, 1H), 2.89 (s, 6H), 3.87 (d, J=7.21 Hz, 2H), 6.60 (dd, J=5.69, 2.38 Hz, 1H), 7.29-7.34 (m, 1H), 7.34-7.39 (m, 2H), 7.40 (d, J=2.20 Hz, 1H), 7.42-7.47 (m, 2H), 7.49 (dd, J=8.93, 1.34 Hz, 1H), 7.97 (dd, J=12.90, 2.38 Hz, 1H), 8.12 (d, J=5.62 Hz, 1H), 8.87 (s, 1H), 8.91 (s, 1H), 11.00 (s, 1H).

Example 18

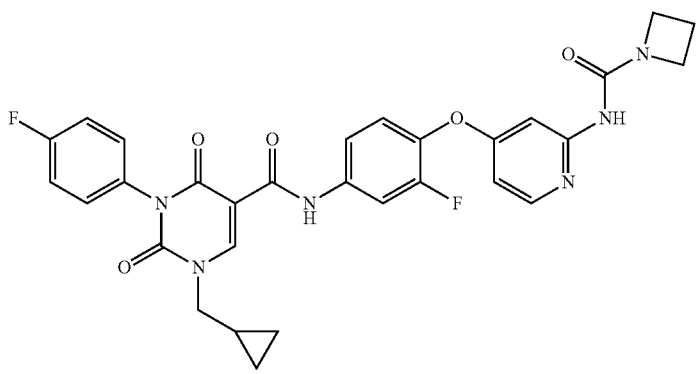

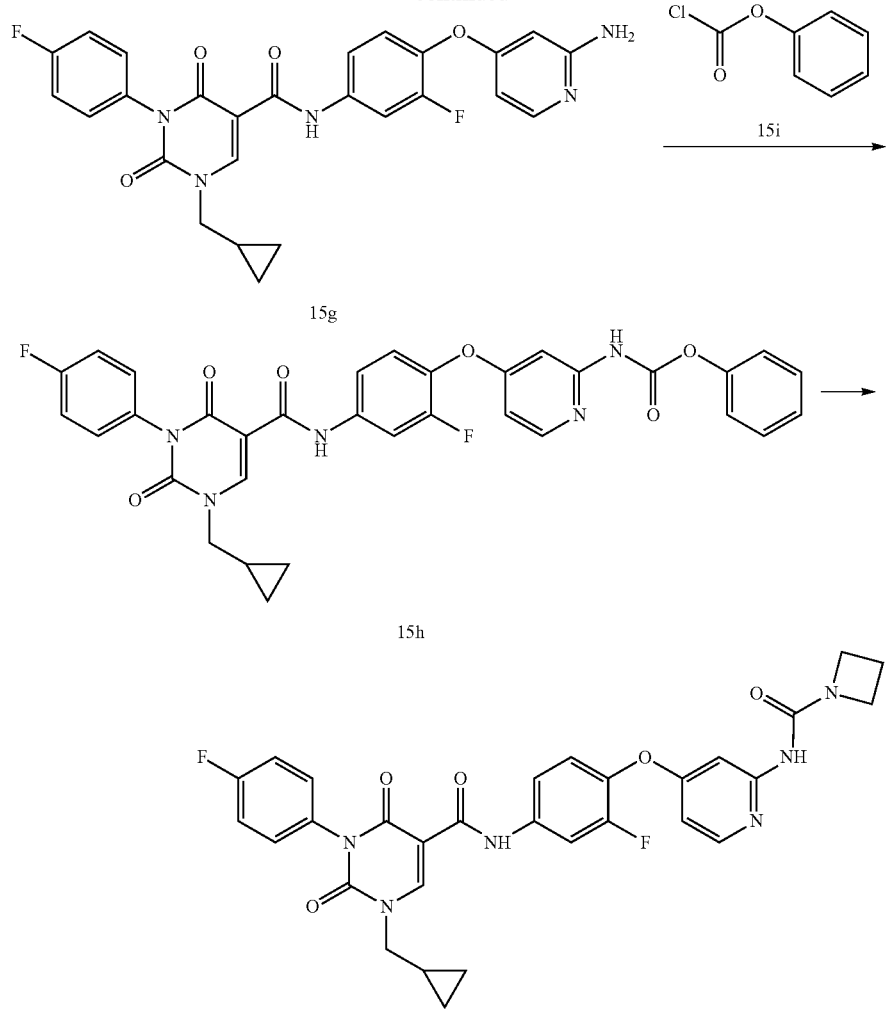

Example 18

Step 1

0.2 g of 15g (395.67 μmol, 1 eq) was dissolved in 2 mL of dichloromethane. To the reaction system were added 80.08 mg of triethylamine (791.34 μmol, 2 eq) and 92.92 mg of 15i (474.80 μmol, 1.5 eq) in sequence. The reaction solution was stirred at 20° C. for 2 hours. The reaction solution was then concentrated under reduced pressure to remove the solvent and afford 15h, which was used directly in the next step without purification.

Step 2

250 mg of 15h (399.63 μmol, 1 eq) was dissolved in 3 mL of dichloromethane. 112.16 mg of azetidine hydrochloride (1.20 mmol, 3 eq) was added to the reaction system. The reaction solution was stirred at 20° C. for 16 hours. After the reaction was completed, the reaction solution was concentrated under reduced pressure to remove the solvent. The residue was isolated by preparative chromatography (Column type: Phenomenex luna C18 250*50 mm*10 μm; mobile phase: [A: water (0.05% HCl), B: ACN]; B %: 25ACN %-55ACN %, 27 min) to afford the product of Example 18. 1H NMR (400 MHz, DMSO-d6) δ ppm 11.04 (s, 1H), 9.68 (br d, J=2.3 Hz, 1H), 8.91 (s, 1H), 8.19 (d, J=6.4 Hz, 1H), 8.01 (dd, J=2.3, 12.8 Hz, 1H), 7.54 (dd, J=1.4, 8.9 Hz, 1H), 7.47-7.33 (m, 3H), 7.24-7.16 (m, 1H), 6.86 (br d, J=5.5 Hz, 1H), 3.99 (br s, 2H), 3.86 (d, J=7.1 Hz, 2H), 2.28-2.13 (m, 2H), 1.30-1.21 (m, 1H), 0.64-0.52 (m, 2H), 0.48-0.38 (m, 2H).

Example 19

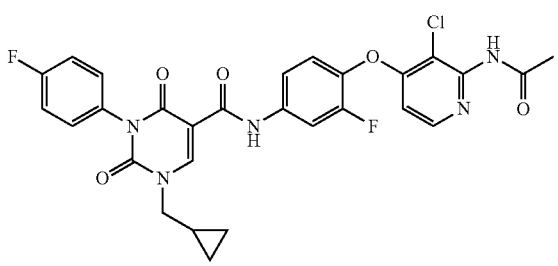

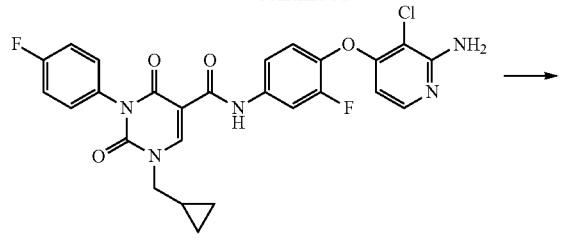

Example 5

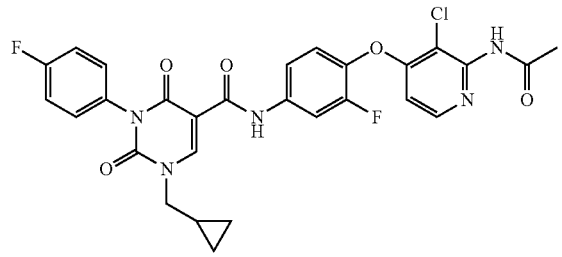

Example 19

Step 1

200 mg of the product of Example 5 (395.67 μmol, 1 eq) was dissolved in 2 mL of tetrahydrofuran. To the reaction system were added 153.14 mg of N,N-diisopropylethylamine (1.19 mmol, 3 eq) and 37.27 mg of acetyl chloride (474.80 μmol, 1.2 eq) in sequence. The reaction solution was stirred at 20° C. for 2 hours. After the reaction was completed, the solvent was removed under reduced pressure. The residue was isolated by preparative chromatography (Column type: Phenomenex luna C18 150*25*10 μm; mobile phase: [A: (0.225% FA), B: ACN]; B %: 36%-66%, 7.8 min) to afford the product of Example 19. 1H NMR (400 MHz, DMSO-d6) δ ppm 0.44 (br d, J=3.67 Hz, 2H) 0.52-0.60 (m, 2H) 1.24 (br d, J=7.09 Hz, 1H) 2.03 (s, 3H) 3.86 (d, J=7.09 Hz, 2H) 6.68 (dd, J=5.62, 2.32 Hz, 1H) 7.31-7.39 (m, 3H) 7.44 (dd, J=8.80, 5.14 Hz, 2H) 7.50 (br d, J=11.25 Hz, 1H) 7.65 (s, 1H) 7.97 (dd, J=12.78, 2.38 Hz, 1H) 8.18 (d, J=5.62 Hz, 1H) 8.91 (s, 1H) 10.56 (s, 1H) 11.01 (s, 1H).

Example 20

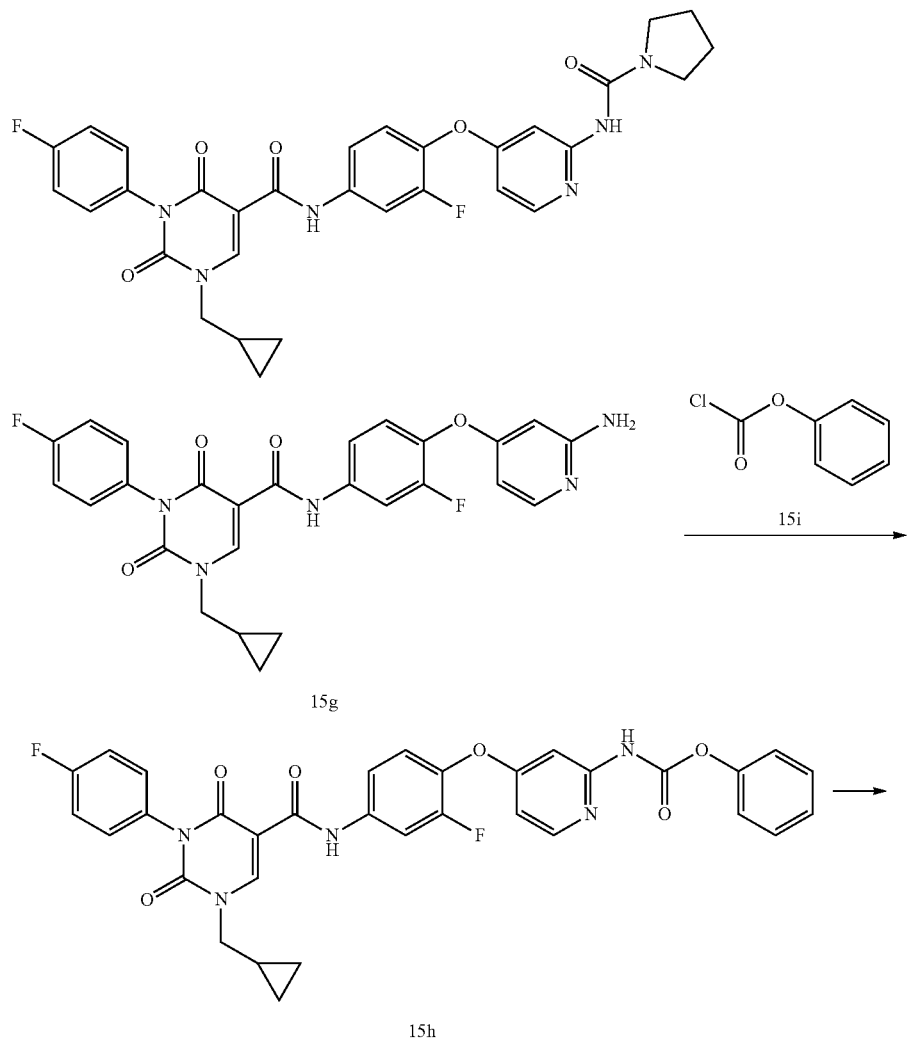

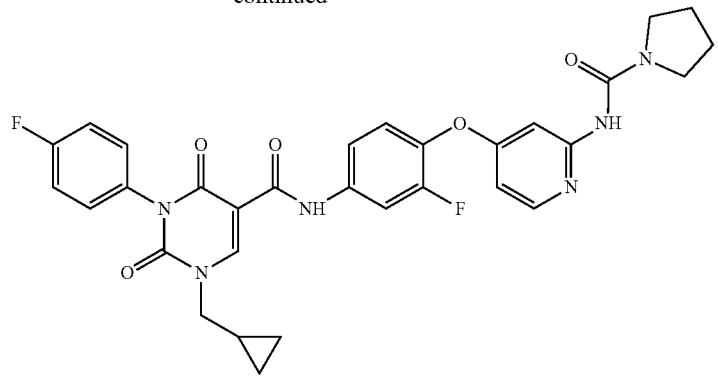

Example 20

Step 1

555 mg of 15g (960.24 μmol, 1 eq) was dissolved in 6 mL of dichloromethane. To the reaction system were added 291.50 mg of triethylamine (2.88 mmol, 3 eq) and 225.51 mg of 15i (1.44 mmol, 1.5 eq) in sequence. The reaction solution was stirred at 25° C. for 2 hours to afford a solution of product 15h in dichloromethane, which was used directly in the next step.

Step 2

To the reaction solution obtained in step 1 was added 341.07 mg of pyrrolidine (4.80 mmol, 5 eq). The reaction solution was stirred at 25° C. for 12 hours. After the reaction was completed, the solvent was removed under reduced pressure. The residue was isolated by preparative chromatography (Column type: Phenomenex luna C18 150*25 mm*10 μm; mobile phase: [A: water (0.225% FA), B: ACN]; B %: 26%-56%, 7.8 min) to afford the product of Example 20. 1H NMR (400 MHz, DMSO-d6) δ ppm 0.48-0.38 (m, 2H) 0.39-0.48 (m, 2H) 0.53-0.61 (m, 2H) 1.20-1.31 (m, 1H) 1.80 (br s, 4H) 3.36-3.38 (m, 4H) 3.86 (d, J=7.09 Hz, 2H) 6.60 (dd, J=5.75, 2.45 Hz, 1H) 7.29-7.39 (m, 3H) 7.41-7.51 (m, 4H) 7.96 (dd, J=12.90, 2.38 Hz, 1H) 8.11 (d, J=5.75 Hz, 1H) 8.67 (s, 1H) 8.90 (s, 1H) 11.00 (s, 1H).

Example 21

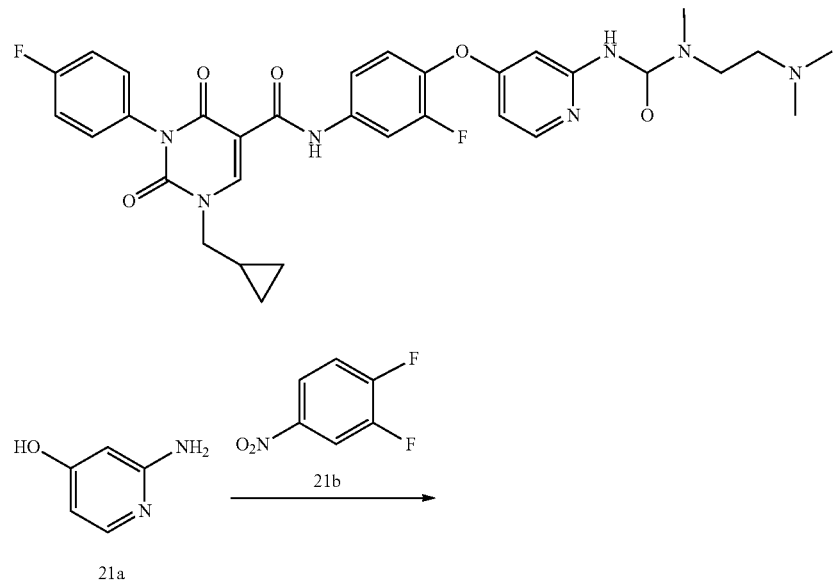

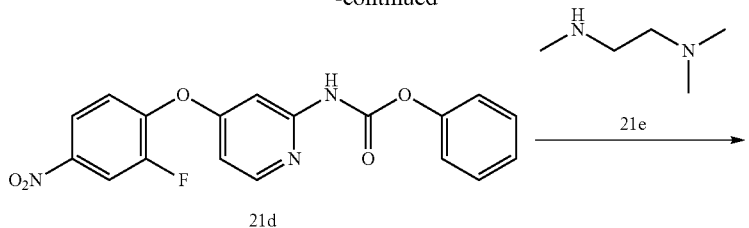

21d

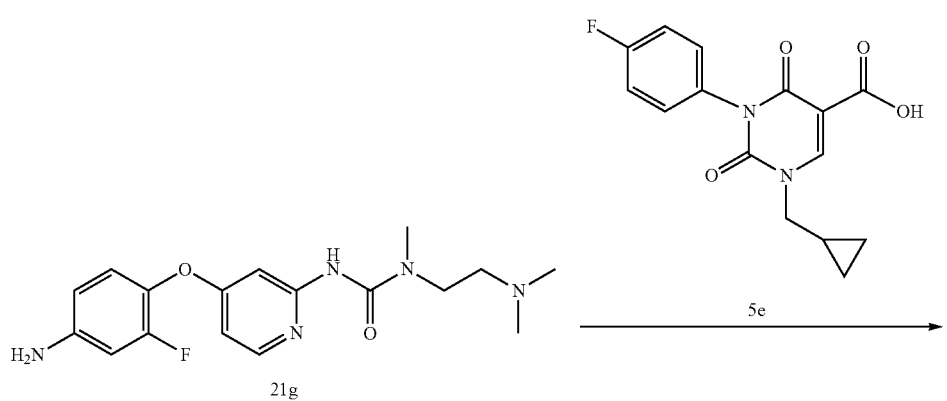

21f

21g

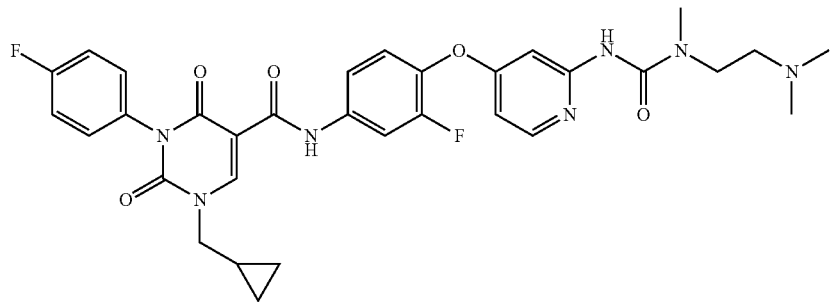

Example 21

Step 1

20 g of 21a (181.63 mmol, 1 eq) was dissolved in 200 mL of acetonitrile at room temperature, to which 25.10 g of potassium carbonate (181.63 mmol, 1 eq) and 32 g of 21b (201.14 mmol, 22.22 mL, 1.11 eq) were then added in sequence. The reaction solution was stirred at 50° C. for 16 hours. After the reaction was completed, the reaction solution was poured into 600 mL of water, stirred for 2 hours, and then filtered. The filter cake was collected and dried to afford a product 21c. $^1$HNMR (400 MHz, DMSO-$d_6$) δ ppm 6.00 (d, J=2.32 Hz, 1H) 6.10 (s, 2H) 6.26 (dd, J=5.75, 2.32 Hz, 1H) 7.45-7.59 (m, 1H) 7.90 (d, J=5.75 Hz, 1H) 8.11-8.24 (m, 1H) 8.39 (dd, J=10.45, 2.75 Hz, 1H).

Step 2

2 g of 21c (7.84 mmol, 1 eq) and 3.04 g of diisopropylethylamine (23.52 mmol, 4.10 mL, 3 eq) were dissolved in 20 mL of tetrahydrofuran, to which 1.88 g of phenyl chloroformate (12.01 mmol, 1.50 mL, 1.53 eq) was then added at 0° C. The reaction solution was stirred at 0° C. for 3.5 hours. After the reaction was completed, a reaction solution containing 21d was obtained, which was used directly for the next step.

Step 3

To the reaction solution obtained in step 2 was added 1.64 g of 21e (16.03 mmol, 2.08 mL, 2 eq). The reaction solution was stirred at room temperature for 16 hours. After the reaction was completed, the reaction solution was diluted with 80 mL of ethyl acetate, and washed with saturated brine (80 mL*3). The organic phase was collected, dried over anhydrous sodium sulfate, and filtered. The filtrate was concentrated under reduced pressure. The residue was isolated by preparative chromatography (Column type: Phenomenex Synergi Max-RP 250*50 mm*10 um; mobile phase: [water (0.225% FA)-ACN]; B %: 0%-30%, 30 MIN) to afford a product 21f.

Step 4

1 g of 21f (2.65 mmol, 1 eq) was dissolved in 20 mL of ethanol and 4 mL of water at room temperature. After nitrogen protection, 739.92 mg of iron powder (13.52 mmol, 5 eq) and 708.74 mg of ammonium chloride (13.25 mmol, 5 eq) were added to the mixture. The reaction solution was stirred at 30° C. for 16 hours. After the reaction was completed, the reaction solution was filtered. The filtrate was collected, and concentrated under reduced pressure to remove the solvent. The residue was adjusted to pH of 11 with saturated sodium carbonate solution, diluted with 30 mL of saturated saline, and extracted with ethyl acetate (30 mL*3). The organic phase was collected, dried over anhydrous sodium sulfate, and filtered. The filtrate was concentrated under reduced pressure to afford a crude product 21g, which was used directly in the next step without purification.

Step 5

875.89 mg of 5e (2.88 mmol, 1 eq), 1.31 g of HATU (3.45 mmol, 1.2 eq) and 1.12 g of diisopropylethylamine (8.64 mmol, 1.50 mL, 3 eq) were dissolved in 10 mL of DMF at room temperature, and stirred for 0.5 hour. To the mixture was then added 1 g of 21g (2.88 mmol, 1 eq). The reaction solution was stirred at room temperature for 15.5 hours. After the reaction was completed, the reaction solution was diluted with 50 mL of saturated saline and extracted with ethyl acetate (50 mL*3). The organic phase was collected, dried over anhydrous sodium sulfate, and filtered. The filtrate was concentrated under reduced pressure, and the residue was isolated by preparative chromatography (Column type: Phenomenex Synergi Max-RP 250*50 mm*10 µm; mobile phase: [A: water (0.225% FA), B: ACN]; B %: 10%-40%, 35 min) to afford the product of Example 21. $^1$HNMR (400 MHz, DMSO-$d_6$) δ ppm 11.01 (s, 1H), 10.57-9.58 (m, 1H), 8.91 (s, 1H), 8.10 (s, 1H), 7.97 (br d, J=13.0 Hz, 1H), 7.51-7.30 (m, 7H), 6.65-6.51 (m, 1H), 3.87 (br d, J=7.0 Hz, 3H), 2.89 (s, 4H), 2.57 (br s, 2H), 2.33 (s, 6H), 1.34-1.14 (m, 1H), 0.64-0.51 (m, 2H), 0.49-0.33 (m, 2H).

Example 22

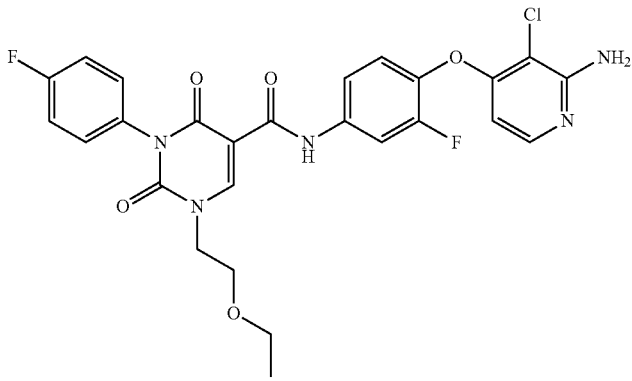

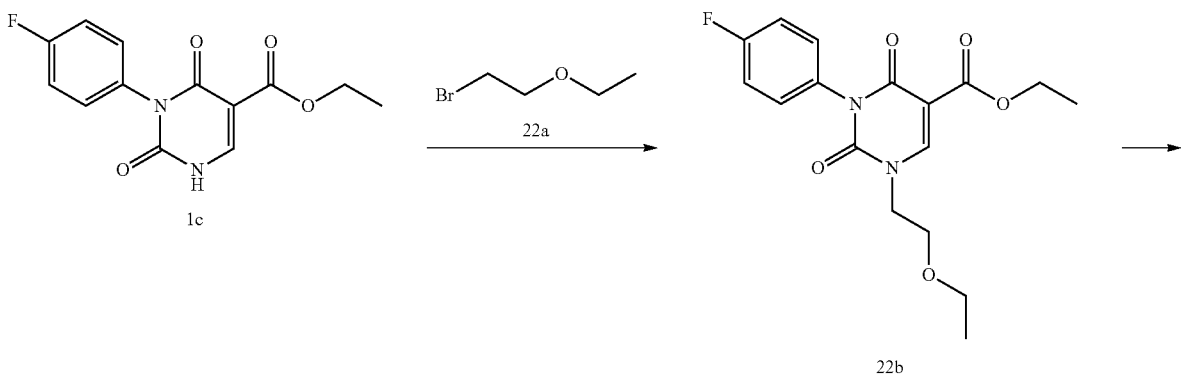

-continued

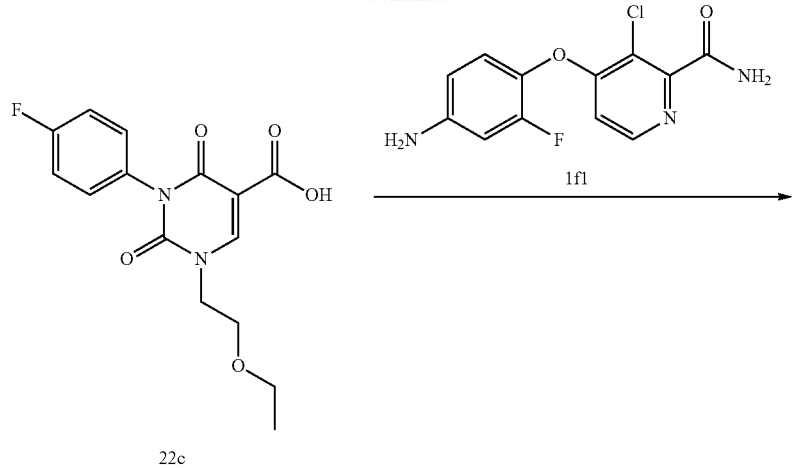

22c

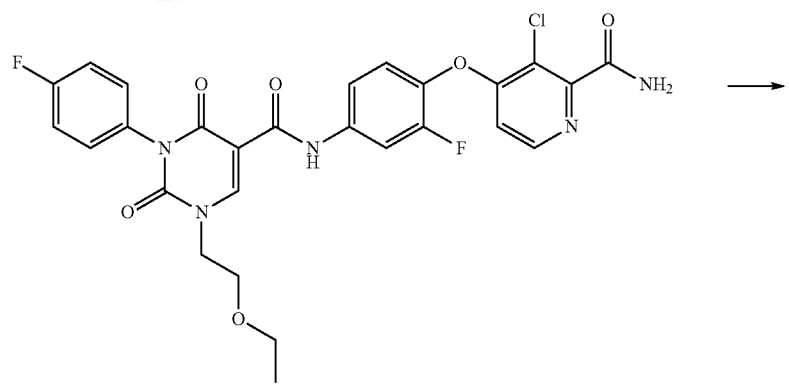

22d

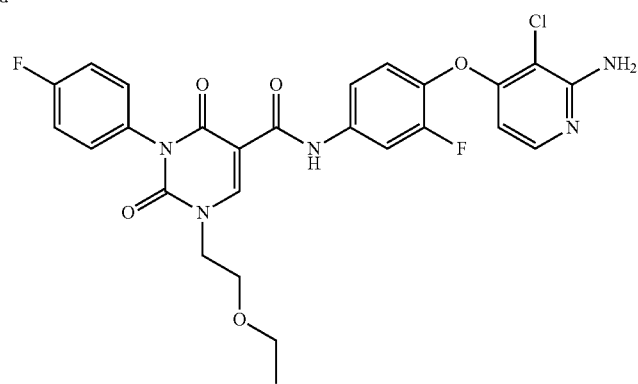

Example 22

Step 1

22b was obtained by the method as described for intermediate 1d.

Step 2

22c was obtained by the method as described for intermediate 1e. $^1$H NMR (400 MHz, DMSO-$d_6$) δ ppm 12.70-12.29 (m, 1H), 8.67 (s, 1H), 7.43-7.27 (m, 4H), 4.15-4.07 (m, 2H), 3.66-3.58 (m, 2H), 3.53-3.47 (m, 2H), 1.12 (t, J=7.0 Hz, 3H).

Step 3

500 mg of 22c (1.55 mmol, 1 eq), 707.87 mg of HATU (1.86 mmol, 1.2 eq) and 601.53 mg of diisopropylethylamine (4.65 mmol, 0.81 mL, 3 eq) were dissolved in 10 mL of DMF, and stirred at room temperature for 0.5 hour. To the mixture was added 400 mg of 1f1 (1.42 mmol, 0.92 eq). The reaction solution was stirred at room temperature for 2 hours. After the reaction was completed, the reaction solution was diluted with 100 mL of ethyl acetate, and washed with saturated ammonium chloride (60 mL*3) and saturated brine (100 mL*3). The organic phase was collected, dried over anhydrous sodium sulfate, and filtered. The filtrate was concentrated under reduced pressure to afford a crude product 22d, which was used directly in the next step without purification.
Step 4
The product of Example 22 was obtained by the method as described for the product of Example 1. ¹H NMR (400 MHz, DMSO-d$_6$) δ ppm 10.97 (s, 1H), 8.75 (s, 1H), 8.02-7.88 (m, 1H), 7.81-7.69 (m, 1H), 7.49-7.28 (m, 6H), 6.41 (s, 2H), 5.98-5.90 (m, 1H), 4.23-4.08 (m, 2H), 3.65 (t, J=5.0 Hz, 2H), 3.52 (d, J=7.0 Hz, 2H), 1.13 (t, J=7.0 Hz, 3H).
Example 23
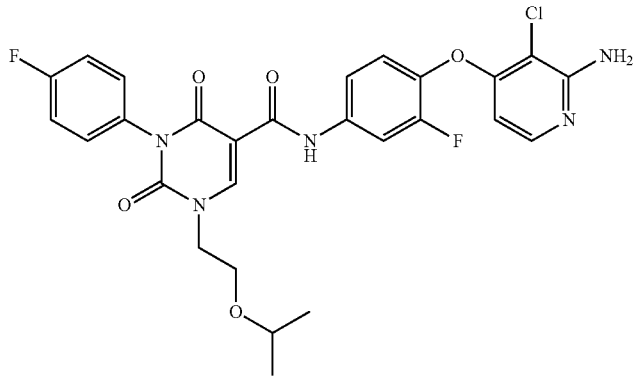
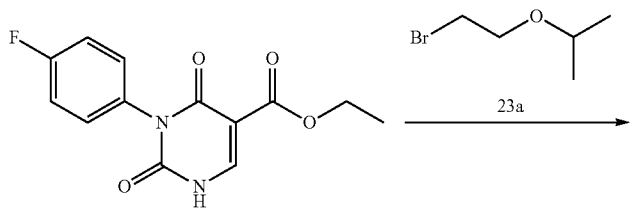
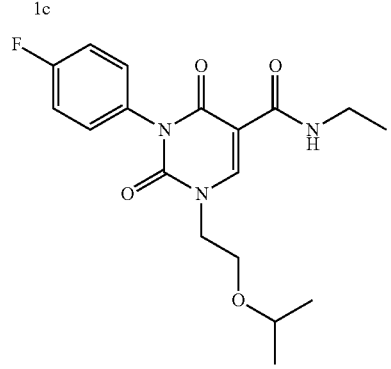
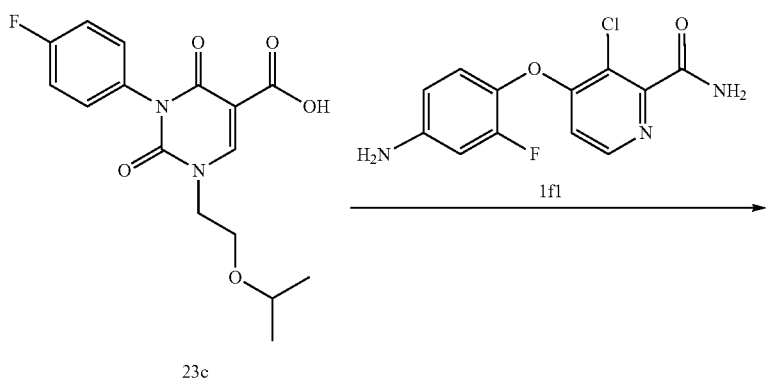

-continued

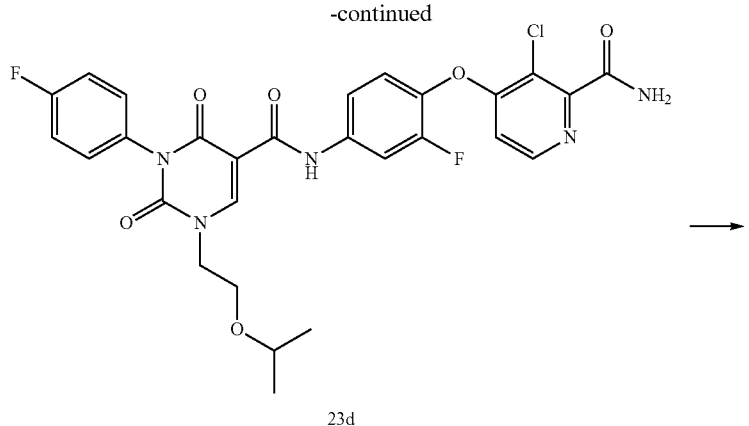
23d

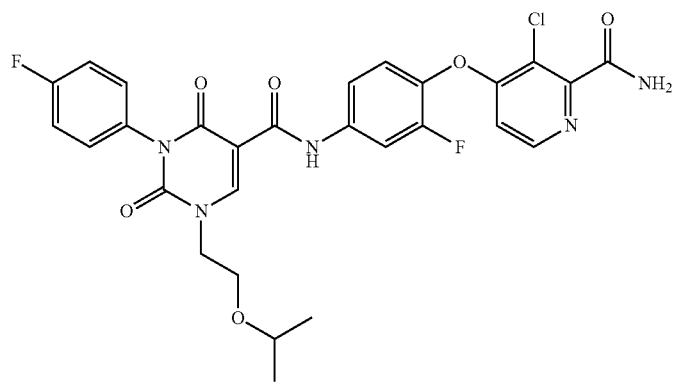
Example 23

23b was obtained by the method as described for intermediate 1d.

Step 2

23c was obtained by the method as described for intermediate 1e. ¹H NMR (400 MHz, DMSO-d₆) δ ppm 12.78-12.37 (m, 1H), 8.68 (s, 1H), 7.41-7.30 (m, 4H), 4.10-4.02 (m, 2H), 3.67-3.57 (m, 3H), 1.11-1.07 (m, 6H).

Step 3

23d was obtained by the method as described for intermediate 22d.

Step 4

The product of Example 23 was obtained by the method as described for the product of Example 1. ¹H NMR (400 MHz, DMSO-d₆) δ ppm 11.07-10.87 (m, 1H), 8.77 (s, 1H), 8.04-7.86 (m, 1H), 7.82-7.70 (m, 1H), 7.36 (s, 6H), 6.41 (s, 2H), 5.98-5.89 (m, 1H), 4.21-4.06 (m, 2H), 3.69-3.61 (m, 3H), 1.11 (d, J=6.1 Hz, 6H).

Example 24

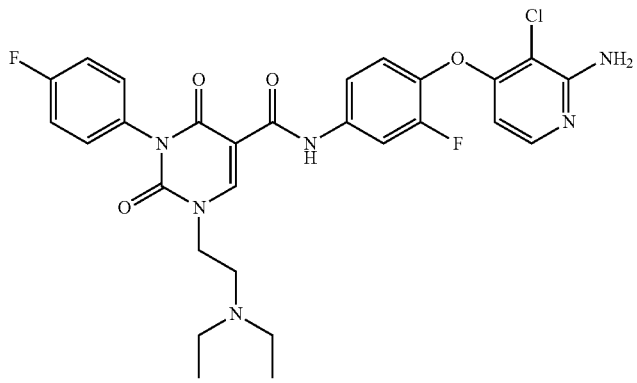

-continued
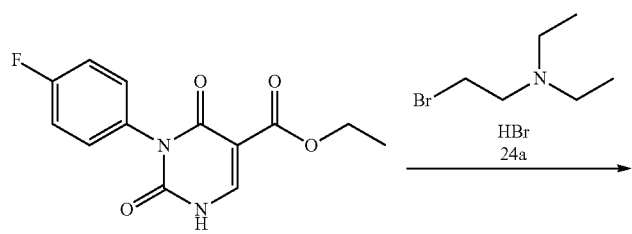
1c
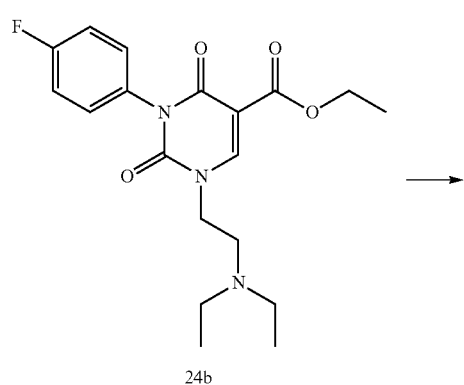
24b
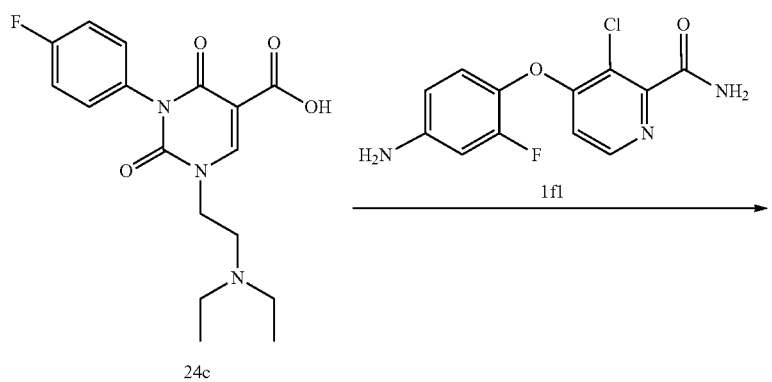
24c
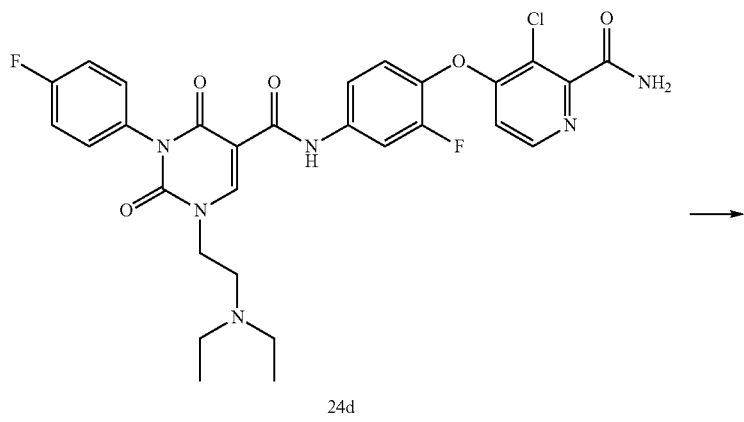
24d

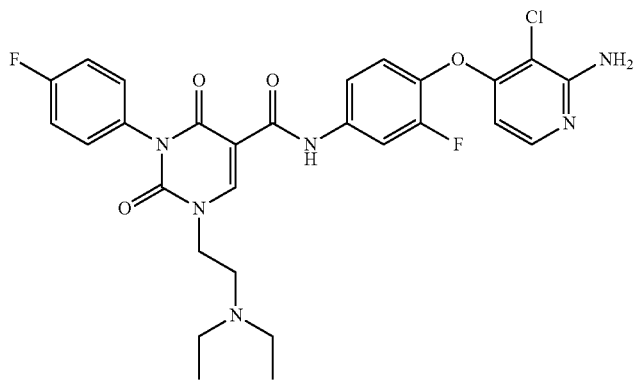

Example 24

Step 1

24b was obtained by the method as described for intermediate 1d.

Step 2

24c was obtained by the method as described for intermediate 1e.

Step 3

24d was obtained by the method as described for intermediate 22d.

Step 4

The product of Example 24 was obtained by the method as described for the product of Example 1. $^1$H NMR (400 MHz, DMSO-$d_6$) δ ppm 0.94 (t, J=7.03 Hz, 6H) 2.64 (s, 2H) 4.03 (br t, J=5.50 Hz, 2H) 5.93 (d, J=5.75 Hz, 1H) 6.41 (s, 2H) 7.24-7.34 (m, 1H) 7.38 (d, J=6.72 Hz, 4H) 7.48 (br d, J=8.68 Hz, 1H) 7.76 (d, J=5.62 Hz, 1H) 7.95 (dd, J=12.90, 2.02 Hz, 1H) 8.28 (s, 1H) 8.76 (s, 1H) 10.97 (s, 1H).

Assay Example 1: Assay of Activity of Binding to c-MET Enzyme

Reagents and Materials:
Reaction buffer: 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO and corresponding cofactor Compound Formulation:
The test compounds were dissolved in 100% DMSO to 0.33 μM and subjected to a 3-fold serial dilution using a fully automated microplate pretreatment system ECHO to obtain 10 concentrations.

Reaction Operations:
1) dissolving the substrate in the fresh prepared buffer
2) adding the required cofactor to the above buffer
3) adding enzyme to the above solution, and mixing well
4) adding test sample solution and incubating at room temperature for 20 minutes
5) adding $^{33}$P-ATP to the reaction solution, and then incubating at room temperature for 2 hours
6) detecting radiation signals
7) analyzing the results using GraphPad Prism software
   Results of assay: See Table 1.
   Conclusions: The compounds disclosed herein have strong inhibitory activity against c-MET/AXL enzyme.

TABLE 1

| Compound | AXL IC$_{50}$ (nM) | c-MET IC$_{50}$ (nM) |
|---|---|---|
| Example 1 | 2.07 | 2.17 |
| Example 2 | 2.64 | 1.76 |
| Example 4 | 17.7 | 2.89 |
| Example 5 | 2.51 | 2.51 |
| Example 6 | 4.6 | 16.9 |
| Example 7 | 2.06 | 3.77 |
| Example 9 | 3.11 | 12.4 |
| Example 11 | 3.11 | 1.43 |
| Example 12 | 3.18 | 7.18 |
| Example 13 | 6.69 | 7.35 |
| Example 14 | 3.52 | 4.79 |
| Example 15 | 3.74 | 4.05 |
| Example 16 | 3.81 | 9.35 |
| Example 17 | 4.41 | 2.01 |
| Example 18 | 5.59 | 1.44 |
| Example 21 | 1.07 | 14.63 |
| Example 22 | 43.99 | 13.36 |
| Example 23 | 5 | 26.15 |
| Example 24 | 19.03 | 59.26 |

Assay Example 2: Assay of Inhibitory Effect on Cell Proliferation

Reagents and Materials:
1. cell culture: DMEM medium, fetal bovine serum, DPBS
2. cell line: MKN45 gastric cancer cell line
3. detection reagent: live cell detection kit CellTiter-Glo
4. other main materials and reagents: compound dilution plate, middle plate, detection plate, DMSO Principle of Assay:
The content of ATP directly reflects the number and state of cells. By quantitation of ATP, the number of living cells can be detected. The living cell detection kit contains luciferase and its substrate. Through the participation of ATP, the luciferase can catalyze the substrate to emit a stable light signal. The number of ATP in the cells was determined by detecting the intensity of the signal. The light signal was directly proportional to the number of ATP in the cells, while ATP was positively correlated with the number of living cells, so that the proliferation of cells can be detected. The test plate was analyzed using Envision from PE Inc.

Method of Assay:

1. Preparation of the Cell Plate

The MKN45 cells were seeded into a 384-well plate with 200 cells per well. The cell plate was placed in a carbon dioxide incubator and incubated overnight.

2. Preparation of Compounds

Compounds were subject to a 5-fold serial dilution with Echo to obtain nine concentrations, in duplicate.

3. Treatment of Cells with Compounds

The compounds were transferred to the cell plate at an initial concentration of 10 NM. The cell plate was placed in a carbon dioxide incubator and incubated for three days.

4. Detection

A Promega CellTiter-Glo reagent was added to the cell plate and incubated at room temperature for 10 minutes to stabilize the luminescence signal. A PerkinElmer Envision multi-label analyzer was used for reading.

Results of assay: See Table 2.

Conclusions: The compounds disclosed herein showed superior inhibitory activity against MKN45 cells.

TABLE 2

| Test compounds | MKN45 cell IC$_{50}$ (nM) |
|---|---|
| BMS777607 | 436 |
| Example 1 | 54 |
| Example 2 | 78 |
| Example 3 | 27 |
| Example 5 | 11 |
| Example 8 | 374 |
| Example 9 | 365 |
| Example 11 | 240 |
| Example 12 | 315 |
| Example 13 | 38 |
| Example 14 | 30 |
| Example 15 | 12.6 |
| Example 16 | 50.7 |
| Example 17 | 7.64 |
| Example 18 | 12.1 |
| Example 19 | 41 |
| Example 20 | 29.1 |

Assay Example 3: Assay of Drug Efficacy in a Model with Subcutaneous Xenograft Tumor of MKN45 Gastric Cancer Cells Cell Culture:

MKN45 cells were cultured in vitro in monolayer. The culture conditions were RPMI1640 medium plus 10% heat-inactivated fetal bovine serum, 1% penicillin-streptomycin, 37° C., and 5% $CO_2$. The passaging was carried out by conventional digestion with trypsin-EDTA twice a week. When the cells were in the exponential growth phase, the cells were collected, counted, and inoculated.

Animals:

BALB/c nude mice, male, 6-8 weeks old, weighted 18-22 grams.

Tumor Inoculation:

0.2 ml of a suspension containing $5 \times 10^6$ MKN45 cells was inoculated subcutaneously on the right back of each mouse. When the average volume of the tumor reached about 160 mm$^3$, administration to each group was started.

Assay index: the assay index is to investigate whether the tumor growth is inhibited, delayed or cured. Tumor diameter was measured twice a week with a vernier caliper. The calculation formula of tumor volume is: $V=0.5a \times b^2$, wherein a and b represent the long and short diameters of the tumor, respectively. The anti-tumor efficacy (TGI) of the compound was evaluated by T-C (day) and T/C (%).

Assay results: See Table 3.

Conclusions: The compounds disclosed herein showed a better tumor inhibiting effect than BMS777607 in the drug efficacy assay in the model with subcutaneous xenograft tumor of MKN45 gastric cancer cells.

TABLE 3

Evaluation of anti-tumor efficacy of the test drugs in the model with xenograft tumor of human gastric cancer cells (calculated based on the tumor volume on day 14 after administration)

| Group | Tumor volume (mm$^3$)$^a$ (Day 14) | T/C (%) | TGI (%) | P value $^b$ |
|---|---|---|---|---|
| blank | 1,328 ± 281 | | | |
| Example 1 | 218 ± 31 | 16.5 | 95.1 | 0.044 |
| Example 5 | 196 ± 17 | 15.3 | 96.9 | 0.042 |

Note:
$^a$Mean + SEM.
$^b$ The p value was calculated based on tumor volume.

Assay Example 4: Assay of Drug Efficacy in a Model with Subcutaneous Xenograft Tumor of Hs746t Gastric Cancer Cells Cell Culture:

Human gastric cancer Hs746t cells were cultured in vitro in monolayer. The culture conditions were DMEM medium plus 10% fetal bovine serum, 100 U/mL penicillin and 100 U/mL streptomycin, 37° C., 5% $CO_2$ incubator. The passaging was carried out by conventional digestion with trypsin-EDTA twice a week. When the cell saturation was 80%-90%, and the number met the requirements, the cells were collected, counted, and inoculated.

Animals:

BALB/c nude mice, male, 6-8 weeks old, weighted 18-22 grams.

Tumor Inoculation:

0.2 mL ($2 \times 10^6$, cells:Matrigel=1:1) of HS 746T cells were subcutaneously inoculated on the right back of each mouse. When the average tumor volume reached about 100-150 mm$^3$, administration to each group was started.

Assay index: The assay index is to investigate whether tumor growth is inhibited, delayed or cured. Tumor diameter was measured twice a week with a vernier caliper. The calculation formula of tumor volume is: $V=0.5a \times b^2$, wherein a and b represent the long and short diameters of the tumor, respectively. The anti-tumor efficacy (TGI) of the compound was evaluated by T-C (day) and T/C (%).

Assay results: See Table 4.

Conclusions: In the drug efficacy assay in the model with subcutaneous xenograft tumor of Hs746t gastric cancer cells, the compound of Example 17 disclosed herein is effective at a dose of 1.5 mpk; the compounds of Example 5 and Example 17 show better tumor inhibitory effects than BMS777607 and LY2801653 at the same dose of 4.5 mpk; the compounds of Example 5 and Example 17 disclosed herein eliminated tumors at the dose of 9 mpk. The compounds disclosed herein have good tumor inhibitory activity.

TABLE 4

Evaluation of anti-tumor effect of the test drugs in the model with xenograft tumor of human Hs746t gastric cancer cells (Calculated based on tumor volume on day 21 after administration)

| Group | Dosage | Tumor volume (mm³)[a] (Day 0) | Tumor volume (mm³)[a] (Day 20) | TGI (%) | T/C (%) (Day 20) |
|---|---|---|---|---|---|
| blank | — | 127 ± 9 | 2537 ± 425 | — | — |
| BMS777607 | 4.5 mpk | 127 ± 11 | 1872 ± 355 | 27.61% | 73.58 |
| LY2801653 | 4.5 mpk | 127 ± 12 | 88 ± 13 | 101.62% | 3.45 |
| Example 5 | 4.5 mpk | 126 ± 10 | 20 ± 8 | 104.43% | 0.78 |
| Example 5 | 9 mpk | 127 ± 10 | 0 ± 0 | 105.01% | 0.00 |
| Example 17 | 1.5 mpk | 127 ± 12 | 780 ± 195 | 74.16% | 30.68 |
| Example 17 | 4.5 mpk | 127 ± 13 | 4 ± 2 | 104.82% | 0.15 |
| Example 17 | 9 mpk | 127 ± 9 | 0 ± 0 | 105.02% | 0.00 |

Note:
[a]Mean ± SEM.

What is claimed is:

1. A compound of Formula (IV 2), or a pharmaceutically acceptable salt thereof,

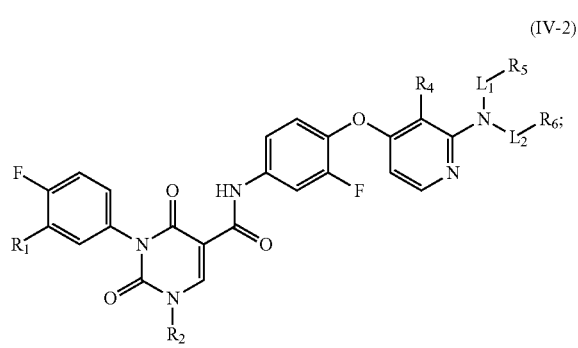

(IV-2)

wherein, $R_1$ is selected from the group consisting of —H, halogen and $C_{1-6}$ alkyl;

$R_2$ is selected from the group consisting of —NH$_2$, $C_{1-6}$ alkyl, $C_{1-6}$ heteroalkyl, and $C_{2-6}$ alkenyl, wherein the $C_{1-6}$ alkyl, $C_{1-6}$ heteroalkyl, and $C_{2-6}$ alkenyl are optionally substituted with 1, 2 or 3 R;

$R_4$ is selected from the group consisting of —H, —CN, halogen, $C_{1-4}$ alkyl, $C_{1-4}$ heteroalkyl, $C_{3-6}$ cycloalkyl, 3- to 6-membered saturated, or partially unsaturated heterocycloalkyl and 5- to 6-membered heteroaryl;

$R_5$ and $R_6$ are each independently selected from the group consisting of —H, —NH$_2$, $C_{1-6}$ alkyl, $C_{1-6}$ heteroalkyl, $C_{3-6}$ cycloalkyl and 3- to 6-membered saturated, or partially unsaturated heterocycloalkyl, wherein the $C_{1-6}$ alkyl, $C_{1-6}$ heteroalkyl, $C_{3-6}$ cycloalkyl and 3- to 6-membered saturated, or partially unsaturated heterocycloalkyl are optionally substituted with 1, 2 or 3 R;

$L_1$ and $L_2$ are each independently selected from the group consisting of a single bond and —C(=O)—;

R is each independently selected from the group consisting of —F, —Cl, —Br, —I, —OH, —CN, —NH$_2$, $C_{1-4}$ alkyl, $C_{1-4}$ heteroalkyl, $C_{3-6}$ cycloalkyl and 3- to 6-membered heterocycloalkyl, wherein the $C_{1-4}$ alkyl, $C_{1-4}$ heteroalkyl, $C_{3-6}$ cycloalkyl and 3- to 6-membered heterocycloalkyl are optionally substituted with 1, 2 or 3 R';

R' is selected from the group consisting of —F, —Cl, —Br, —I, —OH, —CN, —NH$_2$, —CH$_3$, —CF$_3$, —CHF$_2$, CH$_3$O—, CH$_3$CH$_2$—, CH$_3$CH$_2$O—, —COOH, —NH(CH$_3$), —N(CH$_3$)$_2$,

and the $C_{1-6}$ heteroalkyl, 3- to 6-membered heterocycloalkyl, $C_{1-4}$ heteroalkyl and 5- to 6-membered heteroaryl each independently contains 1, 2 or 3 heteroatoms or heteroatom groups selected from the group consisting of —N—, —NH—, —O—, —S—, =O, =S, —C(=O)O—, —C(=O)—, —C(=O)NH—, —C(=S)—, —S(=O)—, —S(=O)$_2$—, —C(=NH)—, —S(=O)$_2$NH—, —S(=O)NH—, and —NHC(=O)NH—.

2. The compound or a pharmaceutically acceptable salt thereof according to claim 1, wherein R is selected from the group consisting of —F, —Cl, —Br, —I, —OH, —CN, —NH$_2$, —CH$_3$, —CF$_3$, —CHF$_2$, CH$_3$O—, CH$_3$CH$_2$—, CH$_3$CH$_2$O—, —COOH, —NH(CH$_3$), —N(CH$_3$)$_2$,

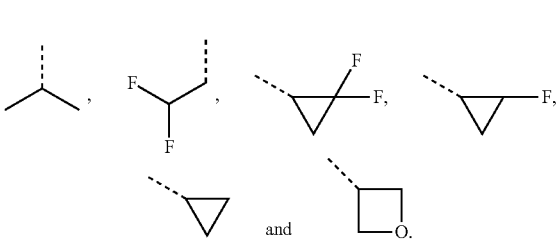

3. The compound or a pharmaceutically acceptable salt thereof according to claim 1, wherein $R_1$ is —H.

4. The compound or a pharmaceutically acceptable salt thereof according to claim 1, wherein $R_2$ is selected from the group consisting of —NH$_2$, $C_{1-4}$ alkyl, $C_{1-4}$ heteroalkyl and $C_{2-4}$ alkenyl, wherein the $C_{1-4}$ alkyl, $C_{1-4}$ heteroalkyl and $C_{2-4}$ alkenyl are optionally substituted with 1, 2 or 3 R.

5. The compound or a pharmaceutically acceptable salt thereof according to claim 4, wherein $R_2$ is selected from the group consisting of —NH$_2$, —CH$_3$, CH$_3$CH$_2$—,

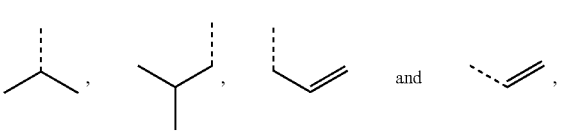

wherein the —CH$_3$, CH$_3$CH$_2$—,

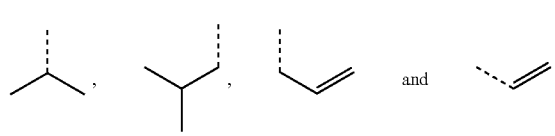

are optionally substituted with 1, 2 or 3 R.

6. The compound or a pharmaceutically acceptable salt thereof according to claim 5, wherein $R_2$ is selected from the group consisting of —CH$_3$,

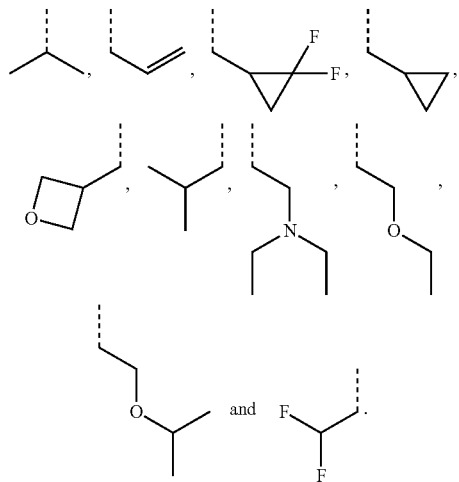

7. The compound or a pharmaceutically acceptable salt thereof according to claim 1, wherein $R_4$ is selected from the group consisting of —H, —Cl and —CN.

8. The compound or a pharmaceutically acceptable salt thereof according to claim 1, wherein $R_5$ and $R_6$ are each independently selected from the group consisting of —H, —NH$_2$, —CH$_3$, CH$_3$CH$_2$—,

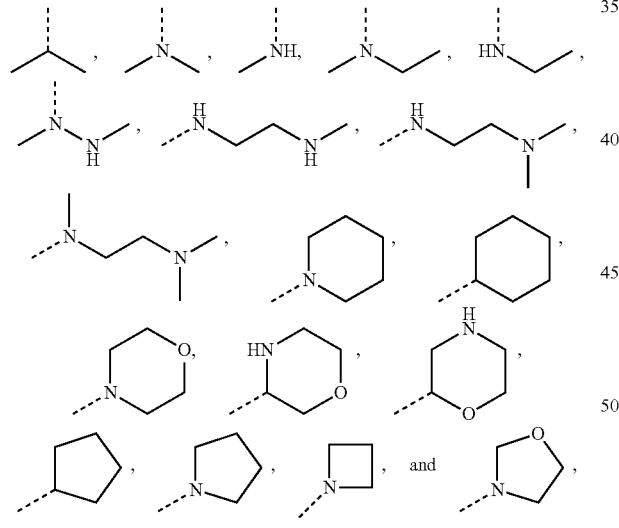

wherein the —CH$_3$, CH$_3$CH$_2$—,

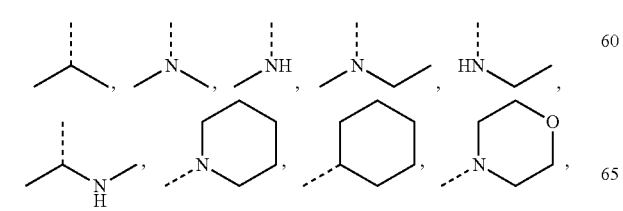

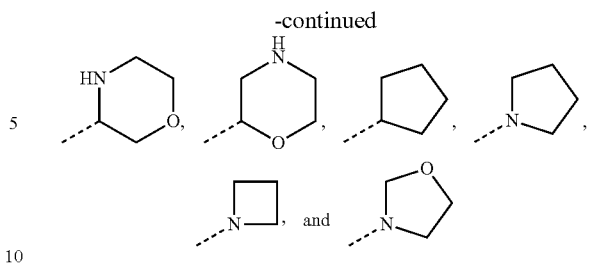

are optionally substituted with 1, 2 or 3 R.

9. The compound or a pharmaceutically acceptable salt thereof according to claim 8, wherein $R_5$ and $R_6$ are each independently selected from the group consisting of —H, —NH$_2$, —CH$_3$, CH$_3$CH$_2$—,

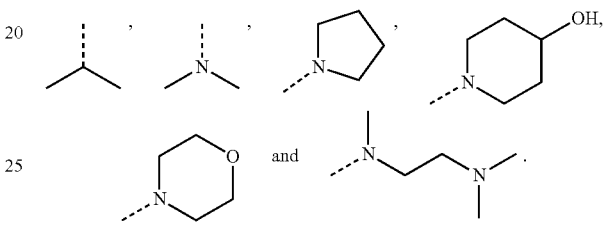

10. The compound or a pharmaceutically acceptable salt thereof according to claim 1, wherein the moiety

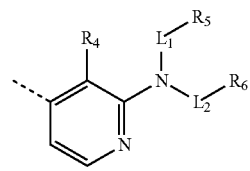

is selected from the group consisting of

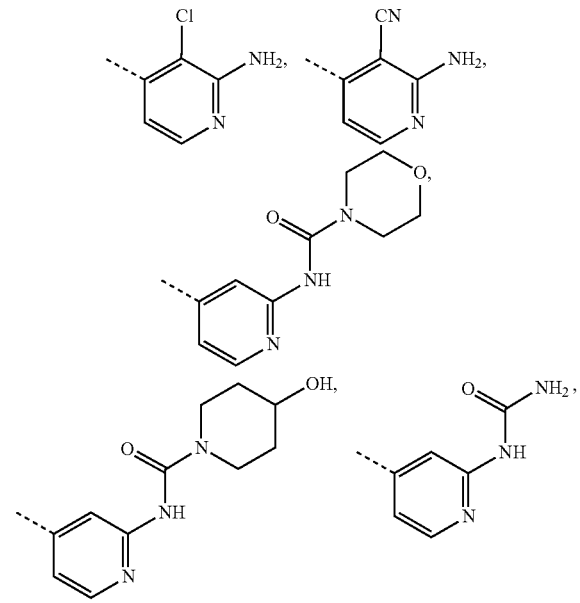

-continued

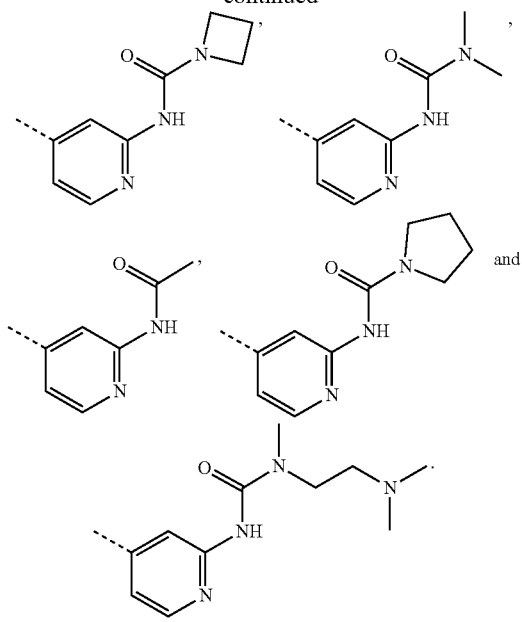

11. The compound or a pharmaceutically acceptable salt thereof according to claim 1, wherein the compound is

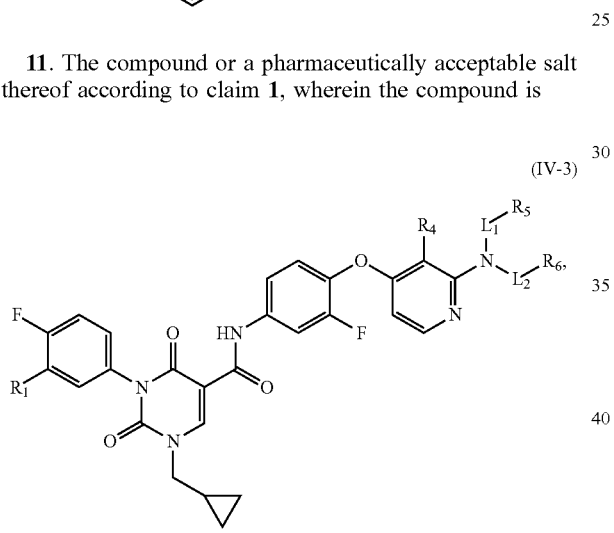

(IV-3)

wherein $L_1$, $L_2$, $R_1$, $R_4$, $R_5$ and $R_6$ are defined as in claim 1.

12. The compound or a pharmaceutically acceptable salt thereof according to claim 11, wherein the compound is selected from the group consisting of

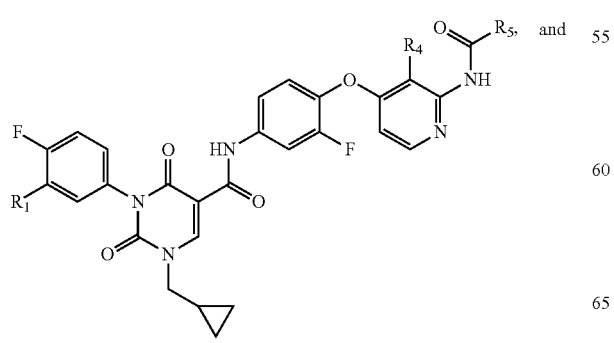

(IV-4)

-continued

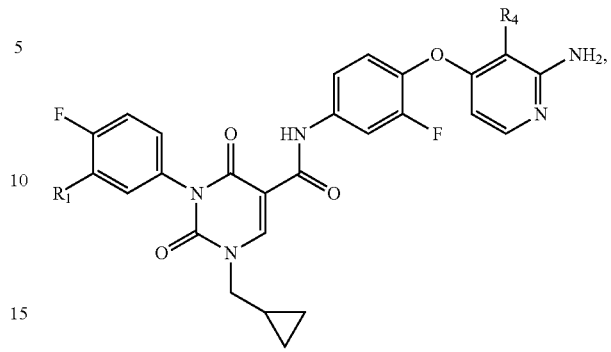

(IV-5)

wherein $R_1$, $R_4$ and $R_5$ are defined as in claim 11.

13. The compound of claim 1, or a pharmaceutically acceptable salt thereof, wherein the compound is selected from the group consisting of:

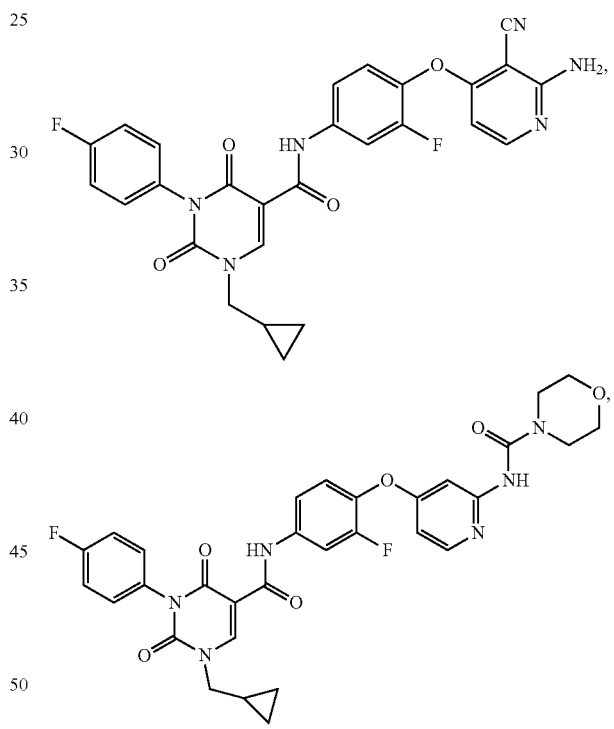

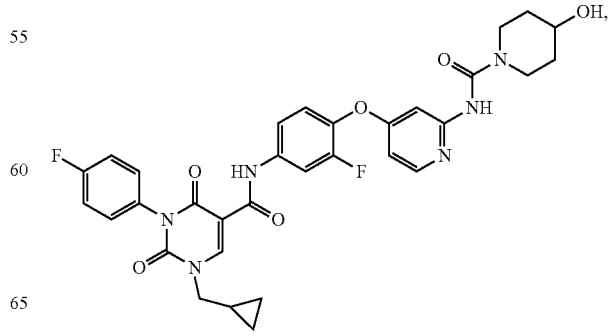

109
-continued
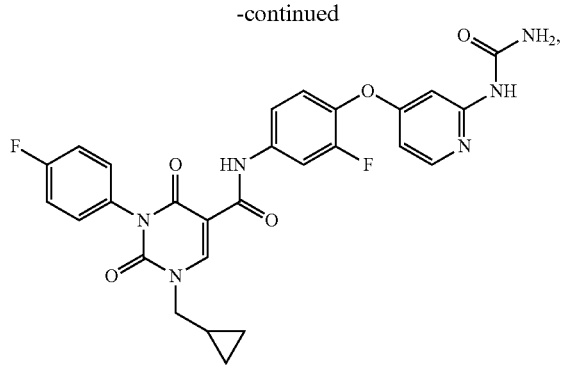
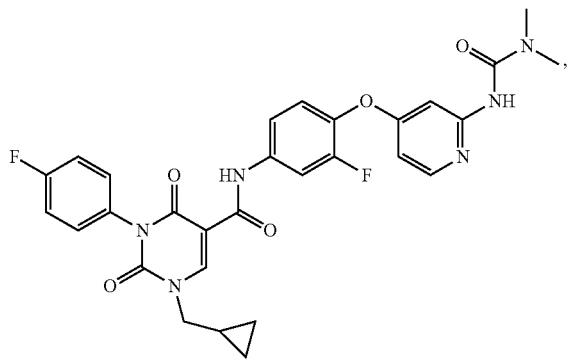 [SMILES: CN(C)C(=O)Nc1cc(Oc2ccc(NC(=O)c3cn(CC4CC4)c(=O)n(-c4ccc(F)cc4)c3=O)cc2F)ccn1]
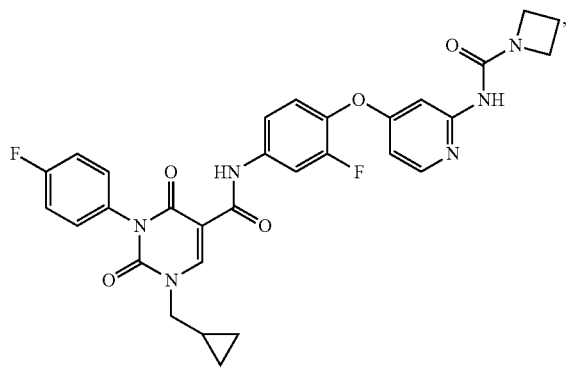
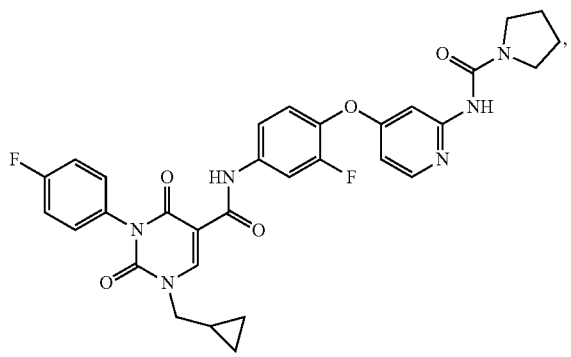
110
-continued
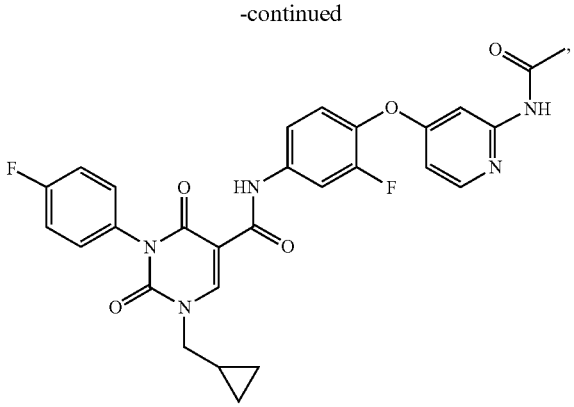
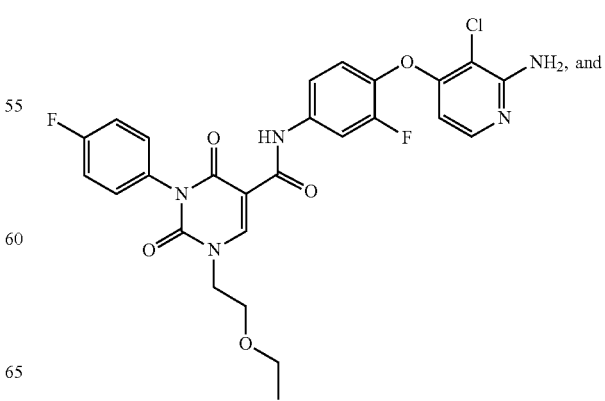

-continued

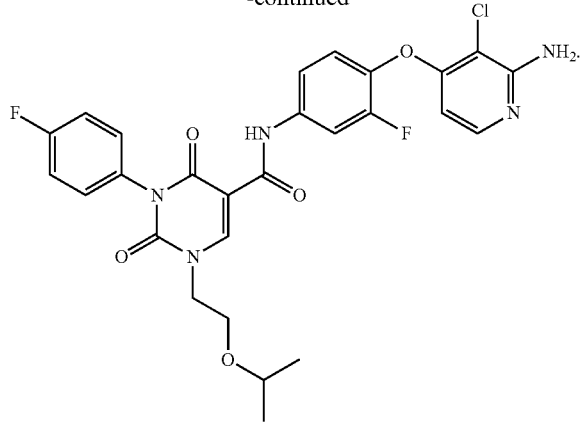

14. A pharmaceutical composition, comprising a therapeutically effective amount of a compound or a pharmaceutically acceptable salt thereof according to claim 1, and pharmaceutically acceptable carrier(s).

15. The compound or a pharmaceutically acceptable salt thereof according to claim 1, wherein each of $L_1$ and $L_2$ is a single bond and each of $R_5$ and $R_6$ is —H.

16. The compound or a pharmaceutically acceptable salt thereof according to claim 15, wherein R is selected from the group consisting of —F, —Cl, —Br, —I, —OH, —CN, —NH$_2$, —CH$_3$, —CF$_3$, —CHF$_2$, CH$_3$O—, CH$_3$CH$_2$—, CH$_3$CH$_2$O—, —COOH, —NH(CH$_3$), —N(CH$_3$)$_2$,

and

17. The compound or a pharmaceutically acceptable salt thereof according to claim 15, wherein $R_1$ is —H.

18. The compound or a pharmaceutically acceptable salt thereof according to claim 15, wherein $R_2$ is selected from the group consisting of —NH$_2$, $C_{1-4}$ alkyl, $C_{1-4}$ heteroalkyl and $C_{2-4}$ alkenyl, wherein the $C_{1-4}$ alkyl, $C_{1-4}$ heteroalkyl and $C_{2-4}$ alkenyl are optionally substituted with 1, 2 or 3 R.

19. The compound or a pharmaceutically acceptable salt thereof according to claim 18, wherein $R_2$ is selected from the group consisting of —CH$_3$,

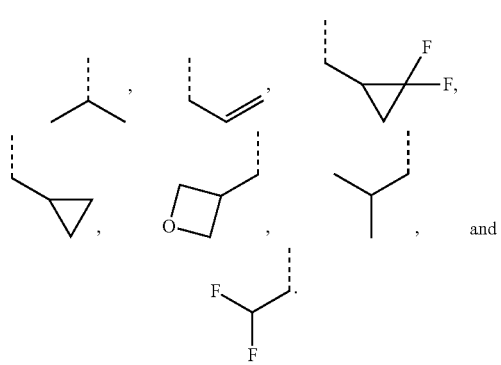

and

20. The compound or a pharmaceutically acceptable salt thereof according to claim 15, wherein $R_4$ is —Cl.

21. The compound of claim 1, or a pharmaceutically acceptable salt thereof, wherein the compound is selected from the group consisting of:

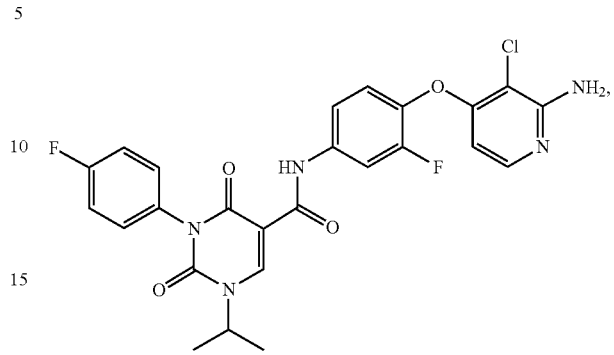

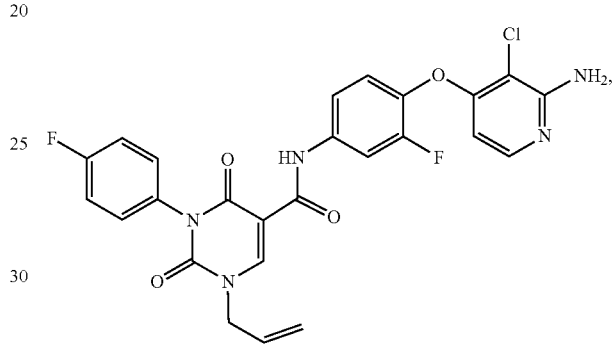

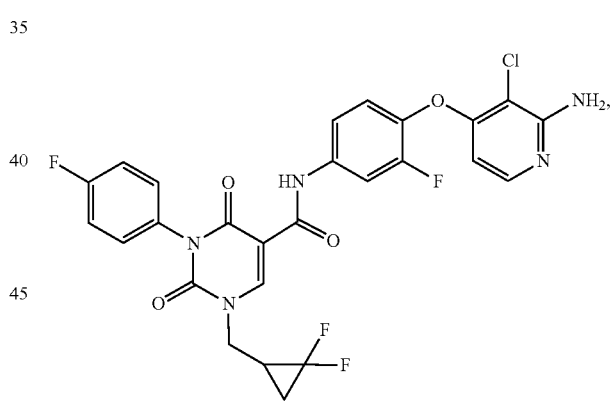

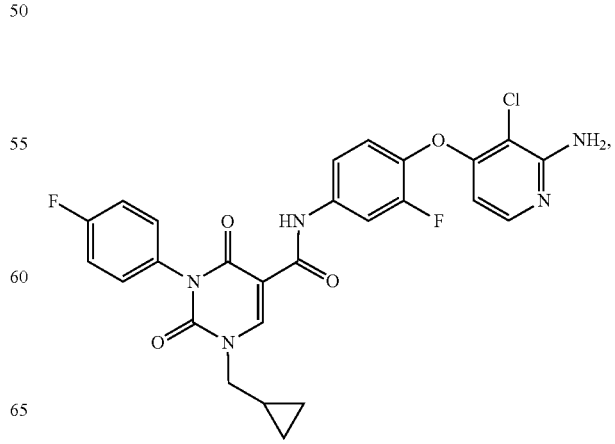

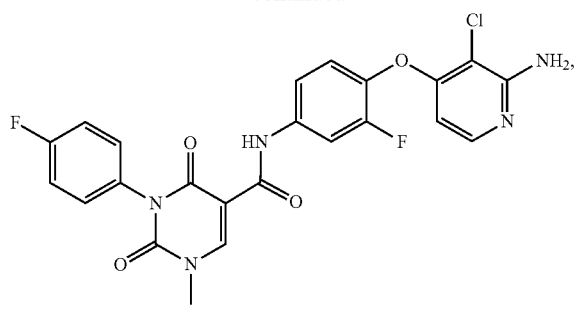
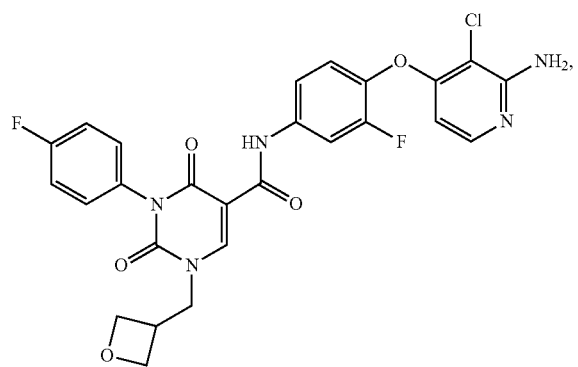
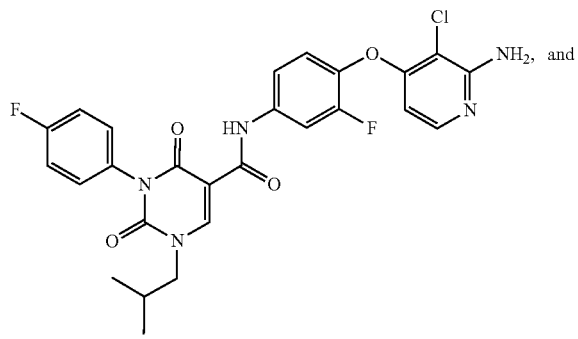
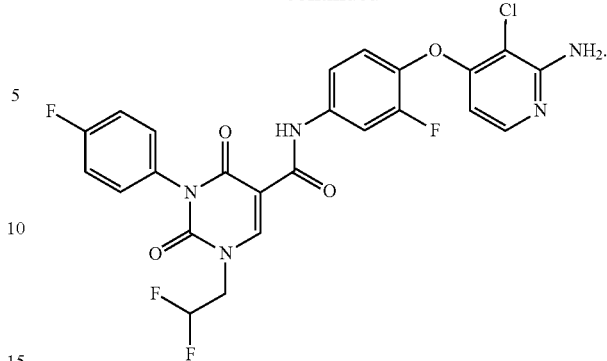
22. The compound of claim 1, or a pharmaceutically acceptable salt thereof, wherein the compound is
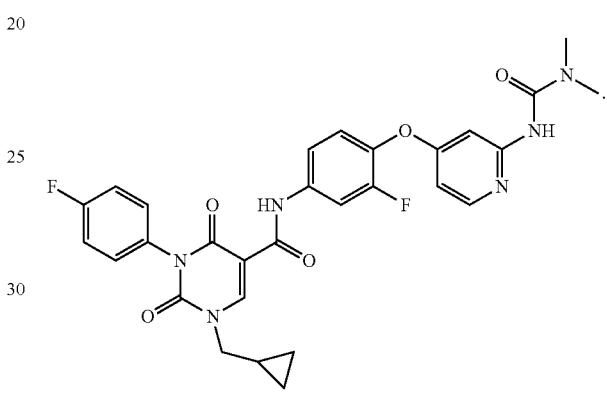
23. A pharmaceutical composition, comprising a therapeutically effective amount of a compound or a pharmaceutically acceptable salt thereof according to claim 22, and pharmaceutically acceptable carrier(s).
* * * * *

UNITED STATES PATENT AND TRADEMARK OFFICE
CERTIFICATE OF CORRECTION

PATENT NO. : 11,623,923 B2  
APPLICATION NO. : 16/766510  
DATED : April 11, 2023  
INVENTOR(S) : Li et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 135 days.

Signed and Sealed this  
Thirty-first Day of December, 2024

Derrick Brent  
*Acting Director of the United States Patent and Trademark Office*